(12) United States Patent
Braun

(10) Patent No.: US 12,419,670 B2
(45) Date of Patent: Sep. 23, 2025

(54) METHODS FOR BONE COMPRESSION AND/OR FIXATION

(71) Applicant: BraunVest LLC, Charlotte, VT (US)

(72) Inventor: John T. Braun, Charlotte, VT (US)

(73) Assignee: BraunVest, LLC, Charlotte, VT (US)

( * ) Notice: Subject to any disclaimer, the term of this patent is extended or adjusted under 35 U.S.C. 154(b) by 308 days.

(21) Appl. No.: 18/202,864

(22) Filed: May 26, 2023

(65) Prior Publication Data

US 2023/0310040 A1 Oct. 5, 2023

Related U.S. Application Data

(63) Continuation-in-part of application No. 17/452,774, filed on Oct. 28, 2021, which is a continuation-in-part
(Continued)

(51) Int. Cl.
*A61B 17/86* (2006.01)
*A61B 17/70* (2006.01)
(Continued)

(52) U.S. Cl.
CPC ...... *A61B 17/7053* (2013.01); *A61B 17/8635* (2013.01); *A61B 17/864* (2013.01); *A61B 2017/564* (2013.01); *A61B 2017/681* (2013.01)

(58) Field of Classification Search
CPC .......................... A61B 17/7053; A61B 17/864
See application file for complete search history.

(56) References Cited

U.S. PATENT DOCUMENTS

| 5,387,213 A | 2/1995 | Breard et al. |
| 5,951,560 A | 9/1999 | Simon et al. |

(Continued)

FOREIGN PATENT DOCUMENTS

| WO | WO2009128074 | 10/2009 |
| WO | WO2017127532 | 7/2017 |

OTHER PUBLICATIONS

U.S. Appl. No. 16/601,471, Office Action dated May 27, 2021 (8 pgs.).
(Continued)

*Primary Examiner* — Christian A Sevilla
(74) *Attorney, Agent, or Firm* — Matthew D. Thayne; Thayne and Davis LLC

(57) ABSTRACT

Methods for bone correction and/or fixation of bone anchors, such as spinal deformity correction. In some implementations, the method may comprise advancing a bone anchor through a proximal bone wall and into a bone. Bone material may be compressed in a region distal of the bone anchor by advancing the bone anchor within the bone to form a compressed bone region, the compressed bone region extending, at least in part, distally of the bone anchor, and in some cases within an inner chamber of the bone anchor. The compressed bone region may increase the fixation strength of the bone anchor within the bone to decrease the chances of the bone anchor becoming dislodged within the bone. In some cases, the compressed bone region may be advanced to and/or compressed against a distal cortical bone to obtain functional bicortical purchase without penetration of the cortical bone.

21 Claims, 38 Drawing Sheets

Related U.S. Application Data of application No. 16/601,471, filed on Oct. 14, 2019, now Pat. No. 11,246,636.

(60) Provisional application No. 62/839,397, filed on Apr. 26, 2019.

(51) Int. Cl.
*A61B 17/56* (2006.01)
*A61B 17/68* (2006.01)

(56) References Cited

U.S. PATENT DOCUMENTS

| | | | |
|---|---|---|---|
| 6,299,613 B1 | 10/2001 | Ogilvie et al. | |
| 7,285,121 B2 | 10/2007 | Braun et al. | |
| 7,297,146 B2 | 11/2007 | Braun et al. | |
| 7,637,978 B2 | 12/2009 | Jung | |
| 7,691,131 B2 | 4/2010 | Graf | |
| 7,727,258 B2 | 6/2010 | Graf | |
| 7,845,945 B2* | 12/2010 | Canter | A61C 8/0022 433/173 |
| 7,862,573 B2* | 1/2011 | Darois | B25B 23/065 606/139 |
| 8,128,402 B2* | 3/2012 | Lundgren | A61C 8/0092 433/174 |
| 8,172,880 B2 | 5/2012 | Graf | |
| 8,177,810 B2 | 5/2012 | Ferree | |
| 8,221,457 B2 | 7/2012 | Delecrin et al. | |
| 8,641,736 B2 | 2/2014 | Marik et al. | |
| 8,870,573 B2* | 10/2014 | Hung | A61C 8/0039 433/174 |
| 8,979,874 B2 | 3/2015 | Darois et al. | |
| 9,271,725 B2* | 3/2016 | Colesanti | A61B 17/068 |
| 9,433,442 B2 | 9/2016 | Lindemann et al. | |
| 9,833,230 B2 | 12/2017 | Stone | |
| 10,179,015 B2 | 1/2019 | Lavigne et al. | |
| 11,246,636 B2 | 2/2022 | Braun | |
| 11,974,792 B2 | 5/2024 | Braun | |
| 2002/0082598 A1 | 6/2002 | Teitelbaum | |
| 2007/0292820 A1* | 12/2007 | Canter | A61C 8/0022 606/304 |
| 2010/0131010 A1 | 5/2010 | Graf | |
| 2012/0189984 A1 | 7/2012 | Holmes | |
| 2013/0253587 A1 | 9/2013 | Carls et al. | |
| 2013/0304032 A1 | 11/2013 | Sardesai | |
| 2020/0337753 A1 | 10/2020 | Braun | |

OTHER PUBLICATIONS

U.S. Appl. No. 17/671,469 Notice of Allowance and Fees Due, dated Jan. 8, 2024 (7 pgs).

U.S. Appl. No. 17/452,774, Notice of Allowance and Fees Due, dated Feb. 20, 2025, (13 pgs).

* cited by examiner

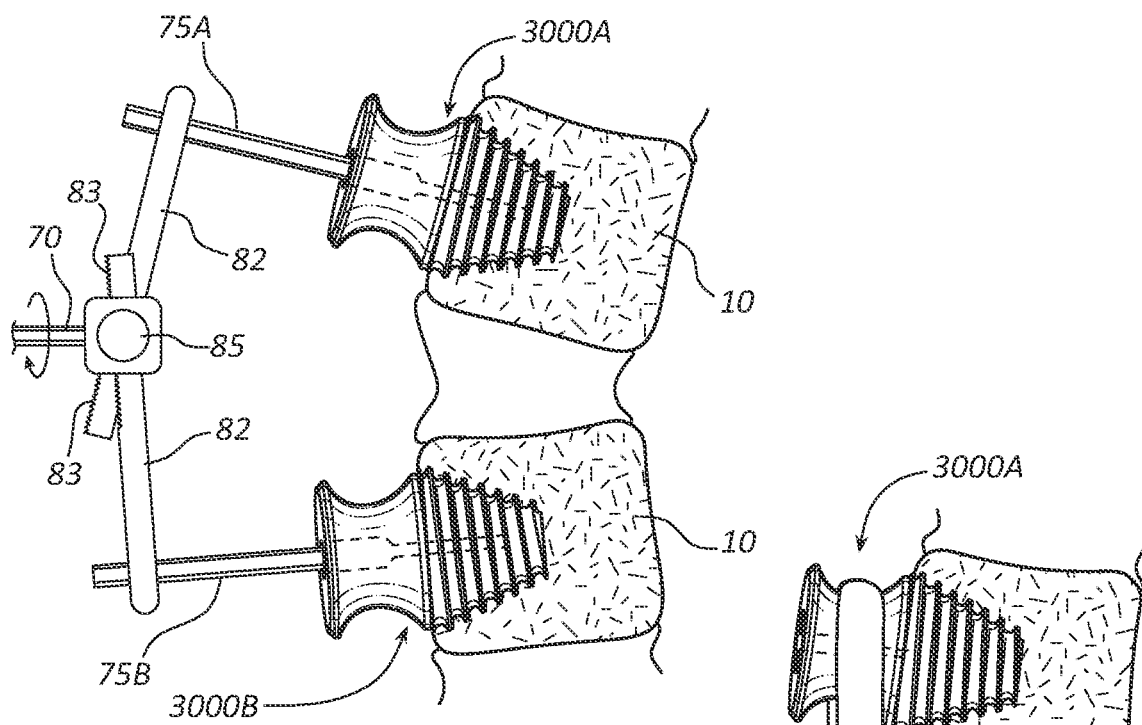
FIG. 30A
FIG. 30C
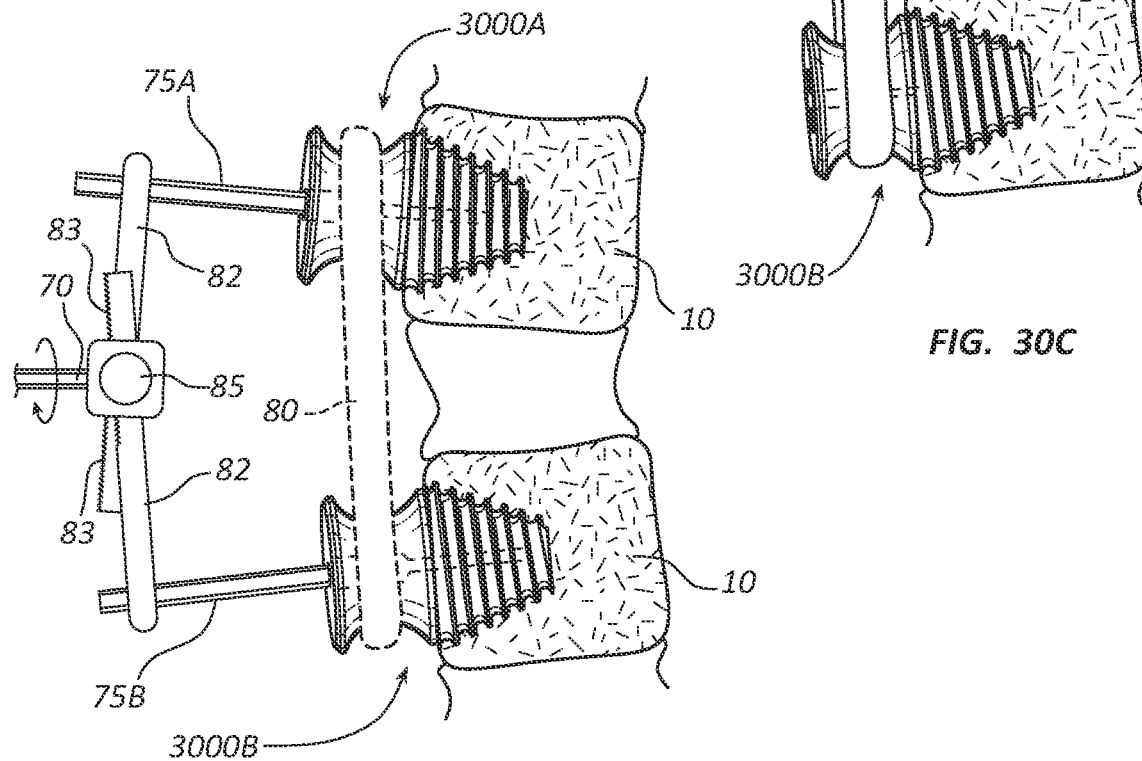
FIG. 30B

METHODS FOR BONE COMPRESSION AND/OR FIXATION

CROSS-REFERENCE TO RELATED APPLICATIONS

This application is a continuation-in-part of co-pending U.S. patent application Ser. No. 17/452,774 filed on Oct. 28, 2021 and titled "SYSTEMS, METHODS, AND APPARATUS FOR SPINAL DEFORMITY CORRECTION," which is a continuation-in-part of U.S. patent application Ser. No. 16/601,471 filed on Oct. 14, 2019 and titled "SYSTEMS, METHODS, AND APPARATUS FOR SPINAL DEFORMITY CORRECTION," which issued as U.S. Pat. No. 11,246,636, which claims the benefit under 35 U.S.C. § 119(e) of U.S. Provisional Patent Application No. 62/839,397, which was filed Apr. 26, 2019 and titled "SYSTEMS, METHODS, AND APPARATUS FOR SPINAL DEFORMITY CORRECTION." Each of the aforementioned applications is hereby incorporated herein by reference in its entirety.

SUMMARY

Embodiments of apparatus and methods are disclosed herein that relate to correction and/or stabilization of spinal deformities, such as scoliosis, are disclosed herein. In some specific embodiments disclosed herein, such devices and/or systems may comprise bone anchors that may be particularly configured for coupling with vertebral bodies and that may be used in certain spinal surgeries, such as fusionless spinal surgeries that are often used to treat scoliosis and other similar deformities.

Additionally, similar bone anchors may be configured and used in other contexts, such as, for example, repair of tendons and/or ligaments or repair of bone fractures. Various methods are disclosed herein that take advantage of certain features and structures of various vertebral or other bone anchors disclosed herein to enhance fixation strength and/or stability of such anchors, and/or to reduce the chances of failure, by compacting bone, such as cancellous bone and "plowing" or advancing bone in front (distally) of the anchor as it is advanced to create a compressed bone region in front of the anchor. This compressed bone region effectively extends the functional length of the anchor further into the bone. Thus, when advanced sufficiently to contact a distal cortical wall, functional bicortical purchase, which often provides a particularly strong fixation with bone, may be achieved without actually penetrating the distal cortical wall, which can often be dangerous, particularly in the context of spinal deformity correction procedures.

Existing bone anchors used for such procedures are typically configured to extend entirely through the vertebral bodies to provide for bicortical purchase. This is because the cortex portion of the vertebral body is viewed as the only portion of the bone with sufficient strength to hold the screw or other bone anchor in place while the corrective forces are being applied to the spinal column via a series of such screws/anchors. Inadequate screw purchase, such as purchase that terminates within the cancellous portion of the vertebra may therefore result in undesirable movement of the screw within the vertebral body, which may result in recurrence of the spinal deformity or at least decreased efficacy of the spinal correction system.

Other anchors have been developed, such as those disclosed in U.S. Pat. No. 7,285,121 titled "Devices and Methods for the Correction and Treatment of Spinal Deformities," which patent is incorporated herein by reference in its entirety. The anchors disclosed in this previous patent are shorter in length but wider to provide additional surface area for obtaining stable purchase in the cancellous bone without necessarily requiring bicortical purchase. However, the present inventor has improved upon this design by providing, in some embodiments, an inner chamber that is threaded, which may provide a number of benefits, such as drawing additional bone into the chamber, placing such bone under compression to accelerate healing and incorporation with the implant, and/or providing a differential in force and/or surface tension between various portions of the anchor, such as between the inner and outer surfaces of the implant, to further improve stability, healing, and/or provide other benefits.

Although the preferred embodiments disclosed herein are designed and configured for use in connection with spinal bones, such as vertebral bodies, the inventive principles disclosed herein may find application in other types of bones or even other types of tissues, particularly bones and/or tissues with similar characteristics to vertebral bones (i.e., largely cancellous bone/tissue and/or comprising an insufficient cortex). Examples of such alternative applications include suture anchors for rotator cuff repair and other similar surgical procedures. It should be understood therefore that the bone anchors and other features/aspects disclosed herein may be used in connection with any bones or other anatomical feature, including but not limited to those involving use of sutures and/or tethers for applying a force to such anatomical feature, but particularly those features having both cortical and cancellous bone regions.

Thus, in a more specific example of a bone anchor, such as a bone anchor configured for vertebral attachment, the bone anchor may comprise an outer thread form that may be positioned on a tapered portion of the bone anchor. The bone anchor may further comprise an inner chamber, which may be located along the same portion along the primary axis of the bone anchor. The inner chamber may also comprise a thread form and/or may taper in an opposite direction. The inner and outer thread forms may differ from one another, such as by providing a larger thread depth on the thread form in the inner chamber, for example. Similarly, the inner and outer threads may differ in other aspects to increase the aforementioned force differential, such as by differing in thread direction/handedness, number of starts, angle, pitch diameter, major diameter, minor diameter, etc.

This may allow for increased fixation while increasing stimulation of bone ingrowth by increasing the forces that stimulate such bone growth. In other words, by providing an inner chamber that has threads and/or tapers, as described herein, bone may be inserted into and compacted within the chamber as the anchor is advanced. Although providing a tapered chamber or a chamber that otherwise decreases in volume from the distal end towards the proximal end is preferred, some such benefits may be provided by providing a cylindrical chamber comprising internal threads.

In some embodiments, the bone anchor may further comprise an engagement member or other means for engaging a ligament to impart a force to a vertebral body or other tissue or anatomical feature. Such engagement member or other feature may be incorporated directly into the bone anchor or may be part of a cap or other such element that may be coupled with the bone anchor. In some embodiments, the engagement member or engagement means and/or a cap or the like to which the engagement member/means is coupled may be rotatable with respect to the thread form(s) of the anchor to allow for selective repositioning of the engagement member/means following insertion of the bone anchor into a vertebral body or other bone or body tissue.

In a more specific example of a bone anchor, such as a bone screw or other bone anchor, configured for engagement with a vertebral body or other bone, the anchor may comprise a first section comprising an at least substantially conical shape in cross section and a second section comprising an at least substantially cylindrical shape in cross section. The second section may be positioned distal of the first section and may form a tip of the bone anchor. The bone anchor may further comprise an inner chamber. An outer thread form may be formed on an outer surface of the bone anchor and an inner thread form may be formed on an inner surface of the bone anchor within the inner chamber.

Some embodiments may further comprise a third section, which may comprise a cross-sectional width in a direction at least substantially perpendicular to an elongated axis of the bone anchor. The cross-sectional width may be maximal between opposing ends of the third section. In some such embodiments, the third section may comprise an outer surface having a convex, curved shape. The third section may be positioned in between the first section and the second section.

In some embodiments, the third section may comprise an outer thread form, which may, in some embodiments, begin at or at least substantially at a point of maximal width of the third section.

In some embodiments, the inner thread form may differ from the outer thread form so as to provide a differential in force between forces generated by the outer thread form on vertebral bone adjacent to the outer thread form and forces generated by the inner thread form on vertebral bone within the inner chamber.

In some embodiments, the second section may lack outer threads. In some embodiments, the second section may also, or alternatively, lack inner threads. The second section and/or distal most end of the bone anchor may comprise a sharp edge configured to facilitate penetration into a vertebral body.

In another example of a threaded bone anchor configured for engagement with a vertebral body, the anchor may comprise a tapered section comprising an outer thread form and an inner chamber comprising an inner thread form. The inner chamber may comprise a proximal end and a distal end and may taper or otherwise decrease in size, at least in part, between the distal end and the proximal end. The inner thread form may differ from the outer thread form so as to provide a differential in force between forces generated by the outer thread form on vertebral bone adjacent to the outer thread form and forces generated by the inner thread form on vertebral bone within the inner chamber, such as by differing in one or more of thread depth, thread direction, number of starts, angle, pitch diameter, major diameter, taper angle, and minor diameter. As a more specific example, in some embodiments, the inner thread form may comprise a larger thread depth than the outer thread form. Any of the aforementioned threads may be partial and/or transition along the thread form as well, if desired.

In some embodiments, the inner chamber may taper, in part or in whole, from a proximal portion of the bone anchor to a distal portion of the bone anchor to define a wider bone anchor width at a proximal portion of a tapering section of the bone anchor than at a distal portion of the tapering section.

Some embodiments may further comprise a non-tapered section positioned at a distal end of the bone anchor, such as a portion having a cylindrical shape in cross section. In some embodiments, the non-tapered section may lack threads and/or comprise a sharp distal edge to facilitate bone penetration.

In an example of a bone anchor configured for engagement with a vertebral body according to other embodiments, the bone anchor may comprise an outer surface configured to engage vertebral bone and extending along a longitudinal axis of the bone anchor. The outer surface may taper, at least in part, from a proximal portion of the bone anchor to a distal portion of the bone anchor to define a wider bone anchor width at a proximal portion of a tapering section of the bone anchor than at a distal portion of the tapering section. The bone anchor may further comprise an inner chamber configured to engage and compact vertebral bone therein. The inner chamber may taper in a direction opposite a direction in which the outer surface tapers such that at least a portion of the inner chamber is wider at a distal portion of the inner chamber than an adjacent proximal portion of the inner chamber.

In some embodiments, the inner chamber may comprise an inner thread form and/or the outer chamber may comprise an outer thread form. In some embodiments, the inner thread form of the inner chamber may differ from the outer thread form of the outer chamber so as to provide a differential in force between forces generated by the outer thread form on vertebral bone adjacent to the outer thread form and forces generated by the inner thread form on vertebral bone within the inner chamber.

Some embodiments may further comprise a cylindrical section, which may, in some embodiments, form a distal tip of the bone anchor configured to facilitate penetration into a vertebral body.

In an example of a system for spinal deformity correction according to some embodiments, the system may comprise a first bone anchor configured to be engaged with a first vertebral body. The first bone anchor may comprise an outer thread form formed on an outer surface of the first bone anchor and an inner chamber. The inner chamber may comprise at least one of a plurality of bone engaging protrusions formed on an inner surface of the first bone anchor within the inner chamber and a profile that increases in cross-sectional area, at least in part, from a proximal end of the inner chamber to a distal end of the inner chamber. The system may further comprise a second bone anchor configured to be engaged with a second vertebral body. The second bone anchor may comprise an outer thread form formed on an outer surface of the second bone anchor and an inner chamber. The second bone anchor may further comprise at least one of a plurality of bone engaging protrusions formed on an inner surface of the second bone anchor within the inner chamber and a profile that increases in cross-sectional area, at least in part, from a proximal end of the inner chamber to a distal end of the inner chamber. The system may further comprise a tether extending between the first bone anchor and the second bone anchor. The tether may be configured to apply a corrective force to the first and second vertebral bodies.

In some embodiments, the inner chamber of the first and/or second bone anchors may each comprise a plurality of bone engaging protrusions, each plurality of bone engaging protrusions of which may comprise an inner thread form formed on an inner surface of its respective inner chamber.

In some embodiments, the inner chamber of the first and/or second bone anchors may each comprise a plurality of bone engaging protrusions, each plurality of bone engaging protrusions of which may comprise a plurality of bone engaging spikes formed on an inner surface of its respective inner chamber.

In some embodiments, the first and/or second bone anchors may each further comprise a removable engagement member configured to be coupled with its respective bone anchor so as to protrude away from the vertebral body within which the bone anchor is engaged. In some such embodiments, one or more of the removable engagement members may comprise a seat for receiving the tether.

In some embodiments, the inner chamber of one or both of the first and second bone anchors may comprise at least one stepped region in which a cross-sectional area of the respective inner chamber decreases in a distal to proximal direction by way of one of more steps, either with or without tapering portions.

In some embodiments, the outer thread form of one or both of the first and second bone anchors may comprise at least two distinct sections. In some such embodiments, a bone anchor sleeve may be configured to receive a respective inner bone anchor piece, and the at least two distinct sections of each bone anchor may comprise a first section configured to threadably engage its respective bone anchor sleeve and a second section configured to threadably engage the vertebral body to which the respective bone anchor is coupled.

In some embodiments, the bone anchor sleeve may be configured to engage the first bone anchor so as to provide a region outside of the inner chamber of the first bone anchor within which vertebral bone may be compressed during installation, such as a region formed in between an outer surface of the inner piece and an inner surface of the outer piece.

In an example of a method for applying a corrective force to a spinal column according to some implementations, the method may comprise advancing a first bone anchor into a first vertebral body of a spinal column and compacting cancellous bone within an inner chamber of the first bone anchor. The inner chamber preferably comprises at least one of a plurality of bone engaging protrusions and a profile that increases in cross-sectional area, at least in part, from a proximal end of the inner chamber to a distal end of the inner chamber. The method may further comprise advancing a second bone anchor into a second vertebral body of the spinal column and compacting cancellous bone within an inner chamber of the second bone anchor. Again, the inner chamber of the second bone anchor preferably comprises at least one of a plurality of bone engaging protrusions and a profile that increases in cross-sectional area, at least in part, from a proximal end of the inner chamber to a distal end of the inner chamber. A tether/ligament may be coupled between the first and second bone anchors to apply a force between the first and second bone anchors and thereby apply a corrective force to at least a portion of the spinal column.

In some implementations, the inner chamber of one or both of the bone anchors may comprise a plurality of bone engaging protrusions. In some such implementations, the step of compacting cancellous bone within the inner chamber(s) may comprise drawing cancellous bone into the inner chamber(s) with the plurality of bone engaging protrusions while the respective bone anchor is advanced into its corresponding vertebral body.

In some implementations, the first bone anchor may be offset from the second bone anchor relative to the spinal column such that the corrective force includes a derotational corrective component.

Some implementations may further comprise advancing a third bone anchor into the first vertebral body adjacent to the first bone anchor and/or advancing a fourth bone anchor into the second vertebral body adjacent to the second bone anchor such that two (or more) bone anchors are coupled with one or more of the vertebral bodies subject to corrective forces using the inventive assembly.

In some implementations, the first bone anchor may comprise a first protrusion extending transverse to a primary axis of the first bone anchor and the second bone anchor comprises a second protrusion extending transverse to a primary axis of the second bone anchor. The step of coupling a tether between the first and second bone anchors may then comprise, for example coupling a tether to the first protrusion and the second protrusion. Alternatively, fixed arms may be coupled with the first and second protrusions, which arms may be configured to be forced together by way of, for example, a ratchet mechanism, to apply forces to the bone anchors.

In some implementations and/or embodiments comprising the aforementioned protrusions, the first protrusion may extend in a direction at least substantially opposite from the second protrusion relative to the spinal column such that that the corrective force includes a derotational corrective component.

In another example of a method for applying a corrective force to a spinal column, the method may comprise advancing a first bone anchor into a first vertebral body of a spinal column while simultaneously redistributing and compacting vertebral bone into an inner chamber of the first bone anchor and advancing a second bone anchor into a second vertebral body of the spinal column while simultaneously redistributing and compacting vertebral bone into an inner chamber of the second bone anchor. A tether/ligament may then be coupled between the first and second bone anchors to apply a force between the first and second bone anchors and thereby apply a corrective force to at least a portion of the spinal column.

Some implementations may further comprise increasing tension on the tether/ligament to increase the force between the first and second bone anchors, which may be done, for example, by increasing a size of at least a portion of an engagement member coupled to at least one of the first and second bone anchors and within which at least a portion of the tether is positioned, decreasing a length of the tether, or decreasing a length of the tether, such as heat shrinking the tether.

Some implementations may further comprise tensioning the first and second bone anchors with a temporary tether having a non-fixed length followed by coupling the tether between the first and second bone anchors and then removing the temporary tether from being coupled with the first and second bone anchors.

In other examples of methods for applying a corrective force to a spinal column, such methods may comprise advancing a first bone anchor through a proximal cortical wall of a first vertebral body of a spinal column and into the first vertebral body. Cancellous bone within the first vertebral body may then be compressed in a region distal of the first bone anchor, in some cases such region being aligned with an axis of the first bone anchor, by advancing the first bone anchor within the first vertebral body to form a compressed bone region distal of the first bone anchor. In some implementations, bone may be drawn in, churned, and/or compressed within an inner chamber of the first bone anchor such that, upon advancement, this bone is further compressed and advanced to form the compressed bone region.

In some implementations, the compressed bone region may be extended further distally of the first bone anchor by advancing the first bone anchor until the compressed bone region contacts a distal cortical wall opposite from the proximal cortical wall. Preferably, this step is performed so as to increase a fixation strength of the first bone anchor within the first vertebral body. For example, a continuous coupling may be formed between the compressed bone region and the first bone anchor, typically via features within an inner chamber of the first bone anchor, such that the effective or functional fixation length of the first bone anchor is extended by the compressed bone region and/or functionally provides the equivalent, or at least substantially the equivalent, of a bicortical purchase of the first vertebral body by the first bone anchor.

In some implementations, the compressed bone region may form a gradient of increasing bone density along an axis of the first bone anchor. Typically, the greatest bone density will be adjacent to the first bone anchor, with the density decreasing along the gradient from the proximal to the distal end of the compressed bone region.

Some implementations may further comprise advancing a second bone anchor through a proximal cortical wall of a second vertebral body of the spinal column and into the second vertebral body and compressing cancellous bone within the second vertebral body in a region distal of the second bone anchor by advancing the second bone anchor within the second vertebral body to form a compressed bone region distal of the second bone anchor. In some implementations, the compressed bone region may be advanced distally of the second bone anchor by advancing the second bone anchor until the compressed bone region contacts a distal cortical wall of the second vertebral body opposite from the proximal cortical wall of the second vertebral body. Again, preferably this increases a fixation strength of the second bone anchor within the second vertebral body and/or functionally provides the equivalent, or at least substantially the equivalent, of a bicortical purchase of the second vertebral body.

A tether or other preferably flexible coupling member may then be coupled between the first and second bone anchors to apply a force between the first and second bone anchors and thereby apply a corrective force to at least a portion of the spinal column of a patient.

In some implementations, the first and second bone anchors may each comprise an inner chamber. This may allow for compacting cancellous bone into the respective inner chambers of the first and second bone anchors as the first and second bone anchors are advanced such that the first and second bone anchors achieve bicortical fixation of the first and second vertebral bodies, respectively, without penetrating respective distal cortical walls of the first and second vertebral bodies.

In some implementations, the compressed bone region may be formed such that, upon healing, the compressed bone region is configured to form a solidified bone shaft that extends from the distal cortical wall to a distal end of the first bone anchor along an axis of the first bone anchor. In some implementations, the solidified bone shaft may comprise bone of a higher density than at least a portion of cancellous bone surrounding the solidified bone shaft within the first vertebral body. In some such implementations, the solidified bone shaft may comprise bone of a higher density than all, or at least substantially all, of the cancellous bone surrounding the solidified bone shaft within the first vertebral body.

In various examples of more general methods for fixation of a bone anchor, such methods may comprise advancing a bone anchor through a proximal bone wall and into a bone of a patient. Such a bone may comprise, for example, a vertebral bone or any other suitable bone, such as, for example, a pelvic bone, a tibia, a femur, a calcaneus, or a humerus.

Bone material within the bone may be compressed in a region distal of the bone anchor by advancing the bone anchor within the bone to form a compressed bone region. The compressed bone region may extend, at least in part, distally of the bone anchor. In some implementations, the compressed bone region may also extend into the bone anchor, such as into an inner chamber of the bone anchor. Preferably, the compressed bone region is formed so as to increase the fixation strength of the bone anchor within the bone to decrease the chances of the bone anchor becoming dislodged within the bone. In some implementations, the bone anchor may be extended to and coupled with cortical bone, such as a distal cortical wall of the bone. Some implementations may then further comprise coupling a flexible member to the bone anchor.

In some implementations, the flexible member may comprise a natural, flexible member, such as a human ligament or tendon, such as an Achilles tendon or a rotator cuff tendon. In some such implementations, the bone anchor may comprise a suture anchor configured to couple with the ligament or tendon. In some such implementations, the bone anchor may be directly coupled with an artificial flexible coupling member, such as a suture or the like, to facilitate coupling with the ligament or tendon.

In some implementations, the suture anchor may comprise an inner chamber. In some such implementations, the method may comprise compacting bone material into the inner chamber as the suture anchor is advanced to form the compressed bone region.

In some implementations, the flexible member may comprise a flexible coupling member, which, again, may comprise, for example, a suture, a band, an artificial ligament, or the like.

In some implementations, the bone anchor comprises an inner chamber, which inner chamber may comprise one or more features configured to draw bone into the chamber, remove and/or churn bone within the chamber, and/or provide opposing forces between inner and outer surfaces of the implant. For example, some implementations and/or embodiments may involve bone anchors having inner chambers with one or both of: (1) a plurality of bone engaging protrusions formed on an inner surface of the inner chamber; and (2) a profile that increases in cross-sectional area, at least in part, from a proximal end of the inner chamber to a distal end of the inner chamber. This may facilitate the method further comprising compressing bone material, such as cancellous bone material, into the inner chamber.

In some implementations, the inner chamber may comprise a plurality of bone engaging protrusions made up of an inner thread form formed on an inner surface of the inner chamber. In some such implementations, the inner thread form may differ from an outer thread form on the bone anchor, such as by way of, for example, thread direction/handedness, number of starts, angle, pitch diameter, major diameter, or minor diameter.

In some implementations in which the bone comprises a vertebral bone, the step of compressing bone material into the inner chamber may comprise compressing cancellous bone into the inner chamber while simultaneously forming the compressed bone region distally of the bone anchor and along an axis of the bone anchor and coupling a tether with the bone anchor to apply a corrective force to at least a portion of a spinal column of the patient. In some such implementations, the step of forming the compressed bone region distally of the bone anchor and along an axis of the bone anchor may be performed so as to contact a distal cortical wall and/or provide functional bicortical purchase with the bone screw without penetrating the distal cortical wall.

In some implementations of methods for increasing a fixation strength of a bone anchor, such methods may comprise advancing a bone anchor through a proximal cortical wall of a bone. In some such implementations, the bone anchor may comprise an inner chamber, in some cases with bone engaging features such as inner threads. Some implementations may further comprise advancing the bone anchor to compress cancellous bone into the inner chamber of the bone anchor. Some implementations may further comprise increasing an effective fixation length of the bone anchor by advancing and compressing cancellous bone along an axis of the bone anchor and in a region distal of the bone anchor. Some implementations may further comprise applying a force to the bone anchor. Preferably, the effective fixation length of the bone anchor provided by the compressed cancellous bone in the region distal of the bone anchor increases the fixation strength of the bone anchor within the bone.

In some implementations, the bone anchor may comprise a vertebral bone anchor and the bone may comprise a vertebral body. Alternatively, the bone may comprise, for example, a tibia, a femur, a calcaneus, or a humerus. In some implementations, the bone anchor may be used to fix a bone fracture and may therefore extend across a fracture point of the bone.

In some implementations, the step of applying a force to the bone anchor may comprise applying a force to the bone anchor with a flexible coupling member to apply a corrective force to a patient's spinal column.

In some implementations, the step of increasing an effective fixation length of the bone anchor by advancing and compressing cancellous bone along an axis of the bone anchor and in a region distal of the bone anchor may further comprise forming a compressed bone region along the region distal of the bone anchor. Some such implementations may further comprise advancing the bone anchor until the compressed bone region contacts a distal cortical wall of the bone opposite from the proximal cortical wall. In some such cases, this may result in fixation equivalent, or at least substantially equivalent, to bicortical fixation with the bone anchor.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIGS. 30A-30C are perspective views of a system for spinal deformity correction comprising a tensioning assembly according to some embodiments during a method for spinal correction using the system;

DETAILED DESCRIPTION

Figure 1A:
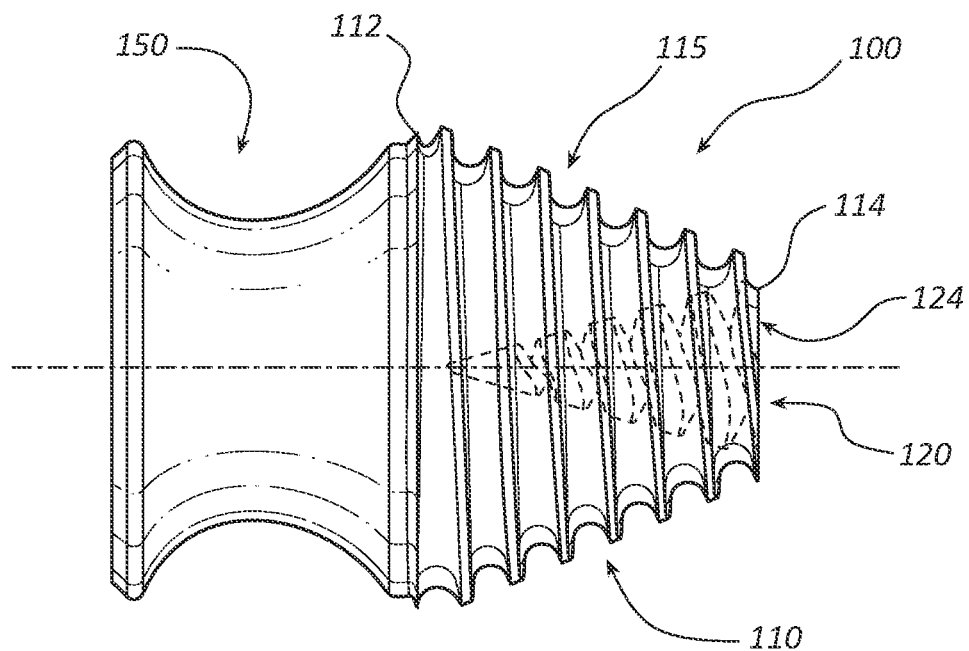
FIG. 1A is a perspective view of a vertebral bone anchor according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure but is merely representative of possible embodiments of the disclosure. In some cases, well-known structures, materials, or operations are not shown or described in detail.

As used herein, the term "substantially" refers to the complete or nearly complete extent or degree of an action, characteristic, property, state, structure, item, or result to function as indicated. For example, an object that is "substantially" cylindrical or "substantially" perpendicular would mean that the object/feature is either cylindrical/perpendicular or nearly cylindrical/perpendicular so as to result in the same or nearly the same function. The exact allowable degree of deviation provided by this term may depend on the specific context. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

Similarly, as used herein, the term "about" is used to provide flexibility to a numerical range endpoint by providing that a given value may be "a little above" or "a little below" the endpoint while still accomplishing the function associated with the range.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

Figure 1B:
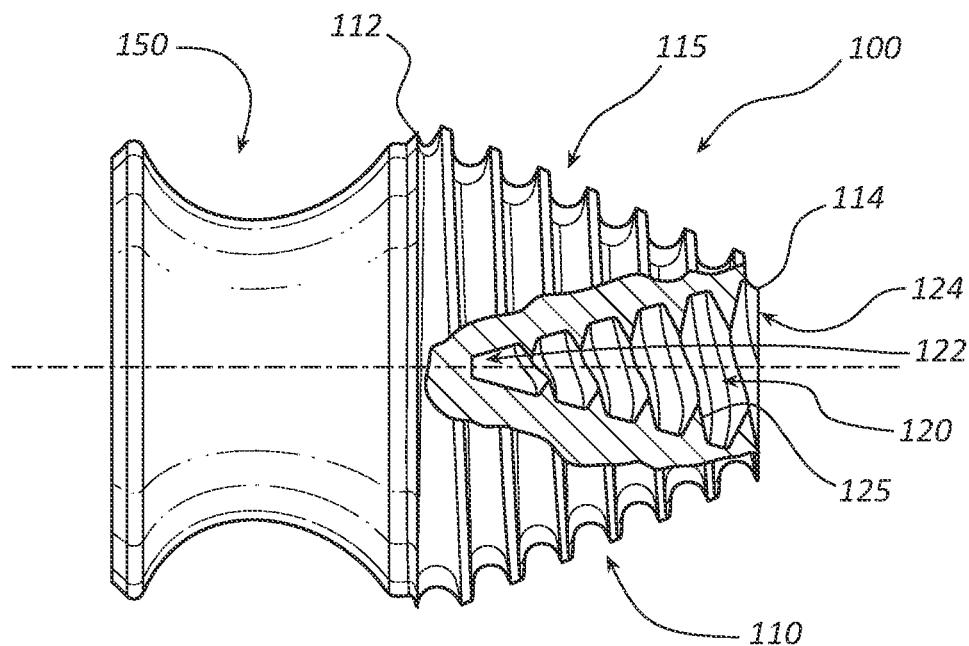
FIG. 1B is a cutaway, perspective view of the vertebral bone anchor of FIG. 1A.

FIGS. 1A and 1B depict an example of a bone anchor or implant 100 according to some embodiments. Bone anchor 100 comprises a bone engagement portion 110 that comprises an exterior surface that is tapered from the proximal end 112 to the distal end 114 such that the distal end 114 is narrower than the proximal end 112. In preferred embodiments, the angle of this taper may range from about 1 degree to about 20 degrees. In some such embodiments, the angle of this taper may range from about 5 degrees to about 10 degrees. In some embodiments, the exterior surface of the bone engagement portion of bone anchor 100 may define a conical or frusto-conical shape.

The exterior surface of bone engagement portion 110 further comprises a thread form 115, such as preferably a thread form having a relatively wide and/or deep thread configured for engagement with cancellous bone, such as the cancellous bone inside the cortical wall of a vertebrae. As discussed and, in some cases, depicted in connection with embodiments referenced below, such thread form 115 may comprise any suitable thread form, such as a single thread, a dual-lead thread, a triple-lead thread, and the like. As also discussed in greater detail below, in some embodiments, thread form 115 may vary throughout the form, such as by increasing and/or decreasing in pitch or depth from the proximal end 112 to the distal end 114.

Bone anchor 100 further comprises an inner chamber 120. Inner chamber 120 may be defined by an inner surface that, like the outer surface of bone engagement portion 110, also tapers. However, in preferred embodiments, inner chamber 120 tapers in the opposite direction relative to the outer surface of bone engagement portion 110. Thus, as shown in the cutaway view of FIG. 1B, chamber 120 tapers from its proximal end 122 to its distal end 124, which distal end 124 coincides with the distal end 114 of the entire bone engagement portion 110 in the depicted embodiment, such that the proximal end 122 of the inner chamber 120 is smaller in diameter and/or another suitable dimension than the distal end 124 of chamber 120. In preferred embodiments, the angle of this inner taper to chamber 120 may range from about 1 degree to about 20 degrees. In more preferred embodiments, the angle of this inner taper to chamber 120 may range from about 5 degrees to about 10 degrees.

Preferably, the length of the inner chamber 120 is greater than about 50% of the length of bone engagement portion 110 and/or thread form 115. In some embodiments, the length of the inner chamber 120 may be between about 10% and about 100% of the length of bone engagement portion 110 and/or thread form 115. In some such embodiments, the length of the inner chamber 120 may be between about 30% and about 100% of the length of bone engagement portion 110 and/or thread form 115. In some such embodiments, the length of the inner chamber 120 may be between about 50% and about 80% of the length of bone engagement portion 110 and/or thread form 115.

Inner chamber 120 is preferably configured to do one or more of actively engage and draw bone or other tissue into chamber 120, provide a differential in force and/or surface tension between the inner and outer surfaces of the implant, and compress the bone/tissue as it is being drawn into the chamber 120. The reverse taper of the inner chamber 120 previously discussed may provide for compression of the bone/tissue as it is introduced into the chamber by threading the exterior thread form 115 into the bony tissue.

As another possible feature that may serve to actively engage and draw bone or other tissue into chamber 120 and/or provide a differential in force and/or surface tension between the inner and outer surfaces of the implant 100, chamber 120 preferably also comprises a thread form 125. As with external thread form 115, internal thread form 125 may comprise any suitable thread form, such as a single thread, a dual-lead thread, a triple-lead thread, etc., and may vary along the form, such as by increasing and/or decreasing in pitch or depth from the proximal end 122 to the distal end 124. Internal thread form 125, along with any of the other similar thread forms disclosed herein, may terminate prior to the proximal end of the chamber 120 so as to provide an unthreaded chamber at the end. Similarly, the internal thread form 125 may vary from one location to another, such as by providing a tapering thread form, reversing direction, increasing or decreasing in depth, pitch, etc. For example, the internal thread form may, similar to the internal vs. external thread forms, comprise opposing forces and/or adjacent features that are opposed to one another to enhance bone compaction and/or provide other benefits.

In particularly preferred embodiments, thread form 115 may differ from thread form 125, which may further contribute to one or more of these features to improve functionality. For example, thread form 125 may comprise a different pitch, a different depth, a different number of leads, and/or a different thread type relative to thread form 115. Other examples are providing a thread form 125 that varies in pitch and/or depth in a different direction, or to a different degree, relative to thread form 115. Again, this differential may contribute to a differential in force and/or tension that may improve bone healing, anchor stability, and/or provide other improvements. Although providing internal thread form 125 is preferred for these purposes, it is contemplated that, in alternative embodiments, inner chamber 120 may instead comprise other surface features, such as spikes, barbs, or other protrusions, grooves, and/or the like, that are configured to engage and/or draw in bone or other tissue. In some embodiments general surface roughening may even be useful for one or more of these purposes.

In certain preferred embodiments, thread form 125 has a greater thread depth along at least a portion of the thread form 125 (in some such embodiments, along the entire thread form 125) than the thread depth along at least a portion of thread form 115 (again, in some embodiments, along the entire thread form 115). In some such embodiments, for example, the depth of thread form 125 may be, along at least a portion thereof, between about 5 and about 50% greater than the depth of thread form 115 along at least a portion thereof. The depth of thread form 125 may vary, for example, between about 1 and about 5 mm in some embodiments.

Anchor 100 further comprises an engagement member 150 positioned at its proximal end. Engagement member 150 in the depicted embodiment comprises an annular groove that may be configured to engage a ligament or other flexible member that may also engage another anchor (not shown) to span multiple vertebrae and allow for introduction of a correctional force for correction of scoliosis or another spinal deformity. Of course, the annular groove shown in FIGS. 1A and 1B may be replaced with any of a variety of other engagement members available to those of ordinary skill in the art that would allow for application of a force between two or more anchors to apply such a correctional force using a ligament, rod, or other coupling member. Examples of such alternative engagement members include a tulip, clamp, post, hole, slot, and the like, some of which are discussed below in connection with other figures. Any of these engagement members, including engagement member 150, should be considered examples of means for engaging a ligament to impart a force to a vertebral body or other tissue or anatomical feature.

Figure 2A:
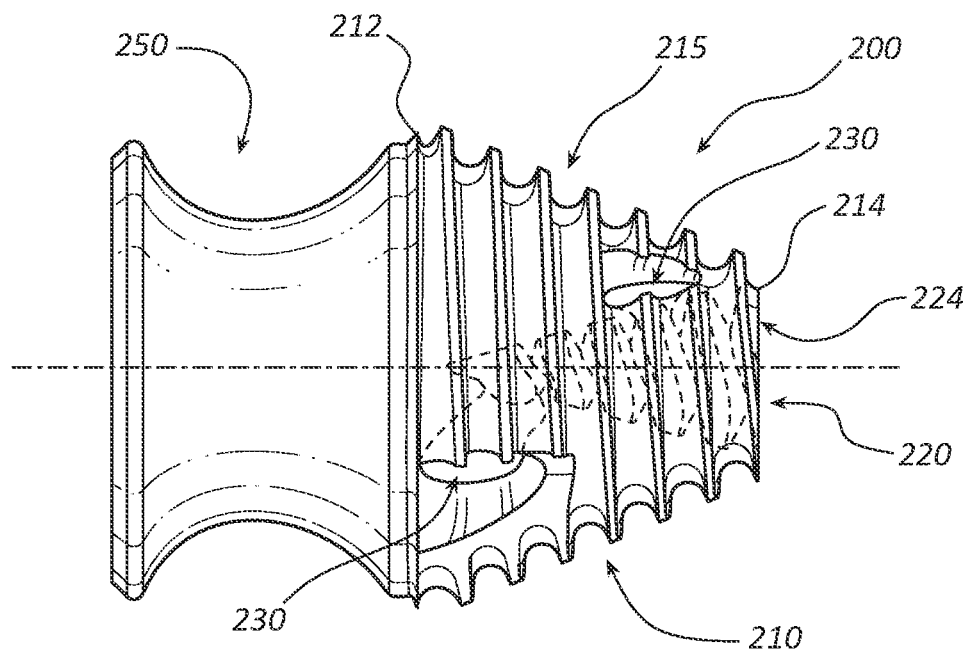
FIG. 2A is a perspective view of a vertebral bone anchor according to other embodiments.
Figure 2B:
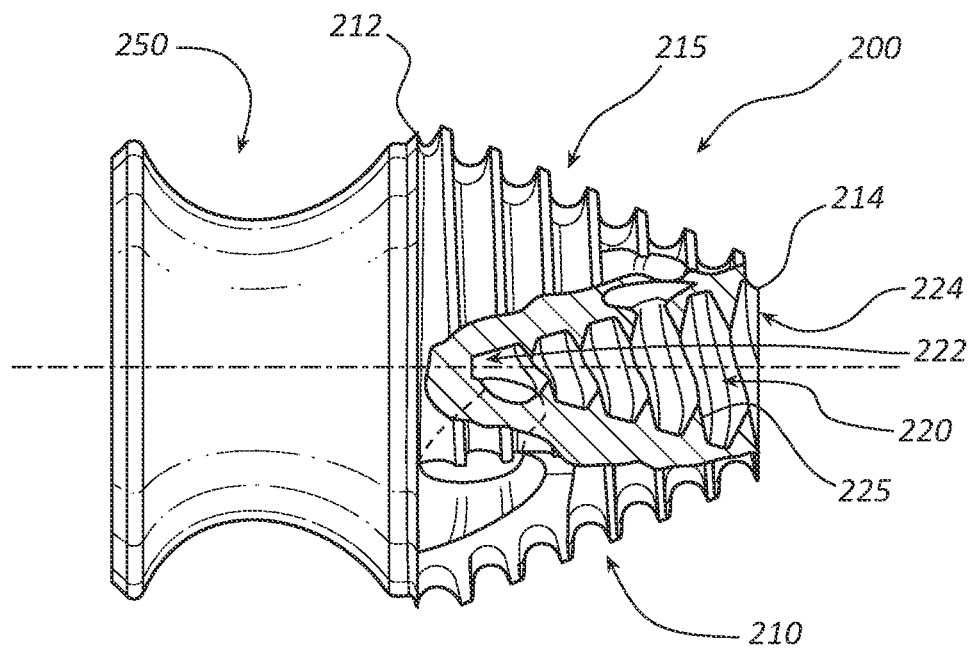
FIG. 2B is a cutaway, perspective view of the vertebral bone anchor of FIG. 2A.

FIGS. 2A and 2B depict another embodiment of an anchor 200. Like anchor 100, anchor 200 comprises a bone engagement portion having an exterior surface that is tapered from the proximal end 212 to the distal end 214 such that the distal end 214 is narrower than the proximal end 212. Similarly, the exterior surface of bone engagement portion further comprises a thread form 215. Again, in some embodiments, thread form 215 may vary throughout the form, such as by increasing and/or decreasing in pitch or depth from the proximal end 212 to the distal end 214.

Bone anchor 200 also further comprises an inner chamber 220 defined by an inner surface that tapers, preferably in an opposite direction relative to the outer surface of the bone engagement portion of anchor 200. The other dimensions, configurations, and options referenced above in connection with bone anchor 100 may also apply to bone anchor 200.

Thus, once again, inner chamber 220 is preferably configured to do one or more of actively engage and draw bone or other tissue into chamber 220, provide a differential in force and/or surface tension between the inner and outer surfaces of the anchor 200, and compress the bone/tissue as it is being drawn into the chamber 220, which may be accomplished by the reverse taper of the inner chamber and/or the internal thread form 225. As with thread forms 115/125, thread form 215 may differ from thread form 225, which may further contribute to one or more of these features to improve functionality.

In some embodiments, it may be desirable to create a force differential along one or more of the thread forms, such as, for example, by providing an external thread form that differs in pitch or otherwise along the length of the thread form. Similarly, it may be desirable to provide a force differential along the internal thread form by, for example, altering the internal thread form, by way of pitch, depth, etc., from one end of the thread form to the other, or by providing distinct, spaced apart thread forms on the inner and/or outer surfaces of the implant.

Anchor 200 further comprises an engagement member 250 defining an annular groove that may be configured to engage a ligament or other flexible member that may also engage another anchor (not shown) to span multiple vertebrae and allow for introduction of a correctional force for correction of scoliosis or another spinal deformity.

Unlike anchor 100, however, anchor 200 comprises a plurality of tunnels 230 and/or openings that extend from the exterior surface of anchor 200 to the inner chamber 220. These tunnels 230 may comprise sharpened and/or beveled edges to further facilitate drawing of bone material into chamber 220 as anchor 200 is advanced through a vertebral body.

Figure 3A:
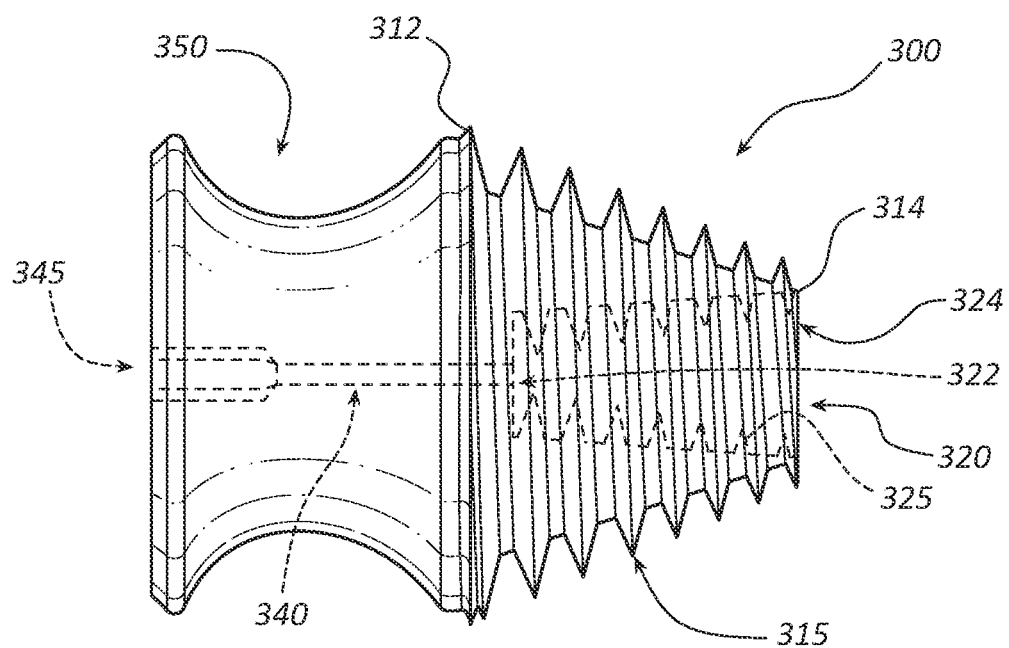
FIG. 3A is a perspective view of a vertebral bone anchor according to still other embodiments.

FIG. 3A depicts another embodiment of an anchor 300. Like anchors 100 and 200, anchor 300 again comprises a bone engagement portion comprising a thread form 315 and having an exterior surface that is tapered from the proximal end 312 to the distal end 314 such that the distal end 314 is narrower than the proximal end 312. Again, in some embodiments, thread form 315 may vary throughout the form, such as by increasing and/or decreasing in pitch or depth from the proximal end 312 to the distal end 314.

Bone anchor 300 also comprises an inner chamber 320 defined by an inner surface that tapers, preferably in an opposite direction relative to the outer surface of bone engagement portion. Chamber 320 is shown having a wider proximal end 322 than bone anchors 100 and 200. The other dimensions, configurations, and options referenced above in connection with bone anchors 100 and 200 may also apply to bone anchor 300.

Thus, once again, inner chamber 320 is preferably configured to do one or more of actively engage and draw bone or other tissue into chamber 320, provide a differential in force and/or surface tension between the inner and outer surfaces of the anchor 300, and compress the bone/tissue as it is being drawn into the chamber 320, which may be accomplished by the reverse taper of the inner chamber and/or the internal thread form 325. Once again, thread form 315 also preferably differs from thread form 325, which may further contribute to one or more of these features to improve functionality.

Anchor 300 further comprises an engagement member 350 defining an annular groove that may be configured to engage a ligament or other flexible member that may also engage another anchor (not shown) to span multiple vertebrae and allow for introduction of a correctional force for correction of scoliosis or another spinal deformity.

Unlike anchors 100 and 200, anchor 300 further comprises a channel 340 or cannulation that terminates in the proximal end of anchor 300. Channel 340 may be configured to receive a tool or portion of a tool and may facilitate introduction/implantation of anchor 300, such as a probe or guidewire. Thus, channel 340 may extend into chamber 320 so that a tunnel, which may be defined in part by channel 340 and in part by chamber 320, extends through the entire length of anchor 300 along its axis. In the depicted embodiment, a keyed tool recess 345 may be formed along the proximal portion of channel 340, which may be configured to receive a driver or other keyed male instrument for rotation/driving of anchor 300. Of course, in other embodiments, channel 340 need not extend the full length of anchor 300.

Figure 3B:
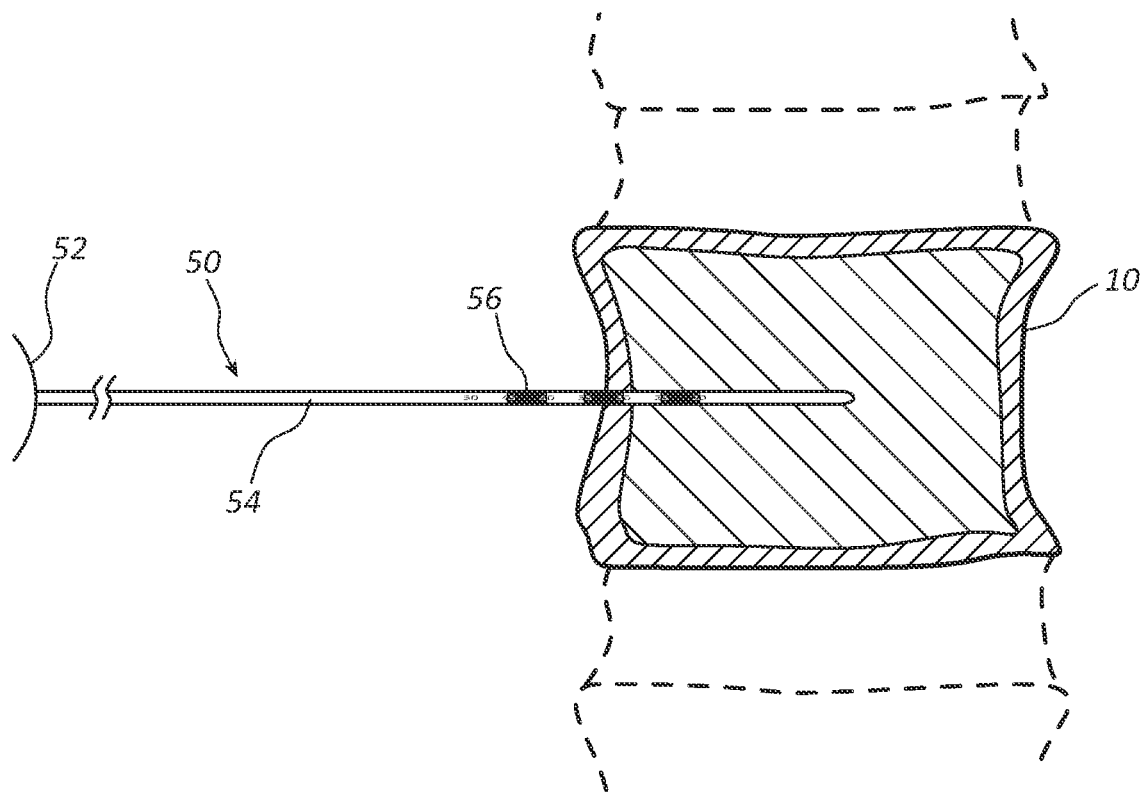
FIG. 3B is a cross-sectional view of a vertebral probe preparing a vertebral body for receipt of a bone anchor therein.

A preferred methodology for installing anchor 300 is depicted in FIGS. 3B-3E. Thus, as shown in FIG. 3B, a probe 50 may initially be inserted through the cortical wall of vertebral body 10 to establish a preferred path for insertion of anchor 300 therein. Probe 50 may comprise a handle or head 52 that, in some embodiments, may be removable from the shaft 54 of probe 50. In some such embodiments, head 52 may be slidably received over the proximal end of shaft 54 to allow for application of a distal force to insert probe 50 through the proximal cortical wall of vertebrae 10 but then allow for removal of head 52 by withdrawing head 52 proximally. In some embodiments, probe 50 may comprise a tip and/or other feature described in U.S. Provisional Patent Application No. 62/712,158, which was filed on Jul. 30, 2018, and titled "Vertebral Probes and Related Surgical Methods," which is hereby incorporated by reference herein in its entirety.

Shaft 54 may comprise a series of markings 56 configured to further facilitate ease of use, safety, and/or subsequent screw/anchor placement. More particularly, shaft 54 may comprise a series of alternating markings 56, which may include alphanumerical markings, dash lines, colors, patterns, etc. In some embodiments, a series of adjacent sections comprising distinct markings of one or more types may be provided. By varying the sections in this manner, a surgeon may be provided with a more general view, once the surgeon becomes familiar with the marking system, of the probe 50 placement without having to rely on specific alphanumerical markings. Of course, those of ordinary skill in the art will appreciate a variety of alternative configurations to allow a surgeon to visualize an approximate location of a vertebral probe within a vertebral body without requiring precise numerical measurements and/or tick marks/dash lines.

Figure 3C:
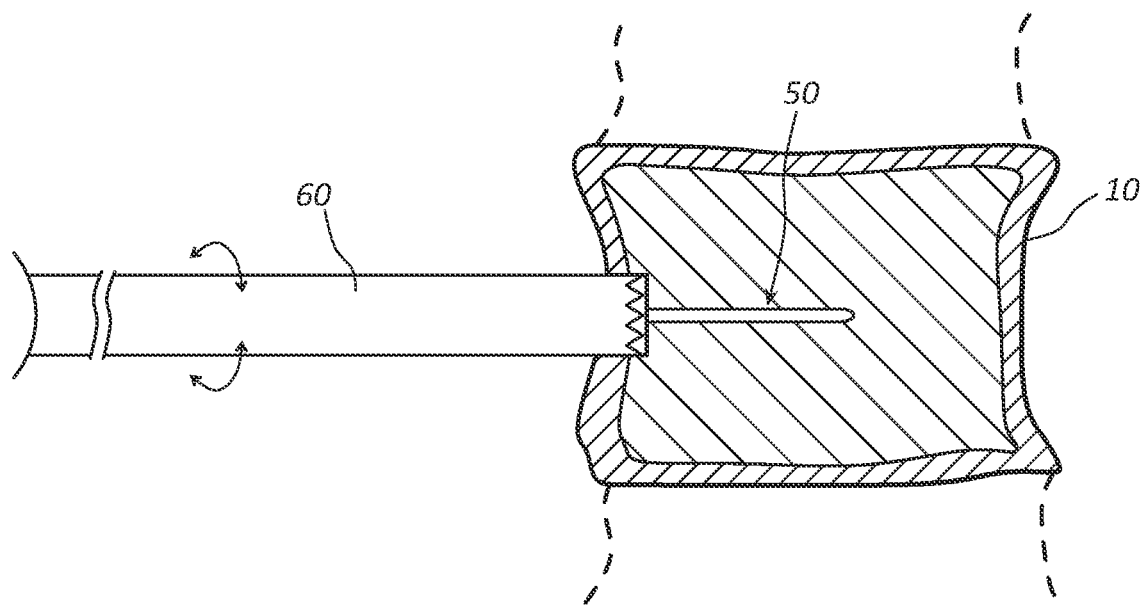
FIG. 3C is a cross-sectional view of a tap that may be slidably received over the vertebral probe or a guidewire to create a starter hole and/or otherwise further prepare the vertebral body for receipt of the bone anchor.

After establishing a desired path within vertebrae 10, head 52 may be removed and, in some embodiments and implementations, a secondary tool, such as a bone screw tap 60 comprising a central opening configured to receive shaft 54 of probe 50, may be inserted over probe 50. Tap 60 or another suitable instrument may comprise a distal end having a series of teeth, spikes, threads, or the like to create a divot or starter hole to facilitate insertion of the anchor 300, as shown in FIG. 3C. In some embodiments, the instrument may comprise a rounded tip, a beveled tip, or a tip having a sharp and/or pointed distal end.

Figure 3D:
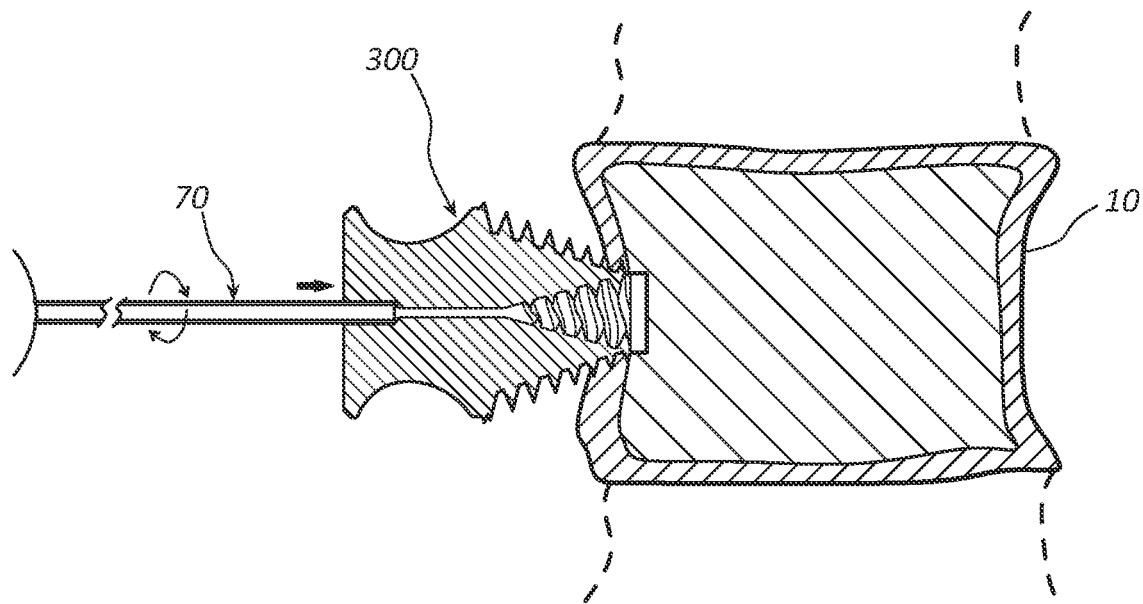
FIG. 3D is a cross-sectional view of the bone anchor of FIG. 3A being inserted into the vertebral body.
Figure 3E:
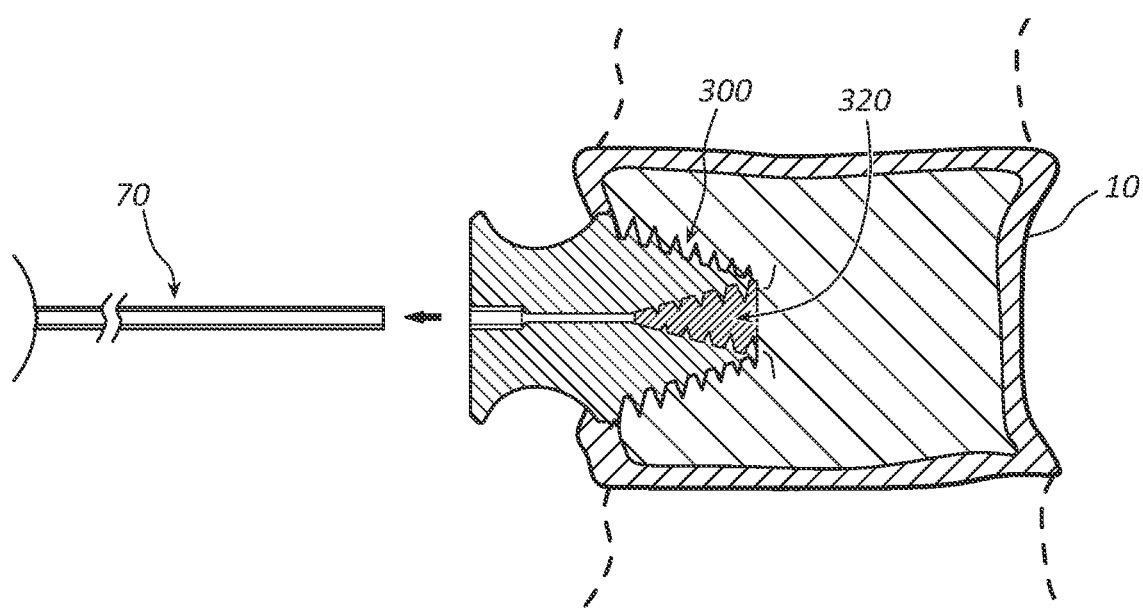
FIG. 3E is a cross-sectional view following insertion of the bone anchor of FIG. 3A into the vertebral body.

Following sufficient preparation of receipt for anchor 300, bone screw tap 60 may be removed from probe 50 (or a guidewire) and anchor 300 may be advanced into place adjacent to the prepared bone entry site over probe 50 or a guidewire (not shown). As shown in FIG. 3D, anchor 300 may then be rotated and/or driven into the vertebrae 10. In some embodiments and implementations, probe 50 may comprise a keyed portion configured to engage keyed recess 345 of anchor 300 such that this device may also be used to drive the anchor. Alternatively, another driver or suitable device may be used for this purpose, such as driver 70 shown in FIG. 3D. Thus, in some embodiments and implementations, probe 50 may be removed prior to advancing anchor 300. As shown in FIG. 3E, implant 300 is driven into vertebrae 10, bone is received and automatically compacted within chamber 320 due to the features previously discussed, including the reverse taper of chamber 320.

Figure 4A:
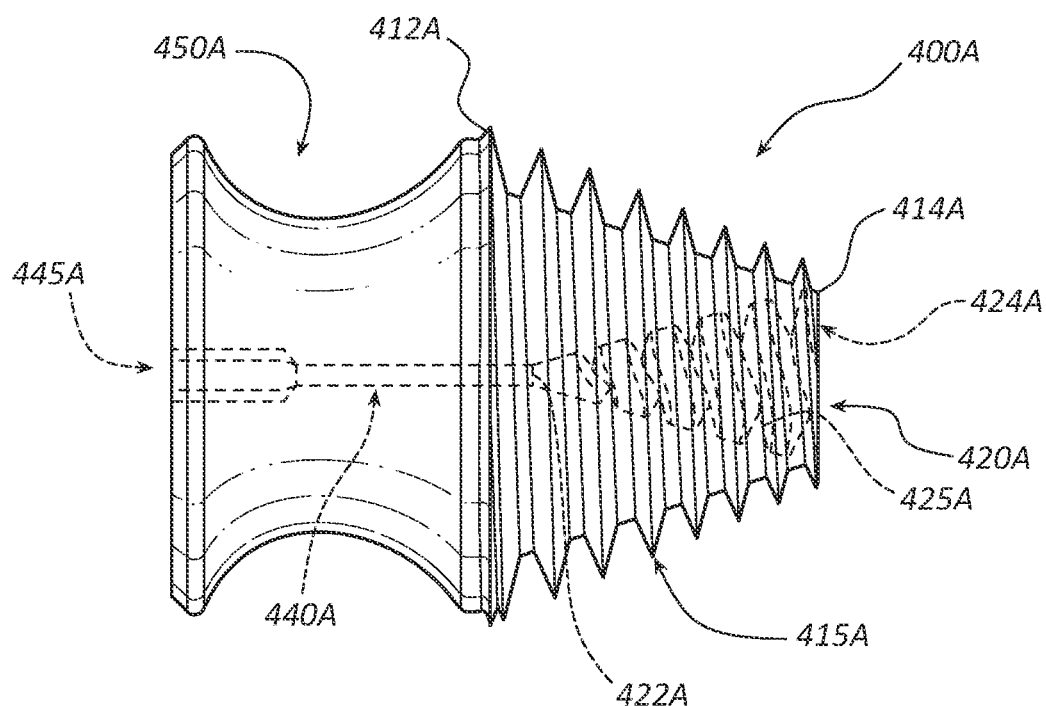
FIG. 4A is a perspective view of a vertebral bone anchor according to still other embodiments.
Figure 4B:
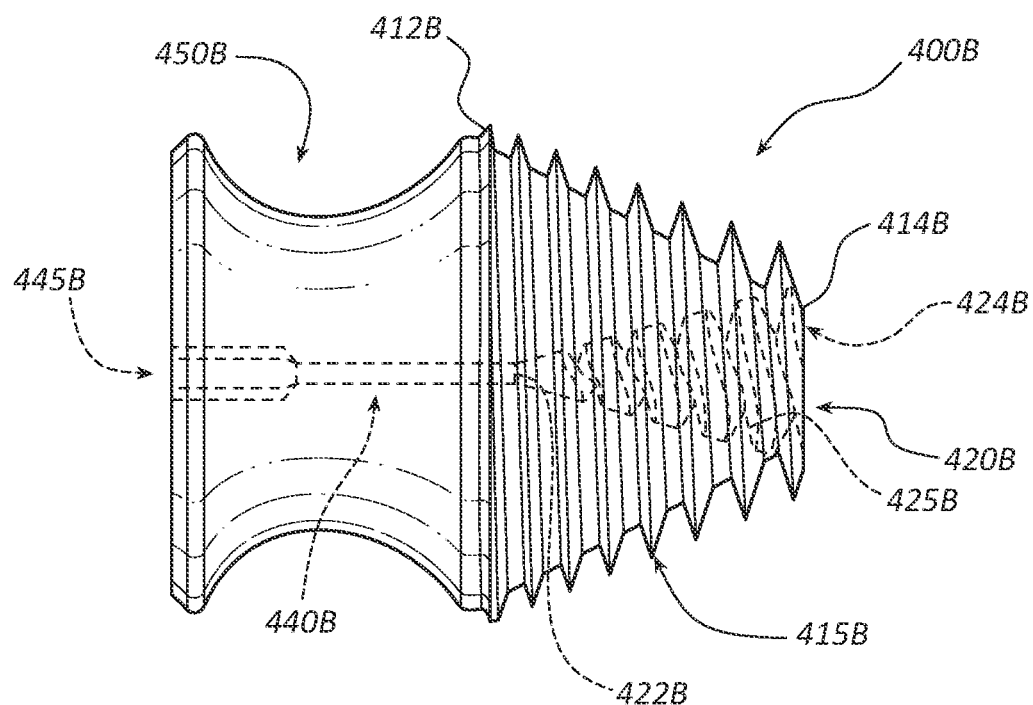
FIG. 4B is a perspective view of a vertebral bone anchor according to further embodiments.

Still other embodiments of bone anchors are shown in FIGS. 4A and 4B at 400A and 400B, respectively. Bone anchors 400A and 400B are similar to the previous bone anchors discussed in connection with previous figures except thread forms 415A/415B gradually differ in thread depth between the proximal ends 412A/412B and the distal ends 414A/414B of their respective anchor. More particularly, thread form 415A defines a thread depth that decreases from the proximal end 412A to the distal end 414A and thread form 415B defines a thread depth that increases from the proximal end 412B to the distal end 414B.

These bone anchors 400A/400B are otherwise similar to the anchors previously discussed and may include, or be modified to omit, any of the features discussed in connection with such anchors. Thus, bone anchors 400A/400B both comprise an inner chamber 420A/420B that preferably tapers in the opposite direction as the exterior surface of the bone engagement portion of the anchor 400A/400B upon which the thread forms 415A/415B are formed such that the proximal portions 422A/422B are smaller in diameter or another dimension than the distal portions 424A/424B, as previously mentioned. In addition, bone anchors 400A/400B further comprise respective second thread forms 425A/425B within chambers 420A/420B, engagement members 450A/450B for engaging ligaments or other engagement bands, a central cannulation 440A/440B, and a keyed feature 445A/445B to facilitate engagement with a driver or other suitable instrument for driving the anchor into a vertebral body or other tissue.

Figure 5A:
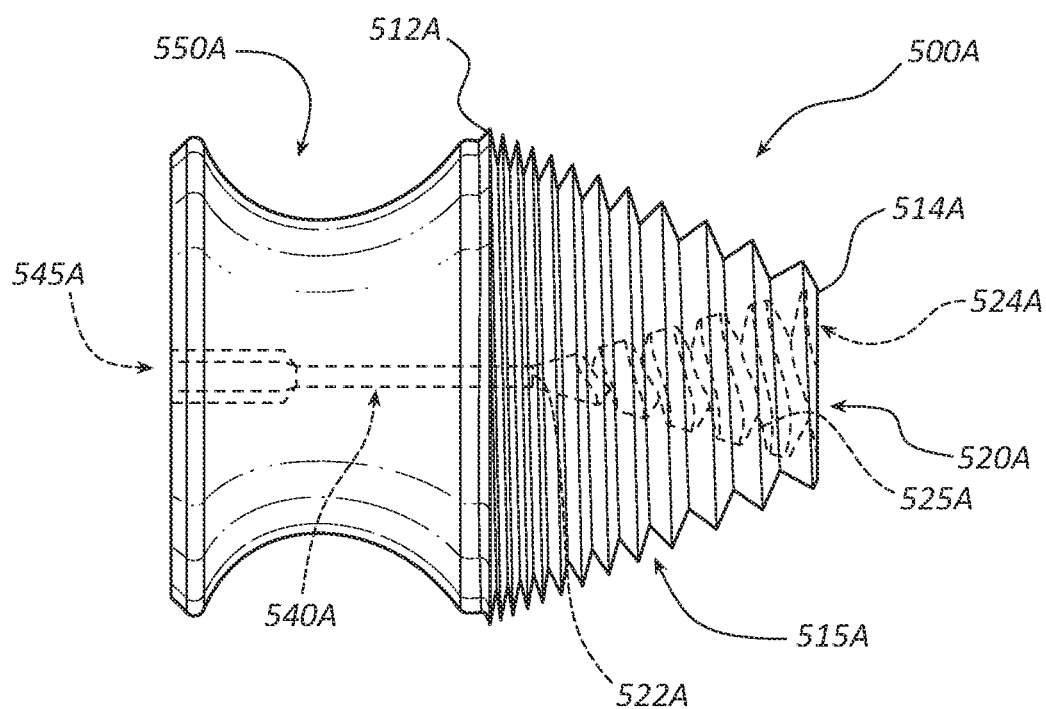
FIG. 5A is a perspective view of a vertebral bone anchor according to still further embodiments.
Figure 5B:
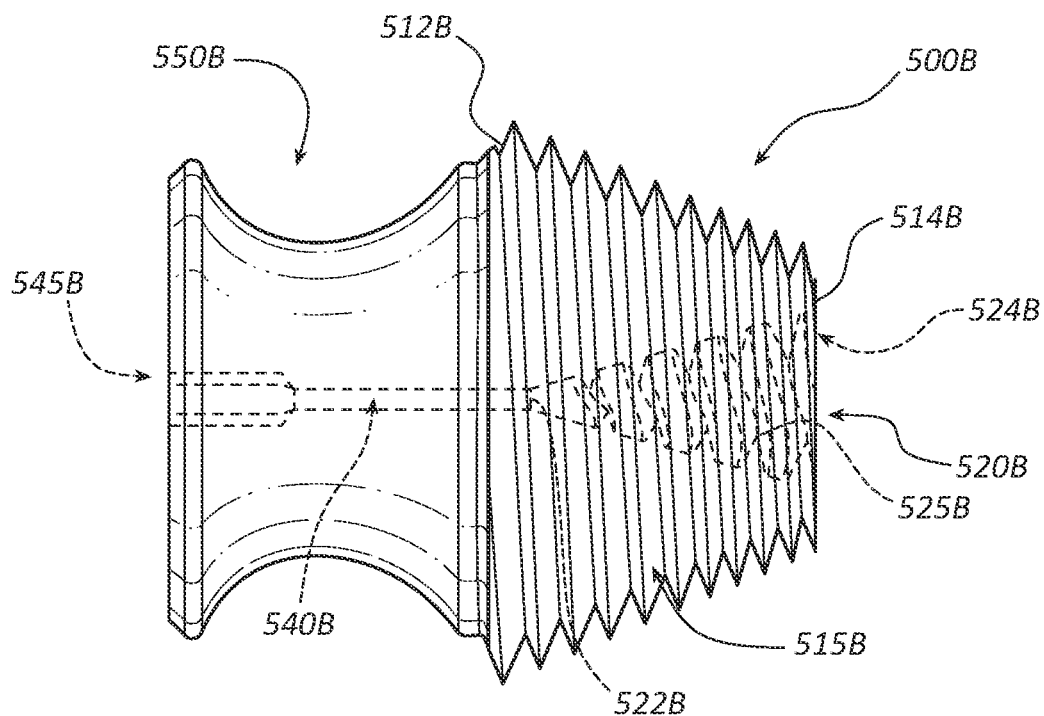
FIG. 5B is a perspective view of a vertebral bone anchor according to additional embodiments.

Additional embodiments of bone anchors are shown in FIGS. 5A and 5B at 500A and 500B, respectively. Once again, bone anchors 500A and 500B are similar to the previous bone anchors depicted except thread forms 515A/515B gradually differ in thread pitch between the proximal ends 512A/512B and the distal ends 514A/514B of a bone engagement region of their respective anchor. More particularly, thread form 515A defines a thread pitch that increases from the proximal end 512A to the distal end 514A and thread form 515B defines a thread pitch that decreases from the proximal end 512B to the distal end 514B.

These bone anchors 500A/500B are otherwise similar to the anchors previously discussed and may include, or be modified to omit, any of the features discussed in connection with such anchors. Thus, bone anchors 500A/500B both comprise an inner chamber 520A/520B that preferably tapers in the opposite direction as the exterior surface of the bone engagement portion of the anchor 500A/500B upon which the thread forms 515A/515B are formed. In addition, bone anchors 500A/500B further comprise respective second, internal thread forms 525A/525B within chambers 520A/520B. These internal thread forms 525A/525B preferably differ in one or more ways relative to external thread forms 515A/515B, such as by providing an increased thread depth, differing pitch, etc. The internal thread forms 525A/525B may also vary between their respective proximal and distal ends, similar to the external thread forms 515A/515B.

Bone anchors 500A/500B further comprise engagement members 550A/550B for engaging ligaments or other engagement bands, a central cannulation 540A/540B, and a keyed feature 545A/545B to facilitate engagement with a driver or other suitable instrument for driving the anchor into a vertebral body or other tissue.

Figure 6:
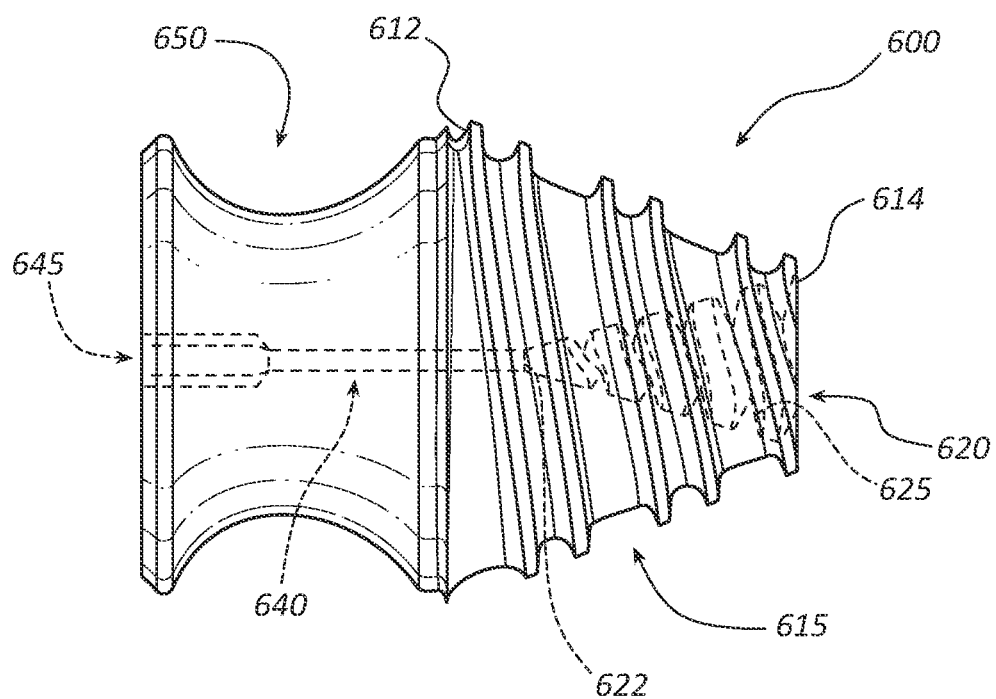
FIG. 6 is a perspective view of a vertebral bone anchor according to still other embodiments.

Yet another alternative embodiment of a bone anchor 600 is depicted in FIG. 6. Bone anchor 600 comprises an external thread form 615 that comprises a dual-lead thread form. Other embodiments may comprise a triple lead thread form. Again, one or more of the previously described features may be included as desired, including an internal chamber 620 comprising an internal thread form 625. Internal thread form 625 may comprise a single, double, or triple lead thread form, or any other suitable thread form. Again, in certain preferred embodiments, internal thread form 625 may differ from external thread form 625 in one or more ways in order to provide a differential in force and/or surface tension between various portions of the anchor 600, such as between the inner and outer surfaces of the implant 600. In the depicted embodiment, anchor 600 further comprises an engagement member 650, a central cannulation for a guide wire, probe, or other instrument, and a keyed feature 645.

Figure 7A:
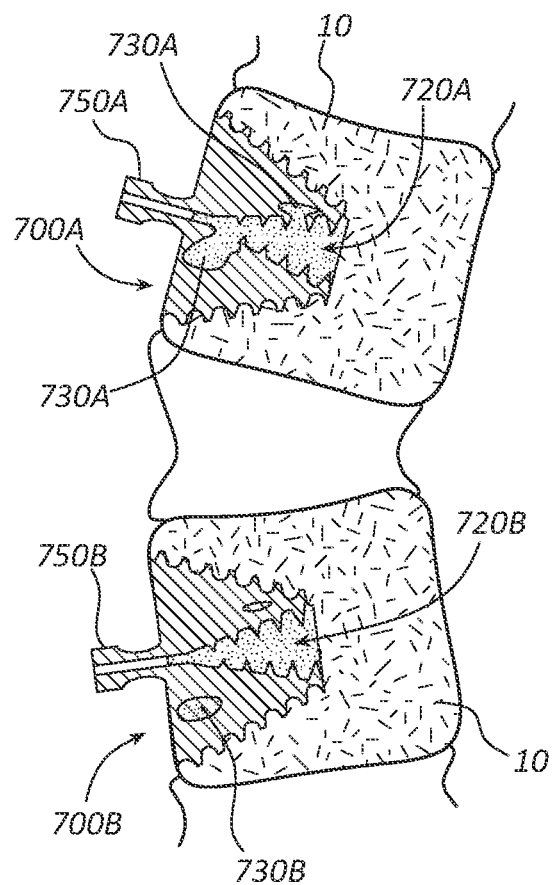
FIG. 7A is a cross-sectional view of a system for spinal deformity correction according to some embodiments shown prior to application of a restorative force via ligaments.
Figure 7B:
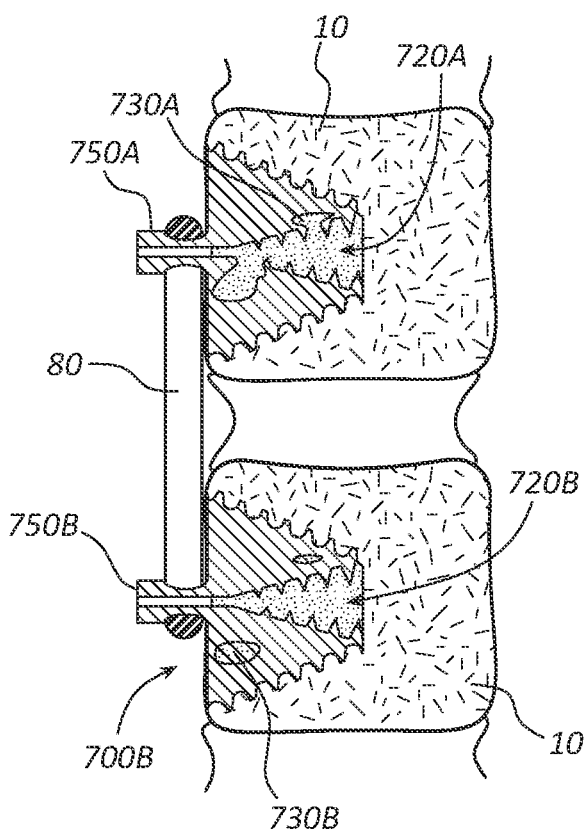
FIG. 7B is a cross-sectional view of a system for spinal deformity correction according to some embodiments shown following application of a restorative force via ligaments.

FIGS. 7A and 7B depict a system for spinal deformity correction comprising two bone anchors 700A/700B each coupled with an adjacent vertebral body 10. As those of ordinary skill in the art will appreciate, any number of bone anchors may be used as desired in accordance with the particular surgical procedure being performed. As shown in FIG. 7B, a loop ligament 80 may be wrapped around respective engagement members 750A/750B of the adjacent anchors 700A/700B to apply a restorative force to a patient's spinal column. Various additional elements, features, and/or methods may be used to increase and/or decrease this force as needed, some of which are discussed below.

As also shown in these figures, bone anchors 700A/700B may each comprise one or more tunnels 730A/730B that may allow for driving additional bone material into inner chambers 720A/720B, as previously described. These tunnels 730A/730B may also allow for an outlet to the pressure that may build up within chambers 720A/720B as bone anchors 700A/700B are driven through the vertebral bone.

Figure 8:
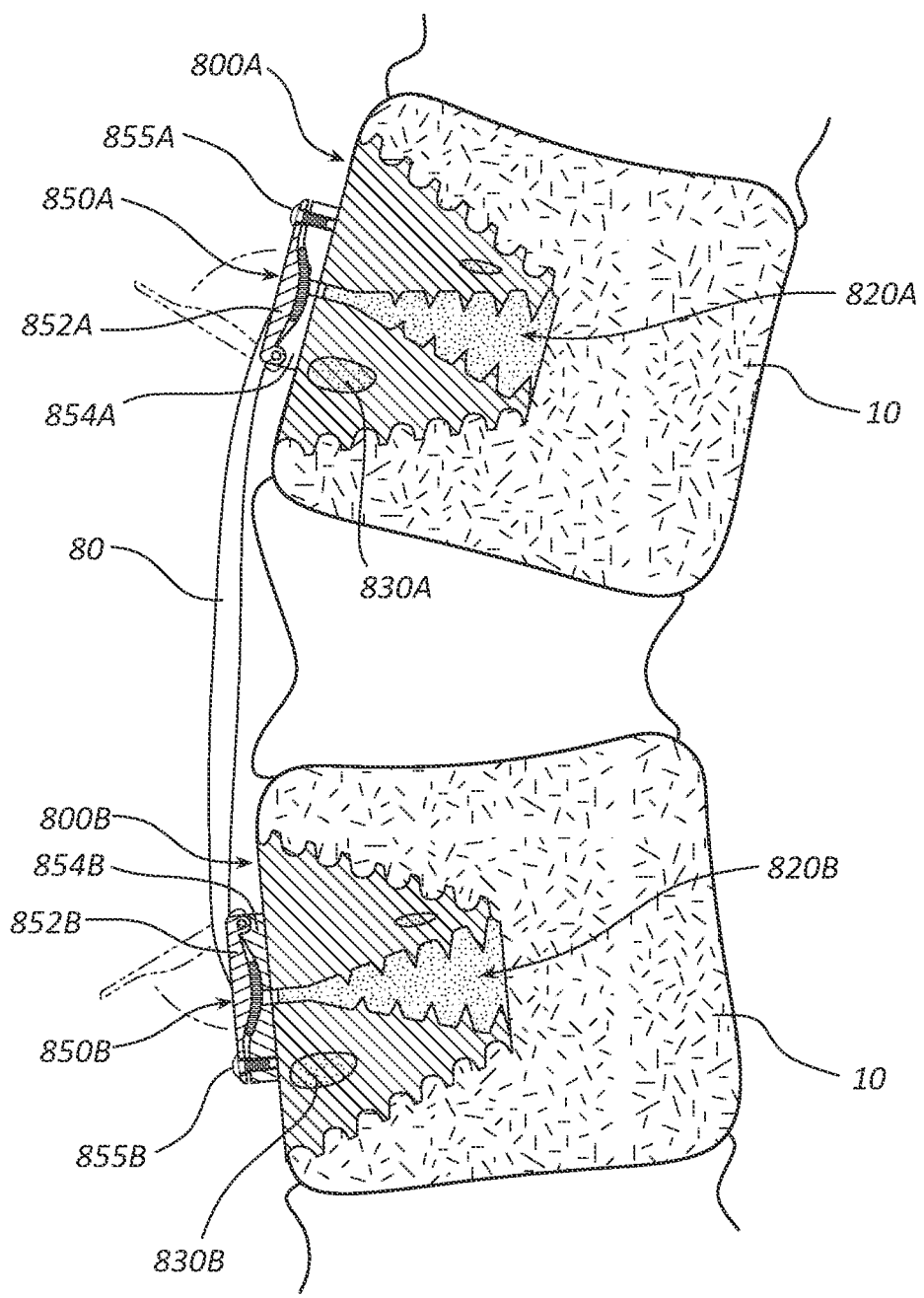
FIG. 8 is a cross-sectional view of a system for spinal deformity correction according to other embodiments.

FIG. 8 depicts still another embodiment of a system for spinal deformity correction. This system again comprises two adjacent bone anchors 800A/800B. These bone anchors 800A/800B again preferably comprise inner chambers 820A/820B that comprise thread forms that may differ from the respective exterior thread forms. Also, one or more tunnels 830A/830B and/or other openings may be formed between the exterior of the bone anchors 800A/800B and the interior of the bone anchors 800A/800B, such as between the inner thread forms and the outer thread forms.

Bone anchors 800A/800B each comprises a distinct type of engagement member 850A/850B. More particularly, engagement members 850A/850B each comprises a clamp defined by a base 854A/854B and a lid 852A/852B that is pivotably coupled to base 854A/854B. A fastener 855A/855B may be used to fix the ligament 80, which may comprise a straight (non-loop) ligament). Thus, the ligament 80 may be clamped at one end or position (associated with one of the two bone anchors 800A/800B) and then inserted through the other clamp/engagement member 850, after which a desired force may be applied to the associated vertebral bodies through ligament 80 and then the opposite end or position may be clamped using the other clamp/engagement member 850.

Preferably, the inner surface of the lid 852 and seat/base 854 are smooth and define a large surface area so as to distribute the force applied to the ligament 80 along a large surface area of the ligament to avoid damage to the ligament 80, as shown in FIG. 8. In some embodiments, clamping force may be applied gradually to ligament 80 so that ligament 80 may be partially clamped using a first force sufficient to keep the ligament in place but allow the ligament 80 to be pulled through engagement members 850A/850B upon application of a threshold larger force. Thus, ligament 80 may be pulled through the clamp defined by the lid 852 and base 854 and then fastener 855 may be further tightened to apply a second, larger locking force that locks the two anchors 800 in place with the desired restoration force. In some embodiments, non-circular ligaments, such as ovoid ligaments, may be used to further enhance this effect if desired. Engagement members 850A and 850B are additional examples of means for engaging a ligament to impart a force to a vertebral body or other tissue or anatomical feature.

Figure 9:
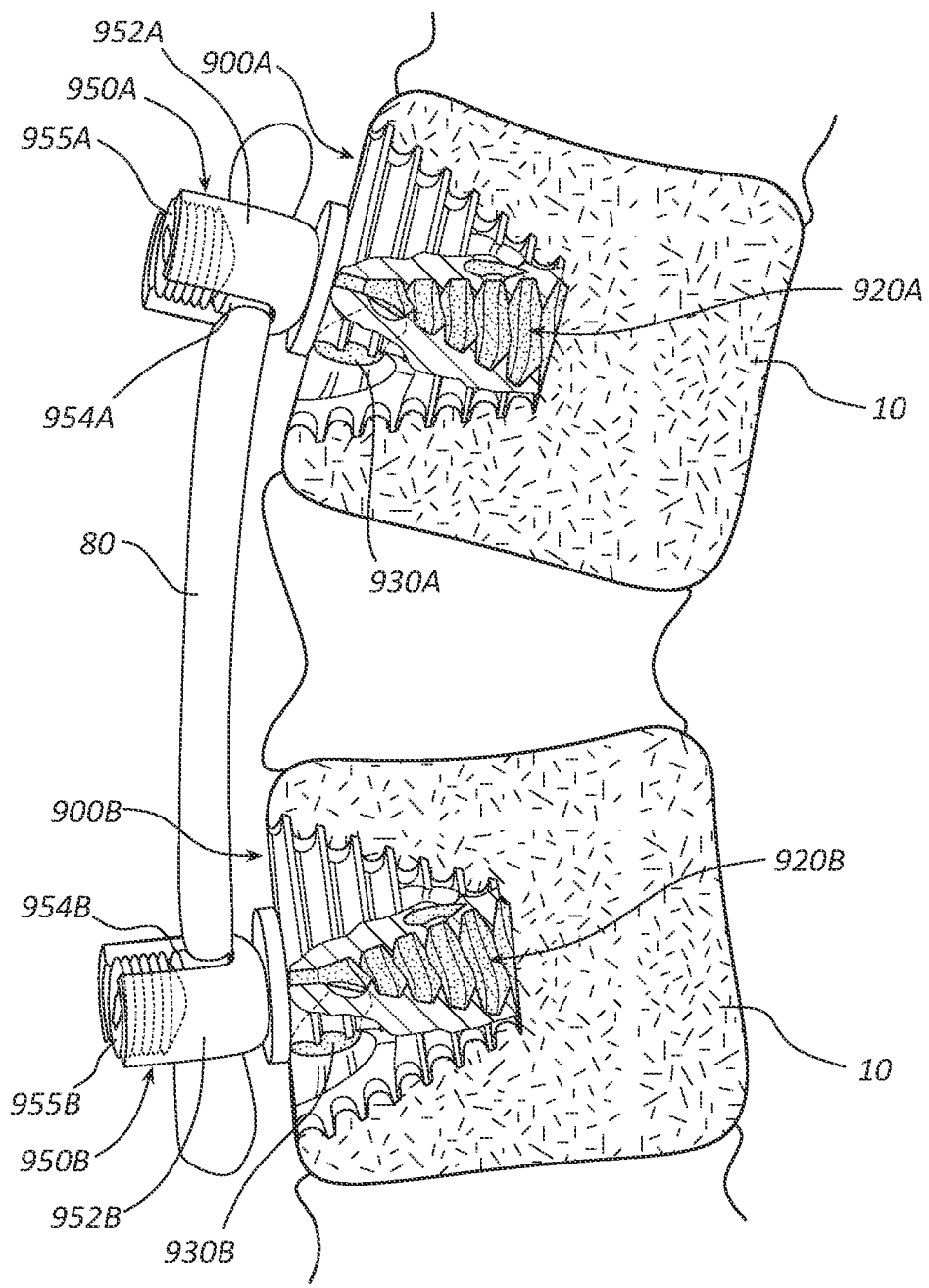
FIG. 9 is a perspective, cutaway view of a system for spinal deformity correction according to still other embodiments.

FIG. 9 depicts yet another embodiment of a system for spinal deformity correction. This system again comprises two adjacent bone anchors 900A/900B that may comprise, or lack if desired, any of the aforementioned features and/or other features available to those of ordinary skill in the art. Thus, bone anchors 900A/900B preferably comprise inner chambers 920A/920B that comprise thread forms that may differ from the respective exterior thread forms, as previously discussed. Also, one or more tunnels 930A/930B and/or other openings may be formed between the exterior of the bone anchors 900A/900B and the interior of the bone anchors 900A/900B, such as between the inner thread forms and the outer thread forms.

Bone anchors 900A/900B each comprises another distinct type of ligament engagement member 950A/950B. More particularly, engagement members 950A/950B each comprises a tulip connector 952A/952B comprising a U-shaped channel configured to receive a ligament 80 or another suitable, preferably flexible, coupling member. Engagement members 950A/950B each further comprises a set screw or cap 955A/955B that is configured to lock the ligament 80 in place within the tulip connector 952A/952B. Due to the flexible nature of the preferred ligaments 80, it may also be desired to provide an intermediary element between the cap 955A/955B and the ligament. Thus, in the depicted embodiment, a saddle 954A/954B is provided. Saddle 954A/954B is configured to distribute the force from the cap 955A/955B about a larger surface area of ligament 80 so as to reduce the possibility of unwanted damage to ligament 80. Notwithstanding the preferable for providing a larger, smoother surface area to reduce damage, it is contemplated that a set screw may be configured to directly contact and lock ligament 80 in place in alternative embodiments.

In some embodiments, the force on ligament 80 may be applied gradually to so that ligament 80 may be partially clamping using a first force sufficient to keep the ligament in place but allow the ligament 80 to be pulled through engagement members 950A/950B upon application of a threshold larger force. Thus, ligament 80 may be pulled through one of the tulip connectors 950 and partially tightened and then later may be further tightened to apply a second, larger locking force that locks the two anchors 900 in place with the desired restoration force. Engagement members 950A and 950B are additional examples of means for engaging a ligament to impart a force to a vertebral body or other tissue or anatomical feature.

Figure 10A:
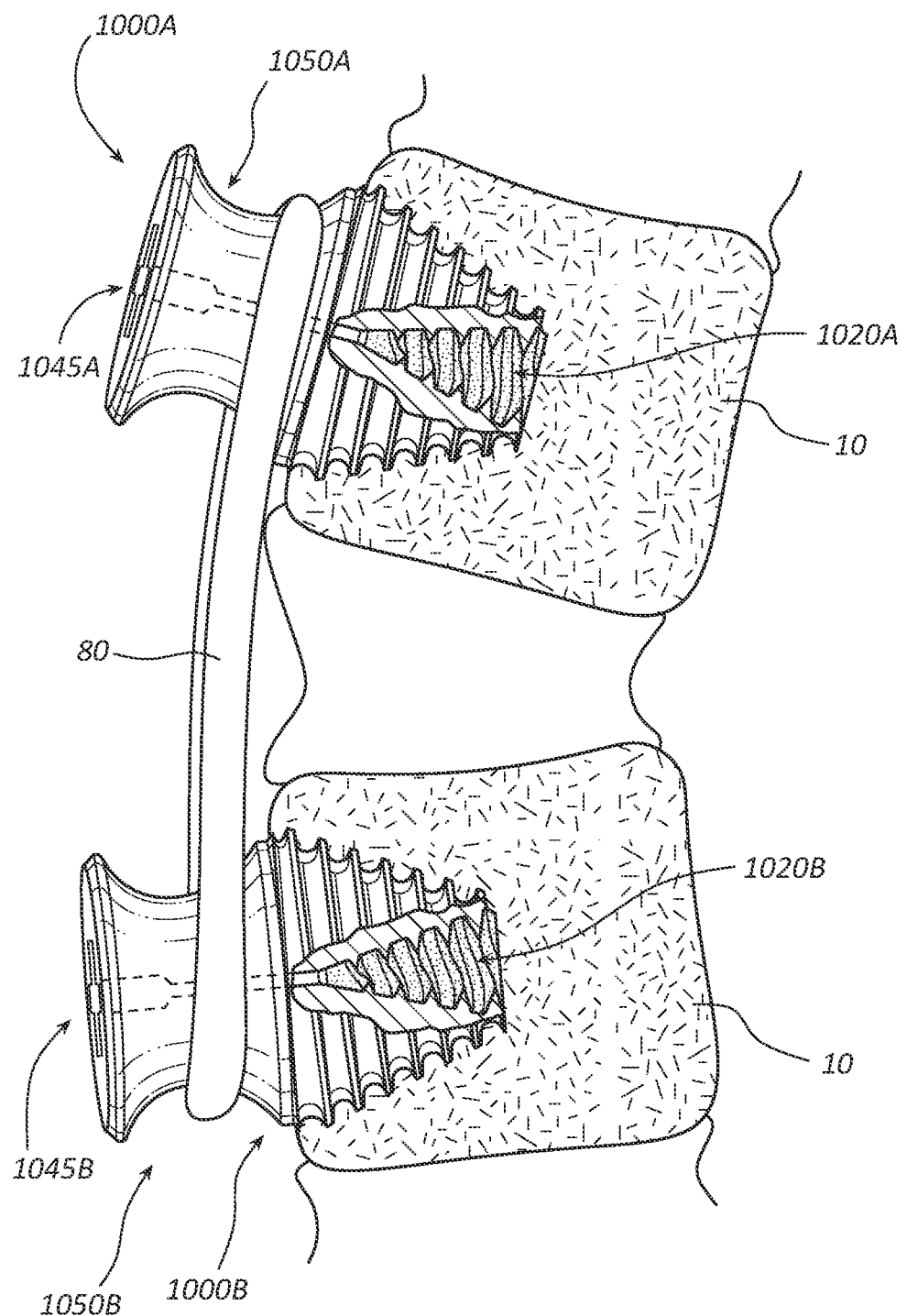
FIG. 10A is a perspective, cutaway view of a system for spinal deformity correction according to further embodiments.
Figure 10B:
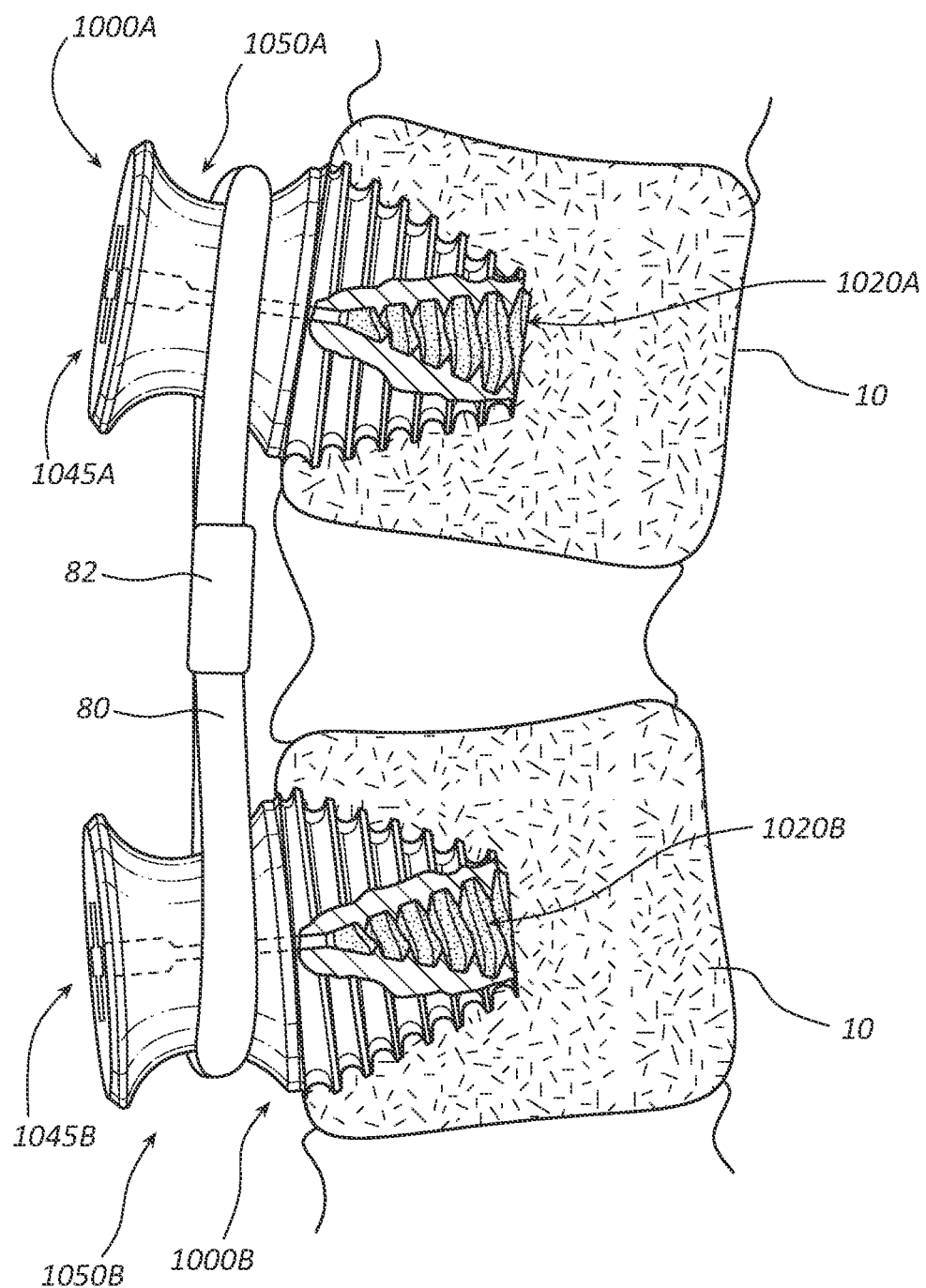
FIG. 10B is a perspective, cutaway view of the system for spinal deformity correction of FIG. 10A following tightening of a loop ligament coupled with two adjacent bone anchors.

FIGS. 10A and 10B depict another embodiment of a system for spinal deformity correction. This system again comprises two or more adjacent bone anchors 1000A/1000B that may comprise, or lack if desired, any of the aforementioned features and/or other features available to those of ordinary skill in the art. Thus, bone anchors 1000A/1000B preferably comprise inner chambers 1020A/1020B that comprise thread forms that may differ from the respective exterior thread forms, as previously discussed. Keyed recesses 1045A/1045B may be provided in a proximal surface of anchors 1000A/1000B to facilitate driving the anchors 1000A/1000B into vertebral bodies 10, as previously discussed.

A loop ligament 80 may be wrapped around respective engagement members 1050A/1050B, as depicted in FIG. 10A. One or more sutures, bands, or other tightening means 82 may then be used to increase the force between anchors 1000A/1000B to apply a restorative force to a spinal column, as depicted in FIG. 10B. As those of ordinary skill in the art will appreciate, any number of such tightening means 82 may be provided as desired to apply forces gradually until the full restorative force desired has been applied.

FIGS. 11A-11D depict various alternative systems for spinal deformity correction. Each of the depicted embodiments may comprise similar anchors, including any of the aforementioned bone anchors. Each of the depicted embodiments may further comprise similar engagement members 1150A/1150B that are coupled to the anchors, such as to a proximal end of the anchors, to facilitate application of a restorative or other desired force. However, the systems depicted in these figures comprise a variety of distinct means for increasing the force between adjacent anchors.

Figure 11A:
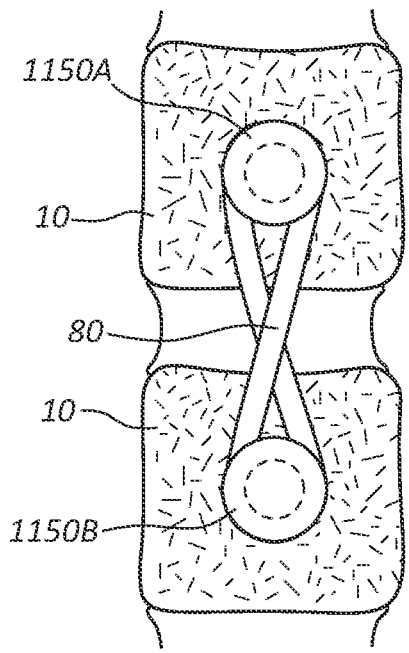
FIGS. 11A-11D depict a variety of alternative means for tightening ligaments to engagement members coupled with bone anchors.

For example, FIG. 11A depicts a loop ligament 80 that is wrapped around adjacent anchors in a figure-8 manner. Thus, the ligament may be coupled to one of the anchors and then rotated any number of times as desired according to the desired force to be applied before being coupled to the opposite anchor.

Figure 11B:
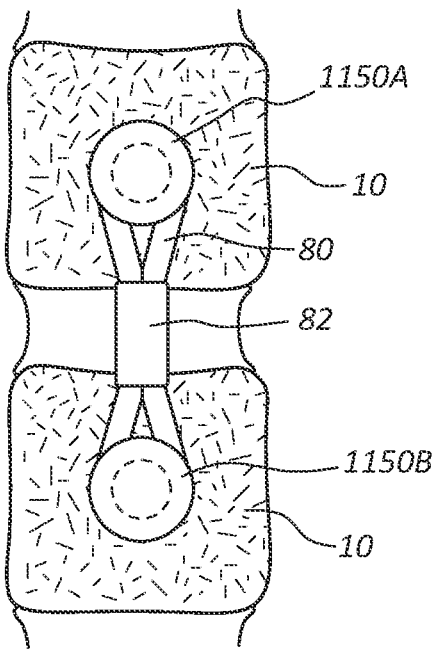

FIG. 11B depicts a system including a means for increasing the force between adjacent anchors that is similar to that depicted in FIG. 10B. Thus, a band 82 may be wrapped around loop ligament 80 at a desired location between adjacent anchors. Band 82 may vary in size according to the desired force to be applied or, as previously mentioned, a plurality of such bands 82 may be used to adjust the force to any desired level.

Figure 11C:
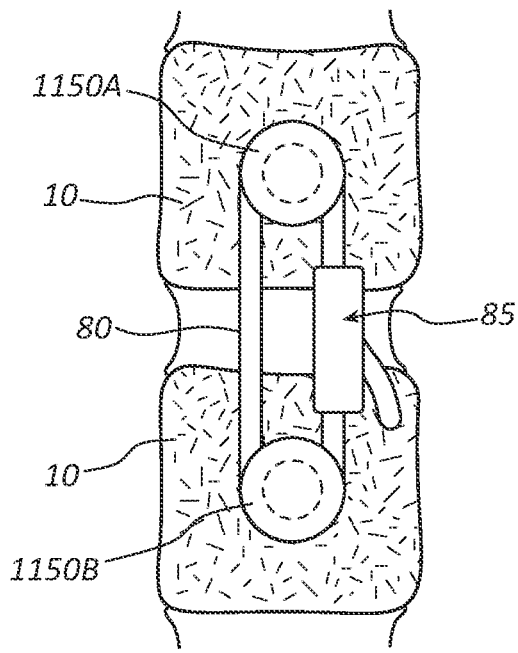

FIG. 11C depicts a straight ligament 80 that may be inserted at opposite ends within a means 85 for increasing the force between adjacent anchors that may comprise, for example, an internal ratchet mechanism that may allow for one end of ligament to be pulled through mechanism 85 to shorten the loop defined thereby without allowing this end to be retracted.

Figure 11D:
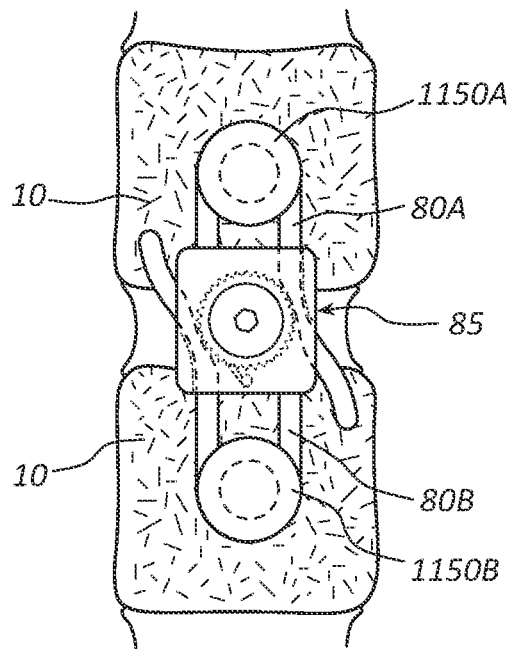

Similarly, FIG. 11D depicts a pair of straight ligaments 80A/80B that may be inserted at opposite ends within another example of a means for increasing the force between adjacent anchors 85. The means 85 for increasing the force depicted in FIG. 11D may allow for one of either of the two opposite ends of ligaments 80A/80B to be pulled through the internal ratcheting mechanism to decrease the length of the defined loop and thereby increase the force being applied to whatever degree of precision required.

Figure 12A:
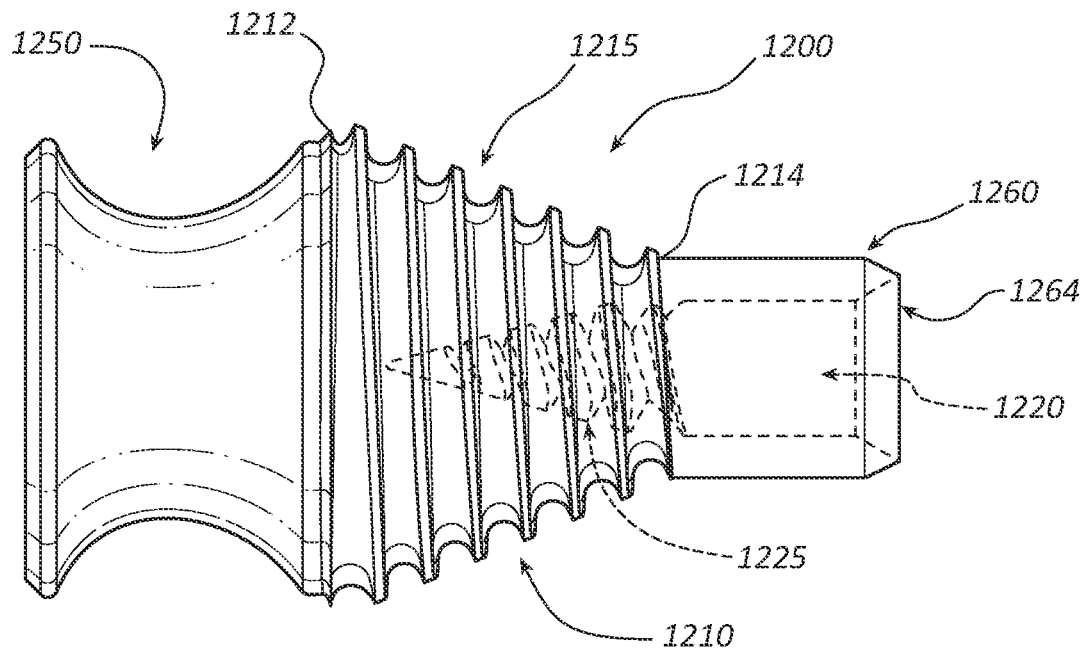
FIG. 12A is a perspective view of a vertebral bone anchor according to additional embodiments.
Figure 12B:
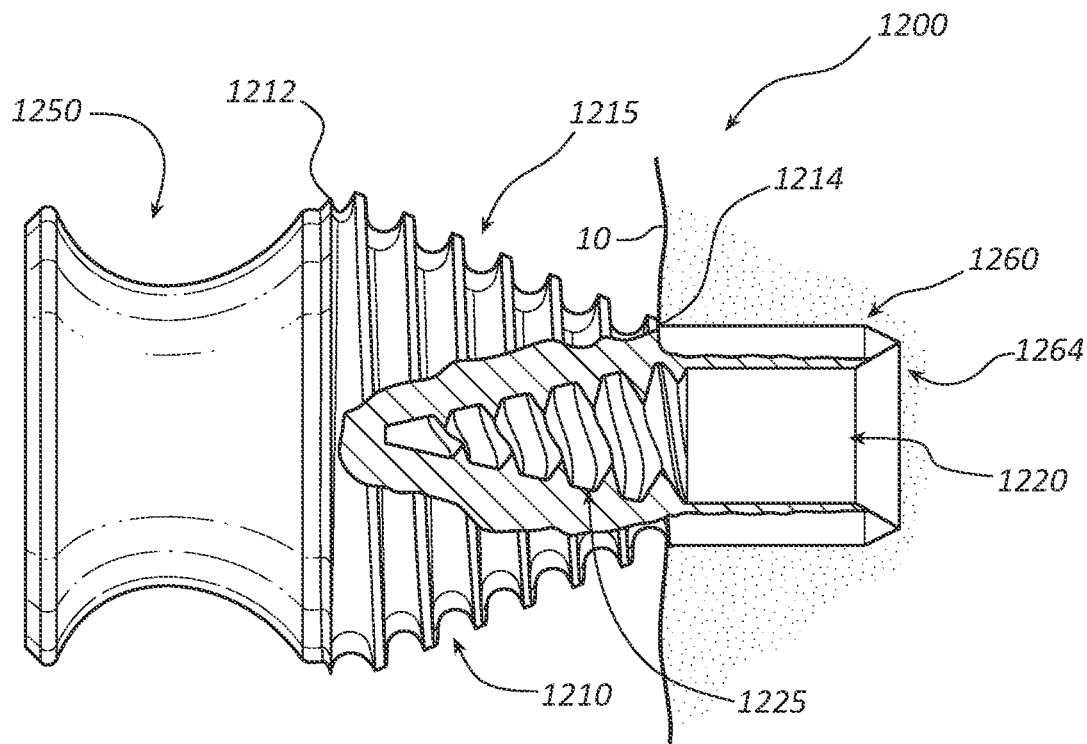
FIG. 12B is a perspective, partial cutaway view of the bone anchor of FIG. 12A being engaged with a vertebral body.

Another example of a bone anchor 1200 is shown in FIGS. 12A and 12B. Bone anchor 1200 is similar to the bone anchors depicted and discussed previously except for the presence of a non-tapering, cylindrical tip 1260. Tip 1260 extends from the distal end 1214 of a tapering portion 1210 (opposite proximal end 1212) and terminates at a preferably sharpened edge 1264 to facilitate penetration into a vertebral body 10 or other bone, as shown in FIG. 12B. In the depicted embodiment, tip 1260 lacks both internal and external threads. As such, bone anchor 1200 may be tamped into the bone before engaging any of the threads. However, in some embodiments, a portion of cylindrical tip 1260, such as preferably a proximal portion, may comprise internal and/or external threads.

It can also be seen that tip 1260 comprises an internal chamber 1220 that extends into the tapering portion. In addition, preferably, at least the proximal portion of chamber 1220 tapers or otherwise varies in size in a direction opposite to the taper of the exterior surface of bone anchor 1200. As previously described, this may allow for bone entering chamber 1220 to be compacted as the anchor 1200 is driven into the bone. In the depicted embodiment, chamber 1220 is cylindrical in shape, similar to the outer surface of tip 1260, along tip 1260 and the reverse tapering of chamber 1220 begins at, or at least substantially at, the distal end 1214 of the tapering section 1210. However, this need not be the case in all embodiments. Indeed, the reverse tapering or other decrease in size of the chamber 1220 from the distal to the proximal end may begin within the cylindrical/non-tapering tip 1260 or may begin proximally of the distal end 1214 of the tapering section.

Otherwise, bone anchor 1200 may be similar to the other anchors depicted in other drawings. For example, the tapering section 1210 may comprise an external thread form 1215 and at least a portion of the inner chamber 1220 may comprise an internal thread form 1225. In some embodiments, the external thread form 1215 may differ from the internal thread form 1225 in one or more ways so as to provide a differential in force between forces generated by the external thread form 1215 on bone adjacent thereto and forces generated by the inner thread form 1225 on bone adjacent thereto. For example, the inner and outer thread forms differ from one another in thread depth, thread direction, number of starts, angle, pitch diameter, major diameter, and/or minor diameter. The internal and/or external thread forms may also vary between their respective proximal and distal ends. In some such embodiments, the internal and/or external thread forms may vary in ways that are different from one another, such as varying along their respective lengths in opposite directions, for example.

Bone anchor 1200 may further comprise an engagement member 1250 for engaging ligaments or other engagement bands, as previously mentioned. One or more of the other features previously described, such as a central cannulation, a keyed feature to facilitate engagement with a driver or other suitable instrument for driving the anchor 1200 into a vertebral body 10 or other tissue, and/or one or more tunnels and/or openings that extend from the exterior surface of anchor 1200 to the inner chamber 1220 may also be provided if desired/useful.

As shown in FIG. 12B, once the non-tapering tip 1260 has been tamped or otherwise inserted into the vertebral body 10, external threads 1215 may be engaged and bone anchor 1200 may be advanced further into the vertebral body 10 by rotation of bone anchor 1200.

Figure 13A:
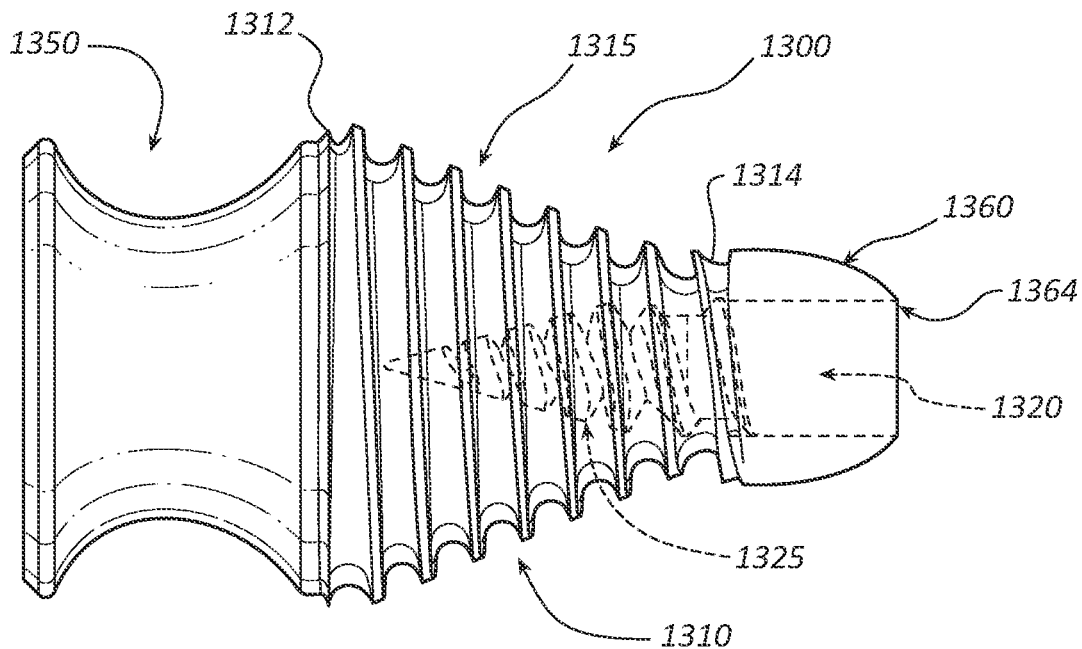
FIG. 13A is a perspective view of a vertebral bone anchor according to further embodiments.
Figure 13B:
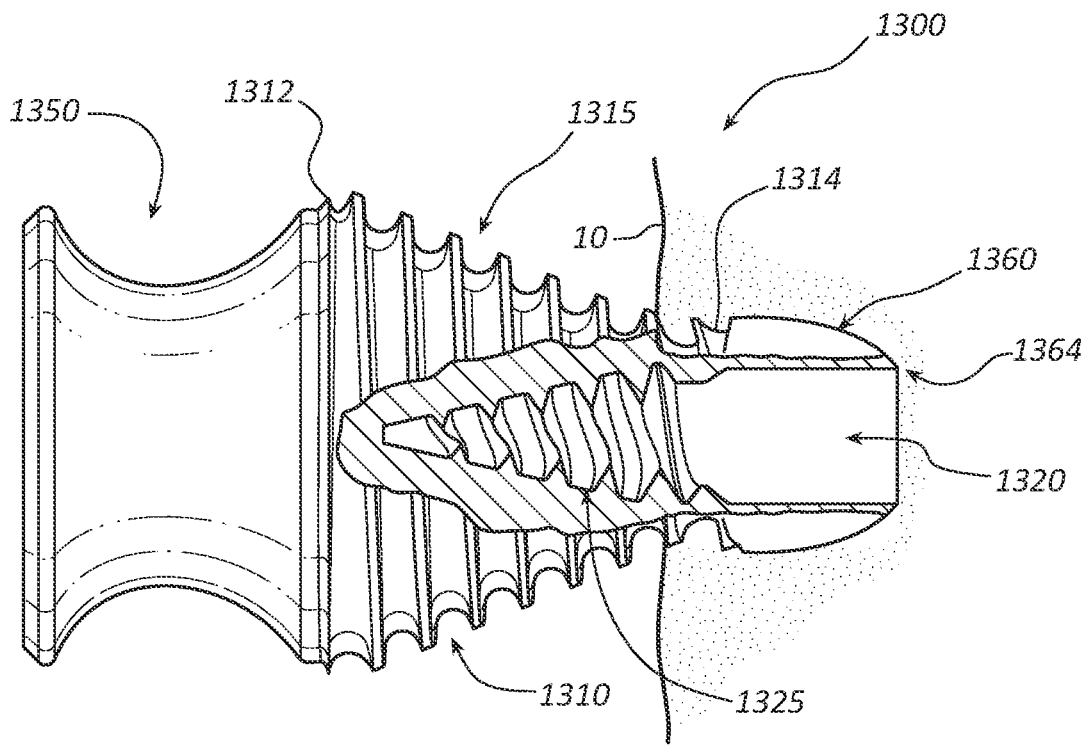
FIG. 13B is a perspective, partial cutaway view of the bone anchor of FIG. 13A being engaged with a vertebral body.

Still another example of a bone anchor 1300 is shown in FIGS. 13A and 13B. Bone anchor 1300 is similar to the bone anchors depicted and discussed previously except for the presence of a tip 1360 that is curved rather than cylindrical as with bone anchor 1200. Tip 1360 extends from the distal end 1314 of a tapering portion 1310 (opposite proximal end 1312) and terminates at a preferably sharpened edge 1364 to facilitate penetration into a vertebral body 10 or other bone, as shown in FIG. 13B. In the depicted embodiment, tip 1360 lacks both internal and external threads. As such, bone anchor 1300 may be tamped into the bone before engaging any of the threads. However, in some embodiments, a portion of cylindrical tip 1360, such as preferably a proximal portion, may comprise internal and/or external threads.

For example, as discussed below in connection with bone anchor 1400, it may be desired in alternative embodiments to begin external thread form 1315 along a proximal portion of tip 1360. As an even more specific example, it may be desired in some embodiments to form threads, which may extend into thread form 1315 continuously in some such embodiments, beginning at or at least substantially at a mid-point of tip 1360 and/or at or at least substantially at the apex of the curve of tip 1360 (the point of the curve furthest from the central axis of the bone anchor 1300).

Tip 1360 further comprises an internal chamber 1320 that extends into the tapering portion. In addition, preferably, at least the proximal portion of chamber 1320 tapers or otherwise varies in size in a direction opposite to the taper of the exterior surface of bone anchor 1300. As previously described, this may allow for bone entering chamber 1320 to be compacted as the anchor 1300 is driven into the bone. In the depicted embodiment, chamber 1320 is cylindrical in shape along tip 1360, similar to the outer surface of tip 1360, and the reverse tapering of chamber 1320 begins at, or at least substantially at, the distal end 1314 of the tapering section 1310. However, this need not be the case in all embodiments. Indeed, the reverse tapering or other decrease in size of the chamber 1320 from the distal to the proximal end may begin within the bowed tip 1360 or may begin proximally of the distal end 1314 of the tapering section. As another alternative, the reverse tapering or other beginning of a decrease in size of the chamber 1320 from distal to proximal may begin at the point at which the external threads begin, which may, as described above, coincide, or at least substantially coincide, with the apex of the curve and/or the midpoint of the tip 1360. In alternative embodiments, tip 1360 may taper to define a conical section rather than a bowed/curved section.

Otherwise, bone anchor 1300 may be similar to the other anchors depicted in other drawings. For example, the tapering section 1310 may comprise an external thread form 1315 and at least a portion of the inner chamber 1320 may comprise an internal thread form 1325. In some embodiments, the external thread form 1315 may differ from the internal thread form 1325 in one or more ways so as to provide a differential in force between forces generated by the external thread form 1315 on bone adjacent thereto and forces generated by the inner thread form 1325 on bone adjacent thereto in any of the ways previously described.

Bone anchor 1300 may further comprise an engagement member 1350 for engaging ligaments or other engagement bands, as previously mentioned. One or more of the other features previously described, such as a central cannulation, a keyed feature to facilitate engagement with a driver or other suitable instrument for driving the anchor 1300 into a vertebral body 10 or other tissue, and/or one or more tunnels and/or openings that extend from the exterior surface of anchor 1300 to the inner chamber 1320 may also be provided if desired/useful.

As shown in FIG. 13B, once the tip 1360 has been tamped or otherwise inserted into the vertebral body 10, external threads 1315 may be engaged and bone anchor 1300 may be advanced further into the vertebral body 10 by rotation of bone anchor 1300, as previously described.

Figure 14A:
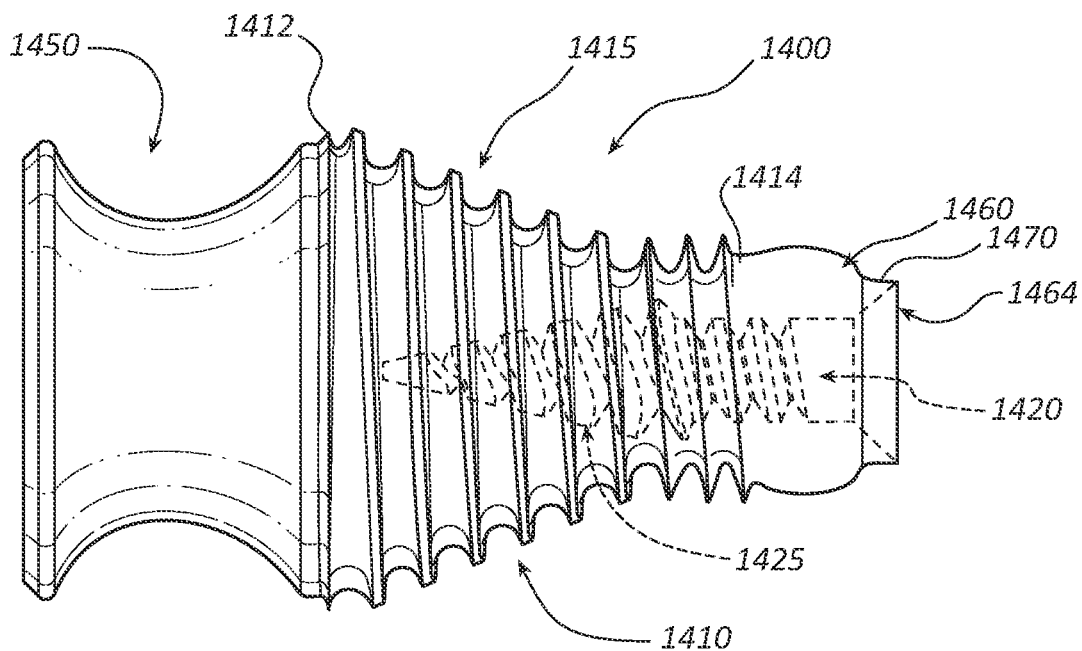
FIG. 14A is a perspective view of a vertebral bone anchor according to still other embodiments.
Figure 14B:
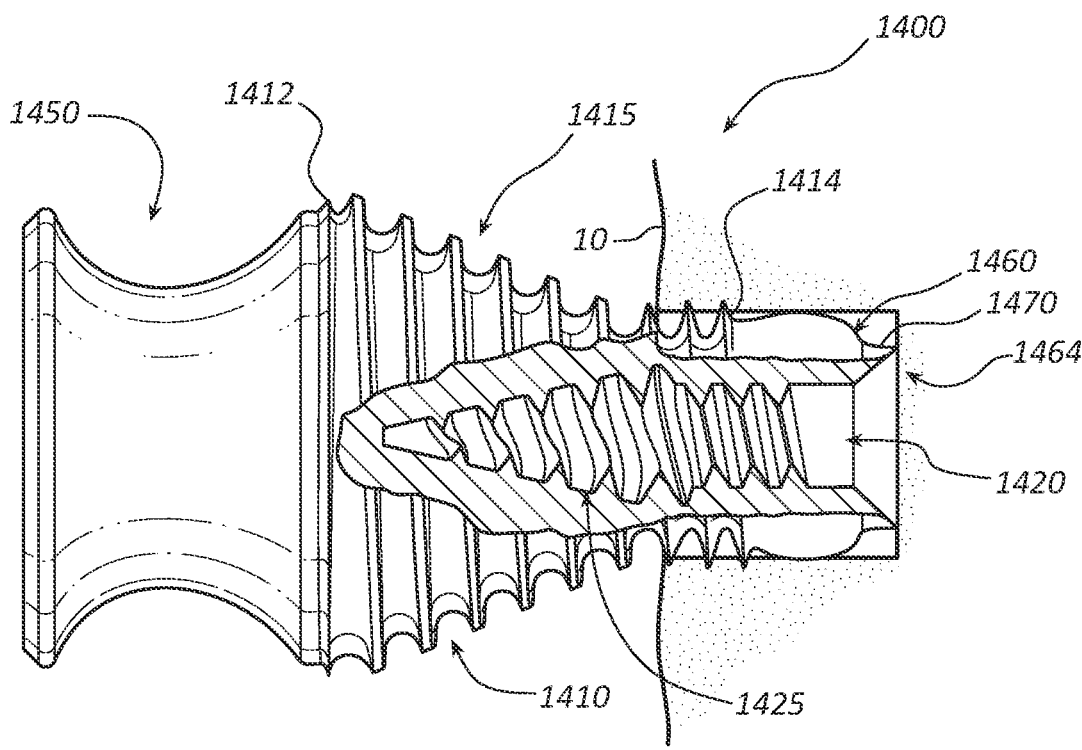
FIG. 14B is a perspective, partial cutaway view of the bone anchor of FIG. 14A being engaged with a vertebral body.
Figure 15A:
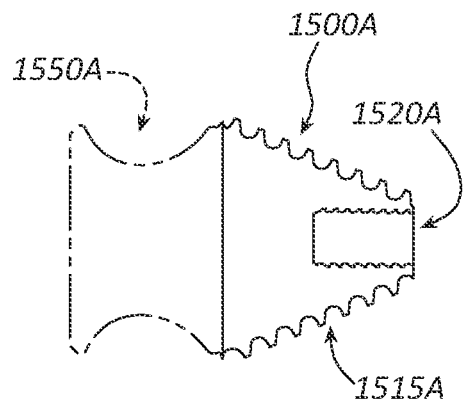
FIGS. 15A-15F are cross-sectional views of various bone anchors comprising distinct sizes, shapes, and/or types of inner chambers.
Figure 15D:
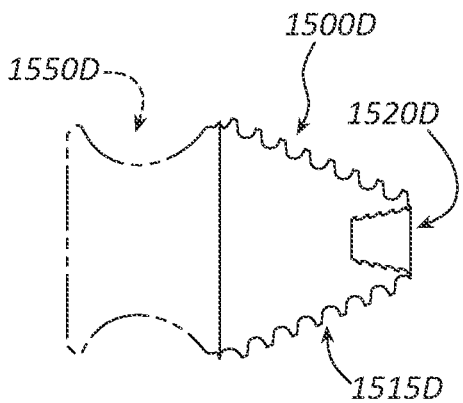
Figure 15B:
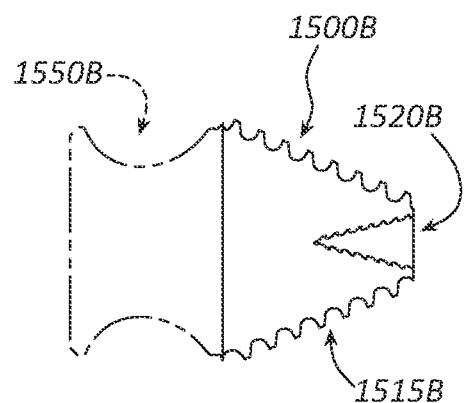
Figure 15E:
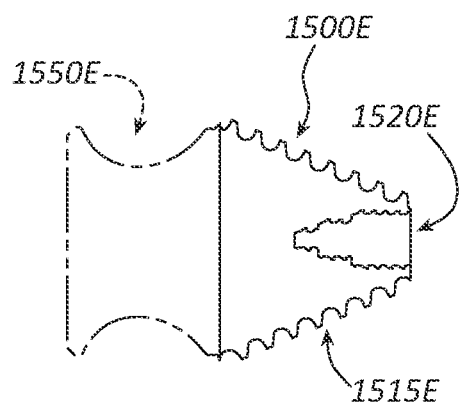
Figure 15C:
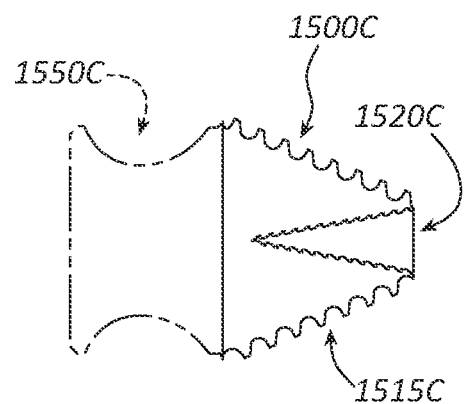
Figure 15F:
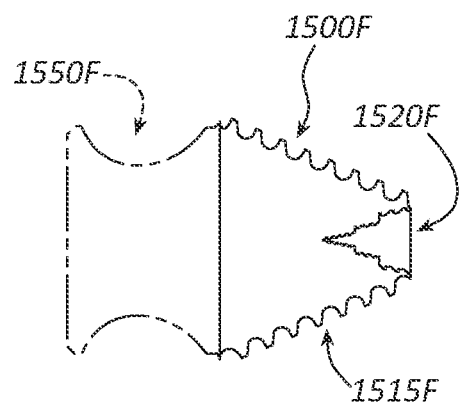

Another example of a bone anchor 1400 according to still other embodiments is shown in FIGS. 14A and 14B. Bone anchor 1400 is similar to the bone anchors depicted and discussed previously except for the configuration of the tip, which includes a distal end portion 1470 that is cylindrical and an adjacent curved/bowed portion 1460. Cylindrical tip 1470 may again comprise a sharp edge to facilitate penetration/tamping into a vertebral body or other bone. The adjacent bowed/curved portion 1460 may serve one or more useful functions such as providing inhibiting forces to slow down the tamping of bone anchor 1400 prior to engagement of threads, external and/or internal, with the adjacent bone. This may allow for creation of an initial circular channel with an expansion created by the bowed/curved portion 1460 (or similar cylindrical section) wide enough to allow the initial thread starting from external thread form 1415 to enter below the cortical wall and easily engage the cancellous bone underneath the cortical wall for simple initial screw purchase and advancement.

As mentioned above in connection with section 1360, section 1460 may, in alternative embodiments, comprise a tapering and/or conical section rather than a curved/bowed section, which may provide similar benefits by, for example, slowing the rate of tamping by providing an opposing force after tip 1470 has entered the bone.

Bowed/curved section 1460 extends from the distal end 1414 of tapering portion 1410 (opposite proximal end 1412). In the depicted embodiment, tip section 1460 comprises external threads that preferably begin at or near the apex of the curvature, as described above, and may extend cylindrically for a short distance, after which they may taper along the tapered section 1410 to form a part of external thread form 1415.

Tip 1460 further comprises an internal chamber 1420 that extends into the tapering portion. In addition, preferably, at least the proximal portion of chamber 1420 tapers or otherwise varies in size in a direction opposite to the taper of the exterior surface of bone anchor 1400. Again, this may allow for bone entering chamber 1420 to be compacted as the anchor 1400 is driven into the bone. In the depicted embodiment, chamber 1420 is cylindrical in shape along the tip portions and the reverse tapering of chamber 1420 begins at, or at least substantially at, the distal end 1414 of the tapering section 1410.

However, this need not be the case in all embodiments. Indeed, the reverse tapering or other decrease in size of the chamber 1420 from the distal to the proximal end may begin within the bowed portion 1460, within the cylindrical tip portion 1470, or may begin proximally of the distal end 1414 of the tapering section. As another alternative, the reverse tapering or other beginning of a decrease in size of the chamber 1420 from distal to proximal may begin at the point at which the external threads begin, which may, as described above, coincide, or at least substantially coincide, with the apex of the curve and/or the midpoint of the bowed portion 1460.

Internal threads may also be formed within chamber 1420. For example, in the depicted embodiment, the internal thread form 1425 begins at or near the beginning of the external thread form 1415. Of course, this need not be the case in all embodiments. Indeed, the internal thread form may begin proximally or distally of the external thread form in alternative embodiments.

In the depicted embodiment, the internal thread form 1425 comprises a non-tapering section that may overlap with the bowed section 1460. In some cases, the internal thread form 1425 may coincide identically or at least substantially identically with the bowed section 1460 and/or tip 1470. The internal thread form 1425 may then reverse taper along the tapering section of the inner chamber 1420.

In some embodiments, the external thread form 1415 may differ from the internal thread form 1425 in one or more ways so as to provide a differential in force between forces generated by the external thread form 1415 on bone adjacent thereto and forces generated by the inner thread form 1425 on bone adjacent thereto in one or more of the ways described elsewhere herein.

Bone anchor 1400 may further comprise an engagement member 1450 for engaging ligaments or other engagement bands, as previously mentioned. One or more of the other features previously described, such as a central cannulation, a keyed feature to facilitate engagement with a driver or other suitable instrument for driving the anchor 1400 into a vertebral body 10 or other tissue, and/or one or more tunnels and/or openings that extend from the exterior surface of anchor 1400 to the inner chamber 1420 may also be provided if desired/useful.

As shown in FIG. 14B, once the tip (made up of tip portions 1460 and 1470) has been tamped or otherwise inserted into the vertebral body 10, external threads 1415 may be engaged and bone anchor 1400 may be advanced further into the vertebral body 10 by rotation of bone anchor 1400, as previously described.

Additional bone anchors 1500A-1500F are depicted in FIGS. 15A-15F, respectively, each of which comprises a respective outer thread form 1515A-1515F, a respective engagement member 1550A-1550F having a seat for coupling with a tether, as described throughout this disclosure, along with distinct types of respective inner chambers 1520A-1520F.

More particularly, inner chamber 1520A comprises a non-tapering or cylindrical chamber, which is shown having bone engaging protrusions, such as inner threads, formed therein.

Inner chamber 1520B comprises a tapering or conical chamber that, as previously discussed, preferably tapers in a direction opposite that of the outer thread form 1515B such that the cross-sectional area of the chamber decreases in a distal to proximal direction. Inner chamber 1520B extends to about the midpoint of the anchor comprising outer thread form 1515B. Again, an inner thread form or other bone engaging protrusions may be formed within the inner chamber 1520B. However, it is contemplated that, in some embodiments, such bone engaging protrusions may be omitted if desired.

Inner chamber 1520C also comprises a tapering or conical chamber that tapers in a direction opposite that of outer thread form 1515C. However, unlike inner chamber 1520B, inner chamber 1520C extends along at least substantially the entire length of the portion of anchor 15000 having external threads 1515C for engagement with vertebral bone. Again, an inner thread form or other bone engaging protrusions may, but need not always be, formed within the inner chamber 1520C.

Inner chamber 1520D also comprises a tapering or conical chamber that tapers in a direction opposite that of outer thread form 1515D. However, unlike inner chambers 1520B and 1520D, the proximal end of inner chamber 1520D comprises a flattened surface rather than tapering to a pointed end. Again, an inner thread form or other bone engaging protrusions may, but need not always be, formed within the inner chamber 1520D.

Inner chamber 1520E of bone anchor 1500E comprises a chamber that, like the previously described tapering inner chambers, decreases in cross-sectional area from the distal to the proximal end of the chamber. However, unlike the chambers of bone anchors 1520A-1520D, inner chamber 1520E does so in a stepwise rather than a tapering manner. It is contemplated, however, that some embodiments may both taper and have one or more such steps if desired. Inner chamber 1520E comprises a flattened proximal end, similar to inner chamber 1520D. Again, an inner thread form or other bone engaging protrusions may, but need not always be, formed within the inner chamber 1520E.

Finally, inner chamber 1520F of bone anchor 1500F comprises both steps and tapering sections. In addition, the proximal end of inner chamber 1520F tapers to a pointed proximal end. However, it should be understood that the proximal end need not be pointed in other contemplated embodiments. Again, an inner thread form or other bone engaging protrusions may, but need not always be, formed within the inner chamber 1520F.

Figure 16:
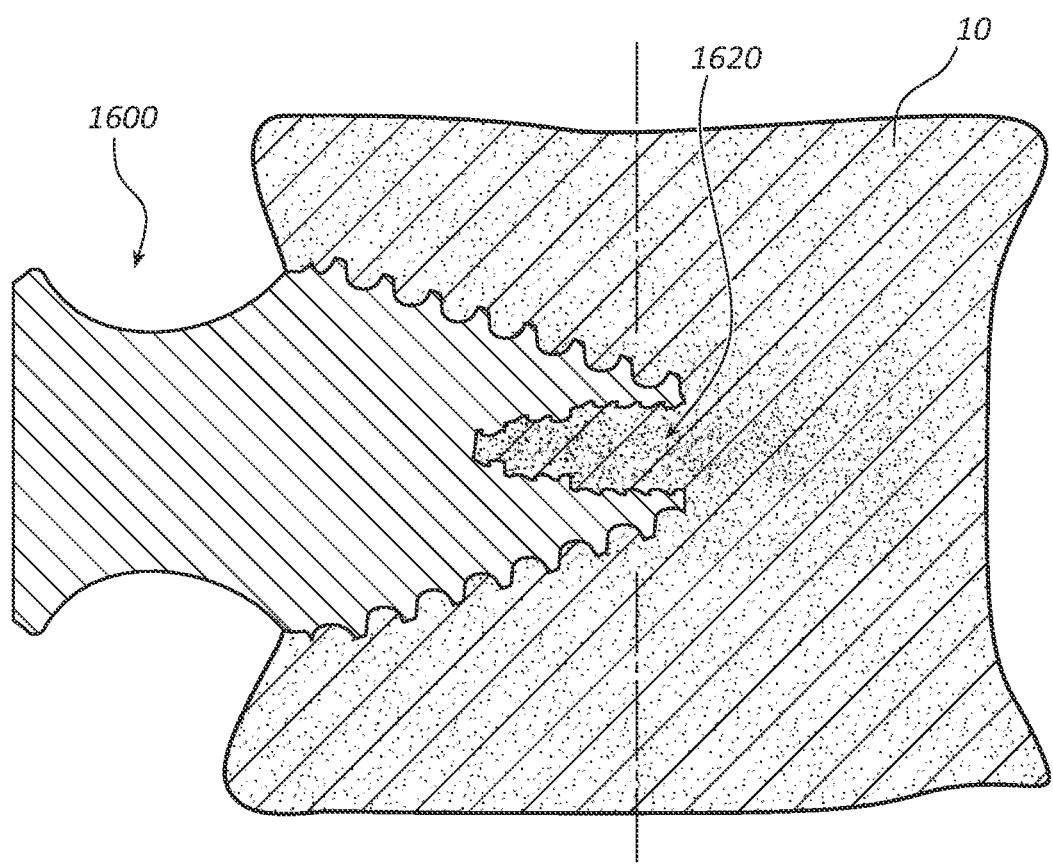
FIG. 16 is a cross-sectional view of another bone anchor within a vertebral body, the bone anchor having a stepped inner chamber with bone engaging features.

FIG. 16 illustrates a bone anchor 1600 inserted within a vertebral body 10. Bone anchor 1600 comprises an inner chamber 1620 that decreases in cross-sectional size/area from the distal to the proximal end of the chamber, as previously described. In addition, this figure illustrates how the inner chamber 1620 serves to engage and pack cancellous bone from the vertebral body 10 into the chamber 1620 as the bone anchor 1600 is advanced. This increases the density of the cancellous bone (possibly including some cortical bone from the initial penetration through the cortical wall of the implant) within the inner chamber 1620, which may provide a number of benefits, such as increased compression, increased surface area of bone contact, and increased healing and/or osseointegration of the implant.

As also shown in FIG. 16, some embodiments may also result in a gradient of increased bone density that may extend beyond the inner chamber 1620 of the implant 1600, which may effectively extend the length of fixation of the implant. Without being limited by theory, it is thought that the ability of the inner chamber to engage and pack bone within the implant, which may result from the aforementioned threads or other bone engaging members within the chamber and/or the narrowing of the chamber in a distal to proximal direction, may act as a plow or a prow of a ship to compress the region of the vertebral body in front of (distal of) the implant as it is advanced within the vertebral body. This may increase the strength of the coupling of the anchor with a vertebral body and may thereby increase the strength of the coupling between adjacent vertebrae and/or decrease the likelihood of the anchor becoming loosened and/or disengaged.

Figure 17:
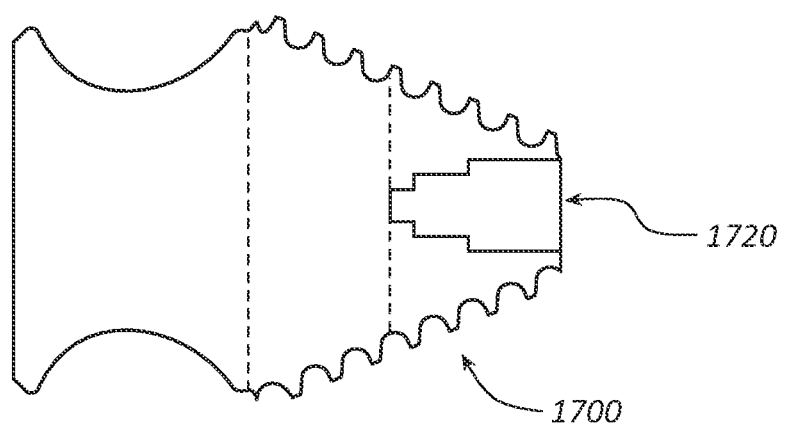
FIG. 17 is a cross-sectional view of another bone anchor having a stepped inner chamber.

FIG. 17 illustrates another embodiment of a bone anchor 1700 having an inner chamber 1720 that increases in cross-sectional area from the proximal to distal end in a stepwise fashion. Although no bone engaging members are depicted, it should be understood that any of the aforementioned threads or other bone engaging members may be present if desired. Inner chamber 1720 is shown extending to about the midpoint of the bone-engaging portion of the implant 1700. However, due one or more of the aforementioned advantageous features, such as providing bone engaging protrusions formed within the inner chamber and/or a profile that increases in cross-sectional area, at least in part, from a proximal end of the inner chamber to a distal end of the inner chamber, it is thought that some embodiments may be able to compress a very large portion of cancellous bone within inner chamber 1720.

For example, if the entire volume of the implant is considered to be "X", the volume of the inner chamber 1720 may be less than $0.5(X)$, or in some cases depending upon the size and shape of the inner chamber, even less than $0.25(X)$. However, due to the compacting of bone within the chamber, a relatively large portion of bone from the proximal portion of the vertebral body may be compacted as the anchor/implant 1700 is advanced such that, a volume of original, uncompacted bone much larger than the volume of chamber 1720 may, following full installation of chamber 1720, compacted therein. For example, in some embodiments and implementations, an uncompacted volume of (mostly cancellous) bone that is greater than about 0.75(X) may be compacted into a chamber having a size of less than 0.25(X). In some such embodiments and implementations, an uncompacted volume of (mostly cancellous) bone that is greater than about 0.90(X) may be compacted into a chamber having a size of less than 0.25(X).

Stated otherwise, using one or more of the inventive principles disclosed herein, a volume of uncompacted bone may be compacted into the inner chamber or chambers of the implant such that the compacted bone is at least twice as dense as the surrounding uncompacted bone. In some such embodiments and implementations, the volume of uncompacted bone may be compacted into the inner chamber or chambers of the implant such that the compacted bone is at least three times, or even four times, as dense as the surrounding uncompacted bone.

Figure 18A:
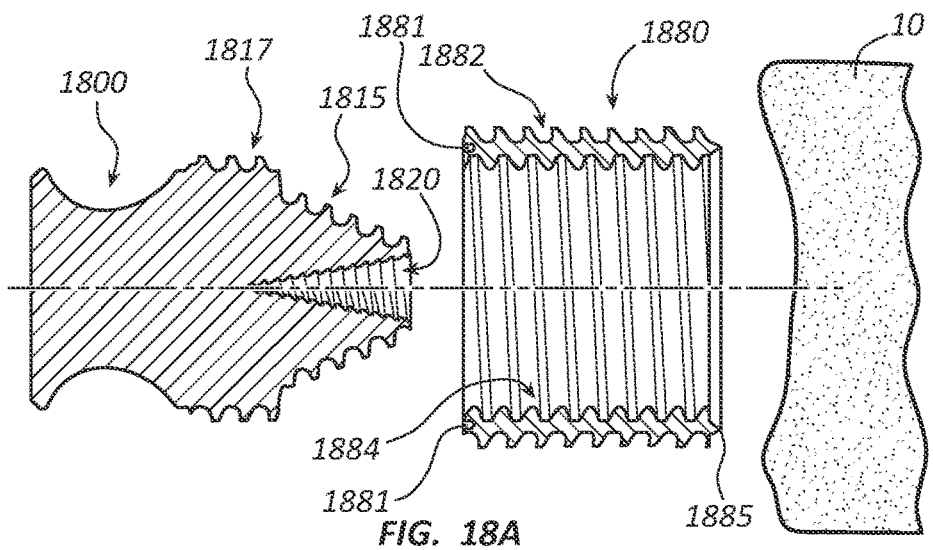
FIG. 18A depicts a two-piece bone anchor assembly according to some embodiments.
Figure 18B:
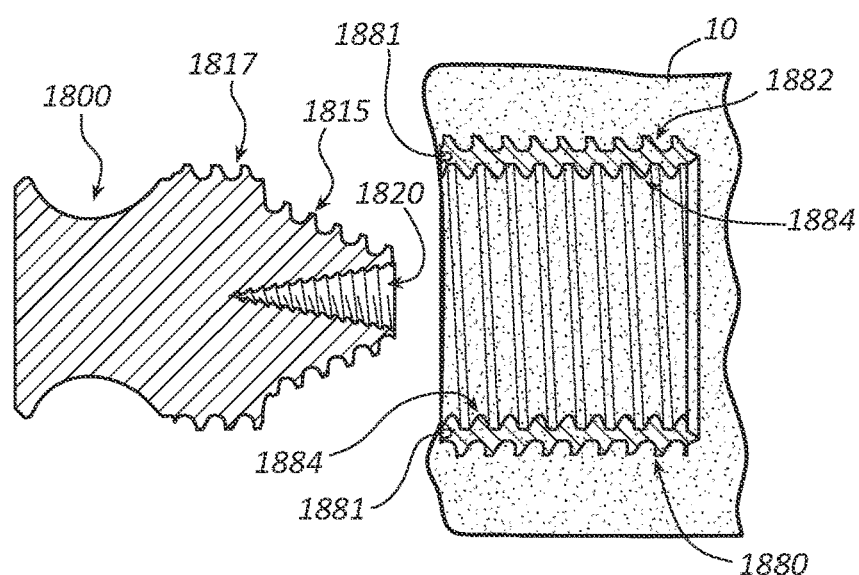
FIG. 18B depicts the two-piece bone anchor assembly of FIG. 18A after the first/outer piece of the assembly has been positioned within a vertebral body.
Figure 18C:
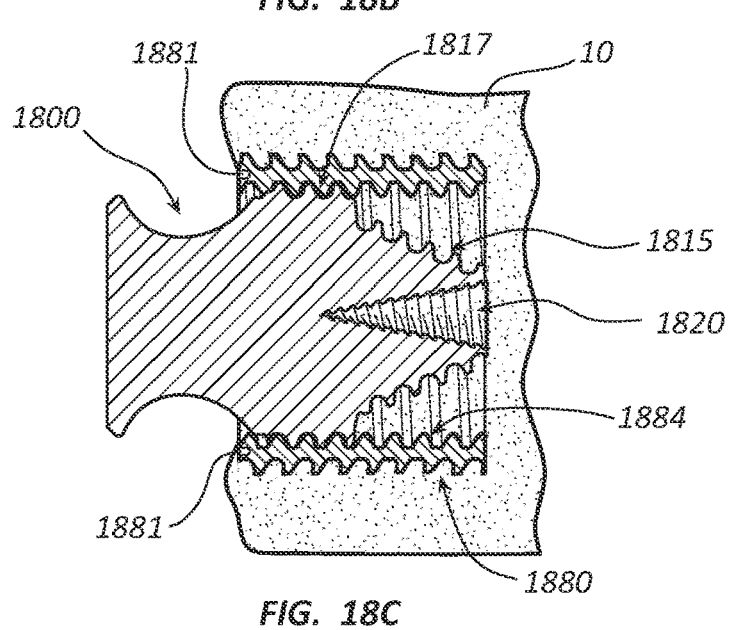
FIG. 18C depicts the two-piece bone anchor assembly of FIGS. 18A and 18B following coupling of the inner and outer pieces and fully extending the bone anchor assembly into the vertebral body.

FIGS. 18A-18C depict a bone anchor system comprising two interacting bone anchor elements, namely, a first, inner bone anchor 1800 and a second, outer bone anchor sleeve 1880. Bone anchor sleeve 1880 comprises a cylindrical shape having both inner and outer engagement features. More particularly, the outer surface of bone anchor sleeve 1880 comprises a first/outer thread form 1882 and the inner surface of bone anchor sleeve 1880 comprises a second/inner thread form 1884.

First thread form 1882 may be used to advance bone anchor sleeve 1880 into bone, such as vertebral body 10. A sharp leading edge 1885 may be provided to obtain initial purchase into the cortical wall of the vertebral body 10. Once this purchase has been obtained, sleeve 1880 may be threadably inserted into the vertebral body 10, as shown in FIG. 18B. One or more grooves 1881 or other instrument engaging features may be formed to facilitate use of a driver or other instrument in advancing the sleeve 1880.

After advancing, either fully or partially, the sleeve 1880 into the vertebral body 10, bone anchor 1800 may be advanced within the bone occupying the inner region of sleeve 1880. Initially, this advancement may be similar to that described previously in connection with one-piece bone anchor embodiments. However, eventually bone anchor 1800 will be physically coupled with sleeve 1880.

Indeed, as shown in each of FIGS. 18A-18C, bone anchor 1800 comprises two distinct outer threaded portions—a first threaded portion 1815 at the distal end and a second threaded portion 1817 adjacent and proximal to the first threaded portion 1815. First threaded portion 1815 is configured to threadably engage the bone, as previously mentioned. However, second threaded portion 1817 is configured to engage the inner thread form 1884 of sleeve 1880 after sufficient advancement of first threaded portion 1815 within vertebral body 10, as shown in FIG. 18C.

In the depicted embodiment, there is a ledge between thread form 1815 and thread form 1817. However, this need not be the case for all contemplated embodiments. Rather, in other embodiments there may be a smooth transition between these two thread forms. In addition, although thread form 1815 is shown with a taper similar to the tapering outer thread forms of previous embodiments and thread form 1817 is shown with a cylindrical or non-tapering structure, this may also vary in alternative embodiments. For example, in some embodiments, proximal thread form 1817 may taper. In some such embodiments, inner thread form 1884 of sleeve 1880 may have a similar taper, either alone or in conjunction with a corresponding taper to outer thread form 1882 or another series of bone engaging features.

As with previous embodiments, bone anchor 1800 may further comprise an inner chamber 1820, which may comprise any of the shapes, features, and/or elements previously mentioned. In the depicted embodiment, inner chamber 1820 comprises a taper opposite the taper of thread form 1815 and may also be threaded and/or have other protruding, bone engaging members. As previously mentioned, in some embodiments having an inner thread form, the inner thread form may be distinct from one or both of the outer thread forms, such as, for example, by differing in thread direction/handedness, number of starts, angle, pitch diameter, major diameter, and/or minor diameter.

In addition, unlike previous embodiments, the combined implant of bone anchor 1800 and sleeve 1880 is configured to compact bone in two distinct regions. More particularly, as with previous embodiments, bone may be compacted within chamber 1820. In addition, further bone compacting may take place within the region defined in between sleeve 1880 and thread form 1815, which may further contribute to the strength of the coupling with the vertebral body 10. Thus, although the depicted embodiment is shown with a single, continuous inner thread form 1884, it is contemplated that, in alternative embodiments, two thread forms or one thread form and an adjacent alternative bone engaging structure, such as a plurality of spikes or other protrusions, may be formed along the inner surface of sleeve 1880, with the proximal thread form being configured for engagement with bone anchor 1800 and the distal thread form or other bone engaging features being configured for engaging and/or drawing cancellous bone into the annular chamber formed between these two pieces of the assembly/system.

Bone anchor 1800 may otherwise be similar to and/or incorporate any of the features, elements, and/or structures previously presented in connection with any of the other embodiments disclosed herein. Thus, preferably an inner chamber 1820 is formed, which, as shown in FIGS. 18A-18C may, for example, comprise a reverse taper, either partial or full, and may comprise internal threads or other bone engaging features that are preferably configured to draw and compact bone into inner chamber 1820. In some embodiments, the profile of inner chamber 1820 may increase in cross-sectional area, at least in part, from a proximal end of the inner chamber 1820 to a distal end of the inner chamber 1820 without providing the taper shown in the figures, such as by providing steps, for example. In addition, as previously mentioned, some embodiments may be configured to provide a force differential between the internal and external threads or other bone engaging features.

Figure 19A:
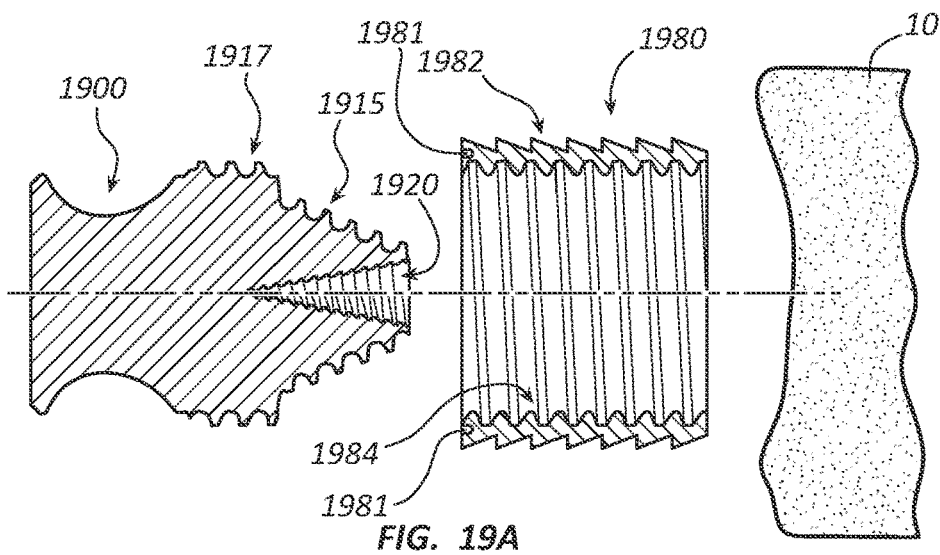
FIG. 19A depicts a two-piece bone anchor assembly according to other embodiments.
Figure 19B:
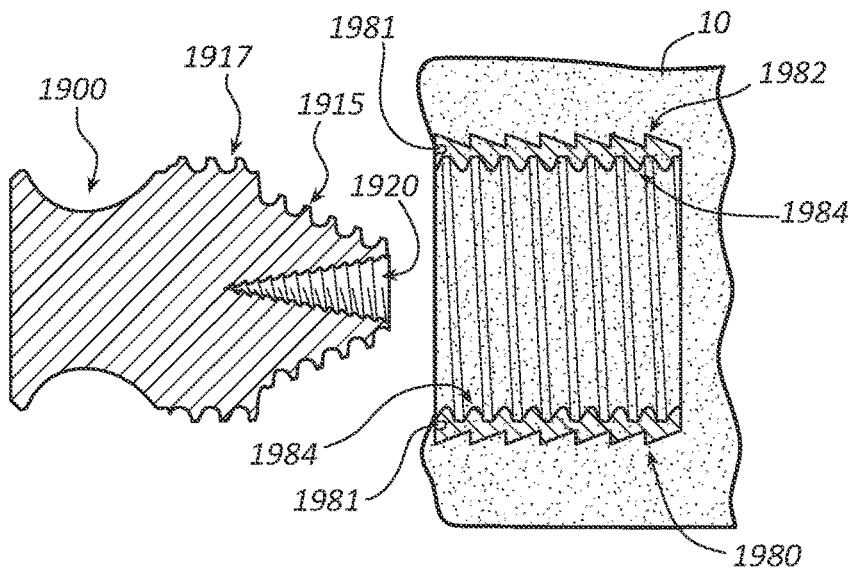
FIG. 19B depicts the two-piece bone anchor assembly of FIG. 19A after the first/outer piece of the assembly has been positioned within a vertebral body.
Figure 19C:
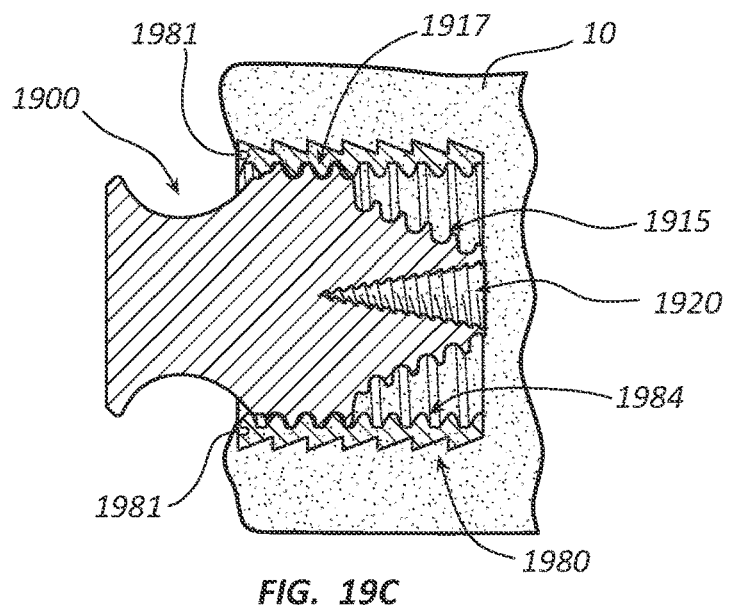
FIG. 19C depicts the two-piece bone anchor assembly of FIGS. 19A and 19B following coupling of the inner and outer pieces and fully extending the bone anchor assembly into the vertebral body.

FIGS. 19A-19C depict another bone anchor system comprising two interacting bone anchor elements, namely, a first, inner bone anchor 1900 and a second, outer bone anchor sleeve 1980. Bone anchor sleeve 1980 again comprises a cylindrical shape having both inner and outer engagement features. More particularly, the outer surface of bone anchor sleeve 1980 comprises outer bone engagement features in the form of a series of ratchet-like steps 1982 or the like and the inner surface of bone anchor sleeve 1980 comprises a thread form 1984.

Bone engaging features 1982 may be used to advance bone anchor sleeve 1980 into bone, such as vertebral body 10. A sharp leading edge (not shown) may be provided to obtain initial purchase into the cortical wall of the vertebral body 10 if desired. Once this purchase has been obtained, sleeve 1980 may be driven or otherwise advanced into the vertebral body 10, as shown in FIG. 19B. One or more grooves 1981 or other instrument engaging features may be formed to facilitate use of a driver or other instrument in advancing the sleeve 1980. Although not shown, a sharpened leading edge may be provided to facilitate the initial tamping of sleeve 1980 into the vertebral body 10 if desired.

After advancing, either fully or partially, the sleeve 1980 into the vertebral body 10, bone anchor 1900 may be advanced within the bone occupying the inner region of sleeve 1980, as discussed above in connection with bone anchor 1800.

As also discussed above in connection with bone anchor 1800, as shown in each of FIGS. 19A-19C, bone anchor 1900 comprises two distinct sets of engagement protrusions, both of which comprise threads in the depicted embodiment but need not in other contemplated embodiments. More particularly, a first threaded portion 1915 is formed at the distal end and a second threaded portion 1917 is formed adjacent and proximal to the first threaded portion 1915. First threaded portion 1915 is configured to threadably engage the bone, as previously mentioned, and second threaded portion 1917 is configured to engage the inner thread form 1984 of sleeve 1980 after sufficient advancement of first threaded portion 1915 within vertebral body 10, as shown in FIG. 19C.

Bone anchor 1900 may otherwise be similar to and/or incorporate any of the features, elements, and/or structures previously presented in connection with any of the other embodiments disclosed herein. Thus, again, preferably an inner chamber 1920 is formed, which may comprise a reverse taper, either partial or full, and/or internal threads or other bone engaging features that are preferably configured to draw and compact bone into inner chamber 1920. Rather than a strict taper, the profile of inner chamber 1920 may increase in cross-sectional area, at least in part, from a proximal end of the inner chamber 1920 to a distal end of the inner chamber 1920 in another manner, such as by a series of discrete steps or the like. In addition, as previously mentioned, some embodiments may be configured to provide a force differential between the internal and external threads or other bone engaging features.

Figure 20A:
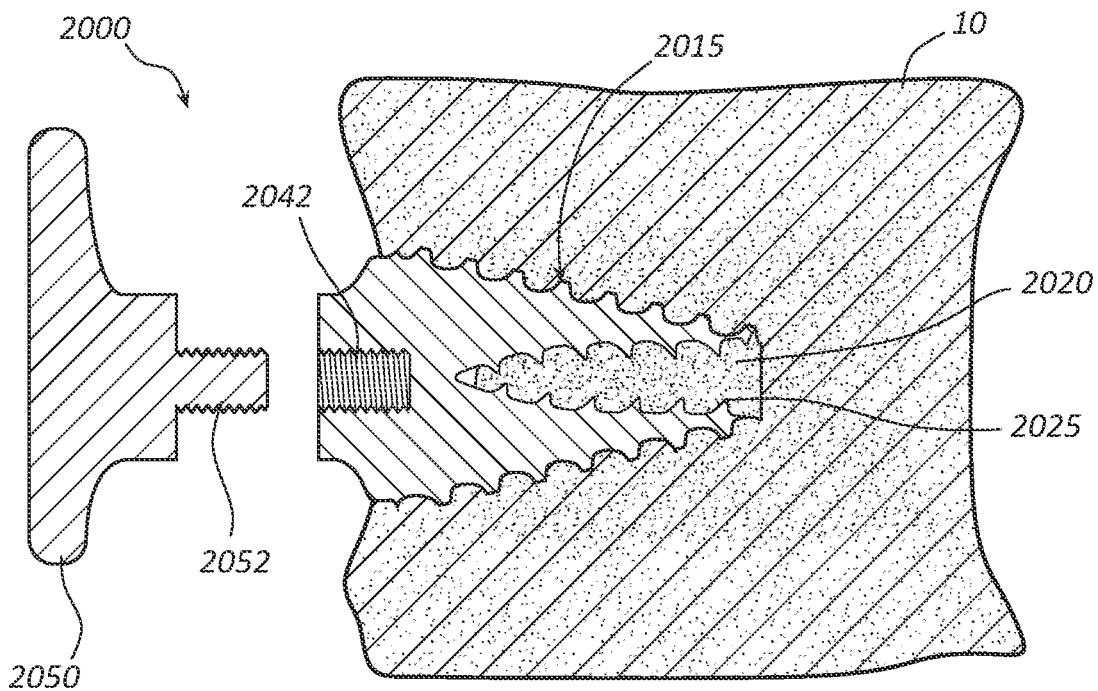
FIG. 20A is a cross-sectional view of a bone anchor having a removable cap/tether engagement member according to some embodiments shown with the cap removed.
Figure 20B:
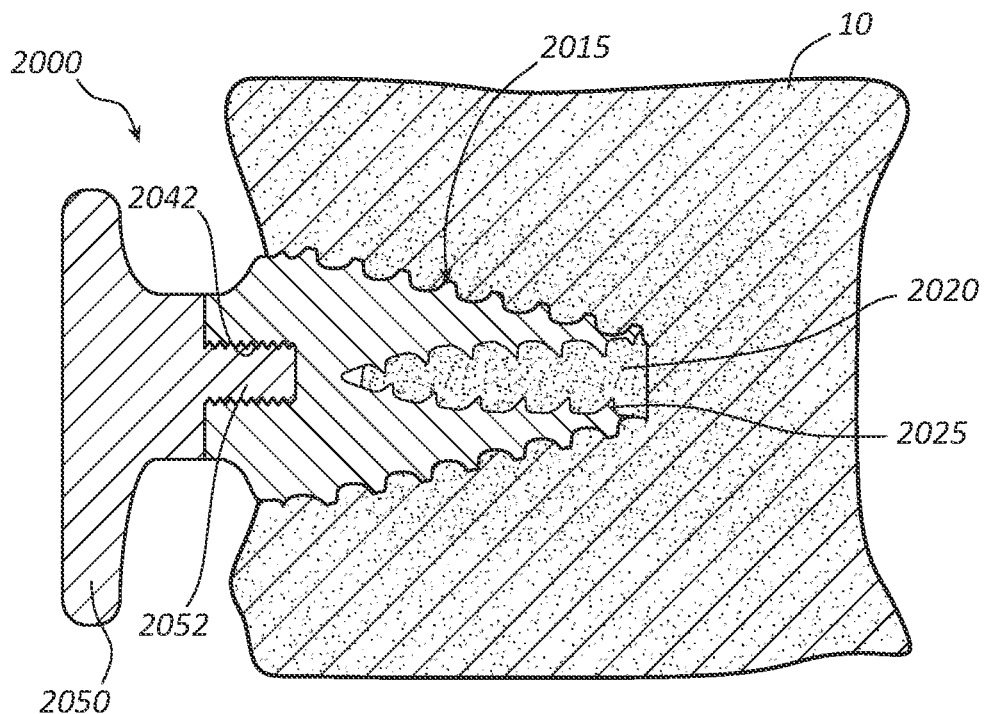
FIG. 20B depicts the bone anchor of FIG. 20A after the removable cap has been coupled with the bone-engaging portion of the anchor.

A further embodiment of a bone anchor 2000 is depicted in FIGS. 20A and 20B. Bone anchor 2000 comprises a tether engagement member 2050, which in the depicted embodiment comprises a cap, that is removably coupleable with the body of the anchor 2000. In the depicted embodiment, tether engagement member 2050 further comprises a saddle having a threaded shaft 2052 configured to be threadably received within a threaded hole 2042 formed in a proximal portion of the bone engaging portion of anchor 2000 having external bone engaging threads 2015.

Tether engagement member/saddle 2050 may allow a surgeon/practitioner to, after advancing the bone engaging portion of anchor 2000 into a vertebral body 10, couple a loop tether around the portion of the anchor 2000 that protrudes from the vertebral body 10, as shown in FIG. 20A. After the tether (not shown) is wrapped around this portion of the anchor 2000, the tether engagement member/saddle 2050, which may be considered a "cap" of the assembly in this context, may be coupled to the bone engaging portion of the anchor 2000 in order to more permanently secure the tether to a pair of adjacent anchors and corresponding vertebral bodies. One perceived benefit with assemblies having removable saddle/caps is that anchors need not be over-loaded by requiring a surgeon/practitioner to stretch the tether around the proximal wall portion of the tether engagement member/saddle/cap 2050.

The remaining portions of bone anchor 2000 may be similar to any of those previously described. Thus, in the example of the depicted embodiment, an inner chamber 2020 may be provided, which may comprise a plurality of spikes (or, in other embodiments, threads or other bone engaging features) 2025 to facilitate packing cancellous bone into the chamber 2020.

Figure 21A:
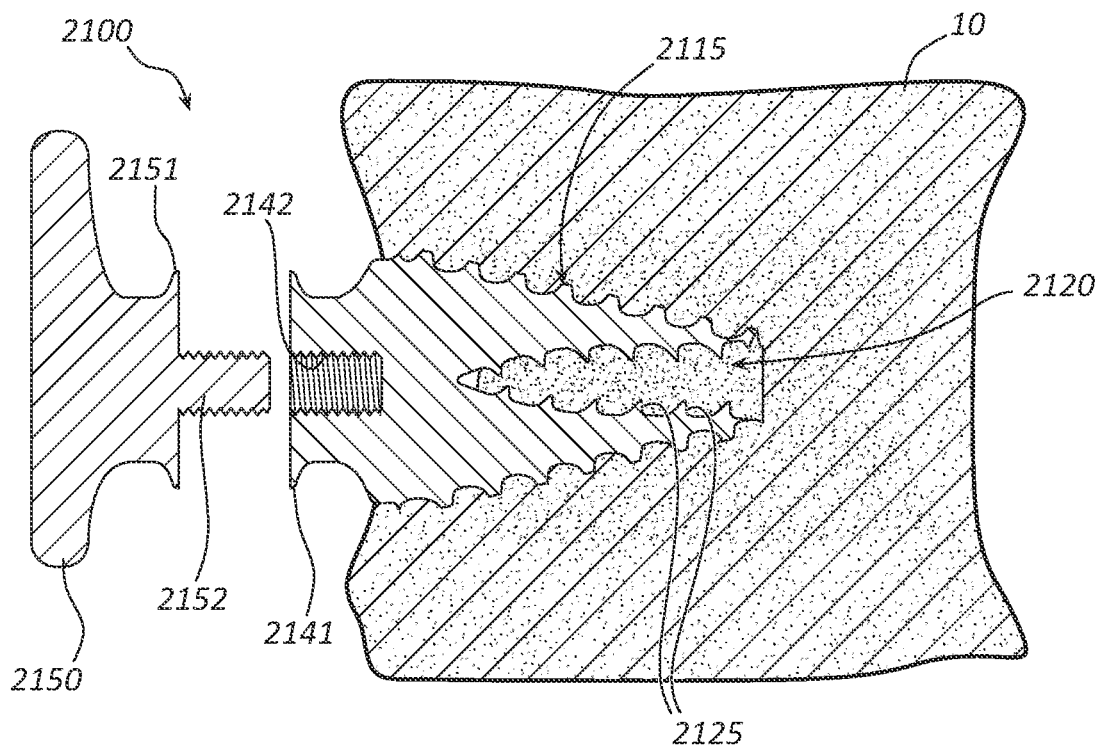
FIG. 21A is a cross-sectional view of a bone anchor having a removable cap/tether engagement member according to other embodiments shown with the cap removed.
Figure 21B:
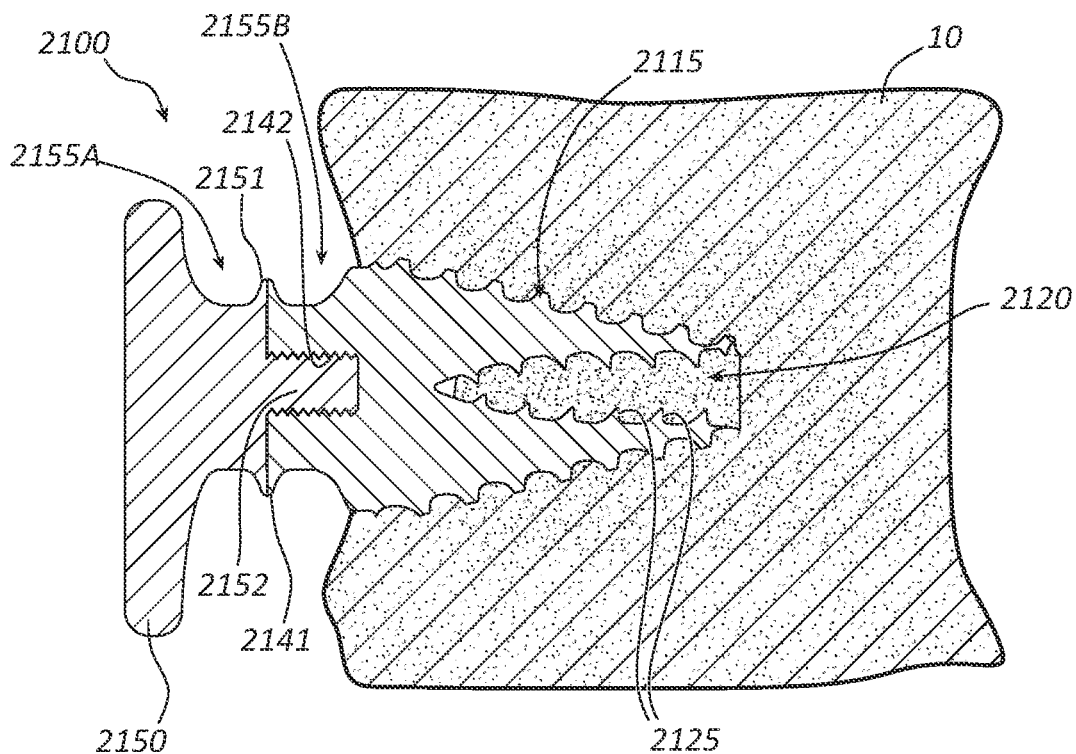
FIG. 21B depicts the bone anchor of FIG. 22A after the removable cap has been coupled with the bone-engaging portion of the anchor.

Another embodiment of a bone anchor 2100 is depicted in FIGS. 21A and 21B. Bone anchor 2100 is similar to bone anchor 2000 in that it comprises a tether engagement member 2150 or cap that is removably coupleable with the body of the anchor 2100. However, tether engagement member 2150 defines a portion of a W-shaped tether seating region having two seats 2155A and 2155B, as shown in FIG. 21B. These two seating regions are defined in part by respective circular protrusions 2141 and 2151 formed in the bone engaging and saddle/cap portions of the assembly, respectively.

Once the cap 2150 has been coupled with the bone engaging portion of the implant, which may take place by threadably engaging threaded shaft 2152 with threaded hole 2142, the two seating regions are formed, as shown in FIG. 21B. Seating region 2155B may be used as a temporary seat to allow a surgeon to extend a loop tether (not shown) about the saddle/seat region 2155B with cap 2150 removed, after which the tether may either be left in seating region 2155B or may be moved to seat 2155A to provide a more secure coupling to the remainder of the bone anchor 2100 and vertebral body 10. Because the center lip (defined by protrusions 2141 and 2151) is less pronounced than the proximal lip provided by the portion of the cap 2150 that is proximal of seating region 2155A, extending a loop tether about this center lip will require substantially less stretching/overloading of the loop tether during this temporary stage than would have been required to extend the loop tether about the proximal, larger lip defined by the proximal portion of cap 2150.

The remaining portions of bone anchor 2100 may be similar to any of those previously described. Thus, in the example of the depicted embodiment, an inner chamber 2120 similar to inner chamber 2020 may be provided, which may comprise a plurality of spikes (or, in other embodiments, threads or other bone engaging features) 2125 to facilitate packing cancellous bone into the chamber 2120.

Figure 22:
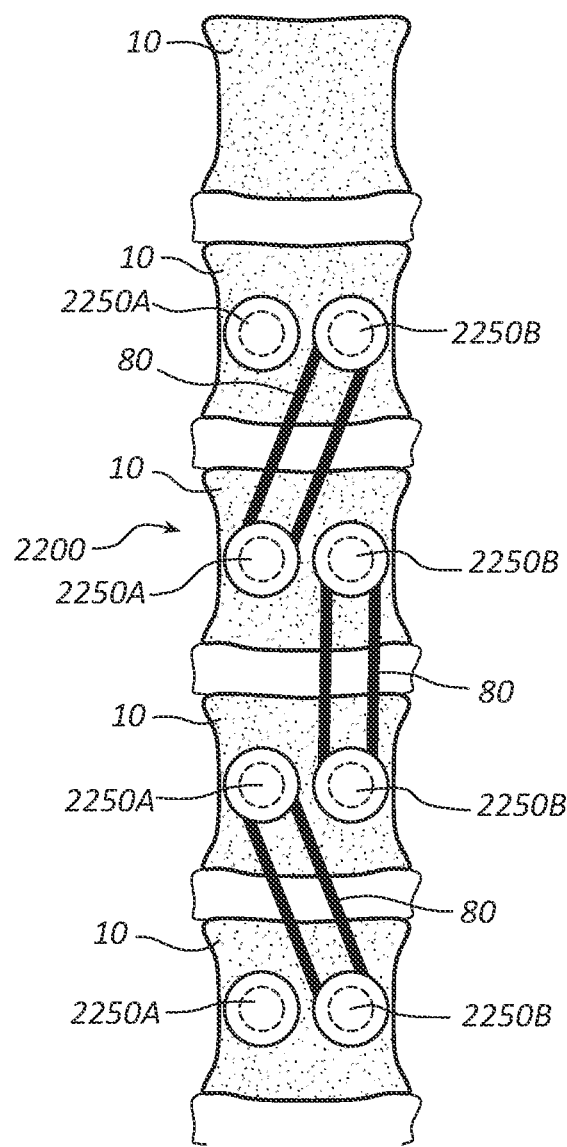
FIG. 22 depicts a system for spinal deformity correction according to some embodiments comprising multiple bone anchors per vertebral body and configured to allow for application of corrective forces in multiple directions simultaneously, such as derotational forces.

Another example of a system for spinal deformity correction 2200 is shown in FIG. 22. System 2200 comprises a plurality of bone anchors, each of which comprises a bone engaging portion (not visible in the figure) and a tether engaging portion 2250 coupled with the bone engaging portion. The bone engaging portion may, but need not, comprise any of the inner chambers, bone engaging features, thread forms or other elements disclosed herein. However, unlike any of the previous embodiments, system 2200 comprises two bone anchors and two corresponding tether engaging portions, such as saddles, for each vertebral body 10.

More specifically, each vertebral body 10 comprises a first bone anchor extending in a first column along a spinal column and a second bone anchor adjacent to the first bone anchor and extending in a second column adjacent to the first column along the spinal column. In FIG. 22, the portions of the first and second bone anchors that protrude from the vertebral bodies 10 are shown as tether engaging portions 2250A and 2250B, respectively.

Because of the presence of two anchors within each vertebral body 10 (or, in alternative embodiments and implementations, at least a subset of the vertebral bodies 10), a surgeon/practitioner may be able to apply lateral forces, such as derotational forces, if desired, to one or more portions of the spine, along with the forces directed along the axis of the spine. Thus, as shown in FIG. 22, a first tether 80 extends between the right anchor 2250B at the superior end of the system along the spine to the left anchor 2250A coupled with the adjacent vertebral body 10 below. The adjacent anchor 2250B in the same vertebral body 10 as the left anchor 2250A is then coupled with the right anchor 2250B in the adjacent vertebral body 10 below. The adjacent anchor 2250A to the left, however, is then coupled with the right anchor 2250B of the vertebral body 10 below. Thus, both axial forces, which are typical of the previous embodiments, and non-axial forces, may be provided using the same assembly/system.

Of course, this is just an example. As those of ordinary skill in the art will appreciate, by providing two (or more) adjacent anchors within one or more vertebral bodies 10, more precise and diverse forces may be applied to the spine to achieve other spinal deformity corrections, such as reversing torsional asymmetry induced by scoliosis, coronal correction, restoration of thoracic kyphosis, and/or realignment of thoracic torsion. Thus, it should be understood that tethers/ligaments 80 may be applied to the various anchors in a system comprising a plurality of anchors per vertebral body, such as system 2200, in any number of ways, which may include use of multiple tethers 80 coupled with a single anchor in some cases. For example, it may be desirable to couple a single anchor with both an anchor directly above/below and an anchor adjacent to the anchor directly above/below to apply both axial and derotational or other non-axial/lateral forces to the same anchor.

Figure 23:
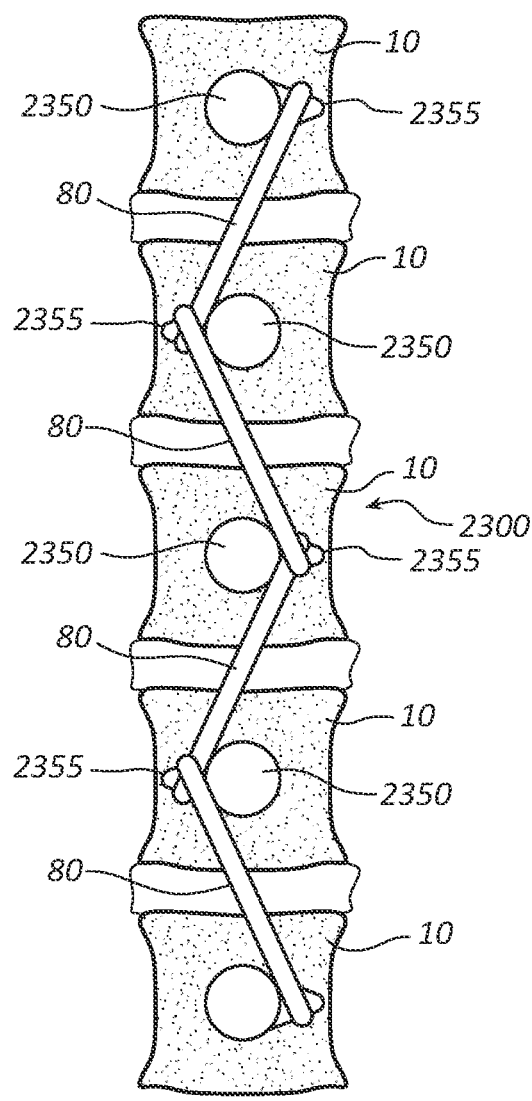
FIG. 23 depicts another example of a system for spinal deformity correction according to other embodiments comprising configured to allow for application of corrective forces to a spine in multiple directions simultaneously, such as derotational forces.

Another example of a derotational system 2300 is shown in FIG. 23. Unlike system 2200, however, system 2300 comprises a single anchor 2350 per vertebral body 10. To provide for the derotational function, or the ability to otherwise generate correctional forces that are not aligned with the vertical axis shown in FIG. 23, system 2300 therefore comprises bone anchors having protrusions 2355 that extend laterally relative to the axis of the corresponding anchors 2350 in opposing directions.

Thus, as shown in FIG. 23, some protrusions 2355 may extend laterally of their respective anchors towards one side of the spine and others may extend laterally their respective anchors towards the opposite side, which may allow for generation of derotational forces as needed/desired. This may be accomplished, for example, by coupling a tether/ligament 80—which may comprise a loop tether/ligament or another type of tether/ligament, such as a fixed length tether/ligament—with a protrusion 2355 extending to one side of the spinal column at one level and with a protrusion 2355 extending to the opposite side of the spinal column at an adjacent level.

In some embodiments, protrusions 2355 may be fixed with respect to their corresponding bone anchor 2350. In other words, the protrusions 2355 may be configured to fixedly extend in a given direction from a given bone anchor 2350, which may be accomplished, for example, by forming a hole through any of the saddles previously mentioned from which the protrusion 2355 may fixedly extend. In some such embodiments, the saddle may be rotationally decoupled from the bone engaging portion of the anchor such that the bone engaging portion may be rotatably and/or threadably inserted into the vertebral body 10 without rotating the position of the protrusion 2355.

Alternatively, the protrusions 2355 may be repositionable with respect to a given bone anchor 2350. For example, the protrusion 2355 may be rotatable with the bone anchor 2350 and therefore may be adjusted by rotation of the anchor 2350, or by rotation of just a portion of the anchor, such as a saddle, that protrudes from the vertebral body. In some such embodiments, a plurality of openings may be formed within the saddle/tether engaging portion of the bone anchor 2350 such that the position of the protrusion 2355 may be adjusted by placing it in a desired hole or other opening and then locking it in place. Alternatively, the protrusion 2355 may be fixedly coupled with the protruding/tether engaging portion of the anchor 2350, which itself may be rotatably coupled with the bone engaging portion, which may allow the protrusion 2355 to be rotated about the anchor and locked into place at a desired location.

Figure 24A:
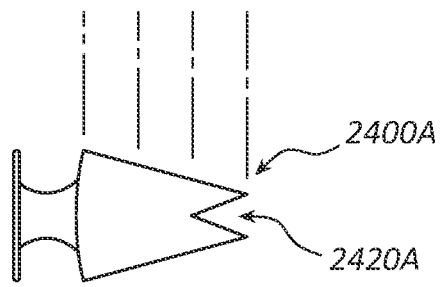
FIGS. 24A-24C depict various bone anchors having inner chamber sizes configured to accommodate distinct bone types.
Figure 24B:
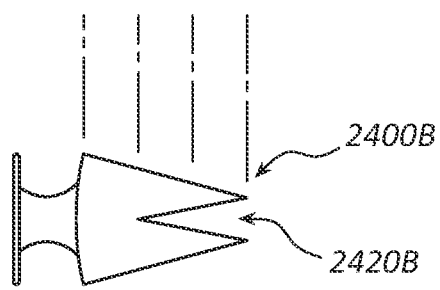
Figure 24C:
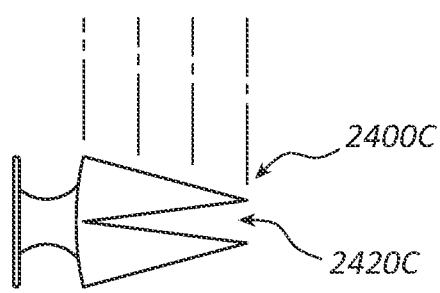

FIGS. 24A-24C depict various bone anchors having different sized inner chambers that may be configured for use in connection with different types of bone and/or patients. For example, bone anchor 2400A comprises an inner chamber 2420A that extends only along about ⅓ of the distal end of the bone engaging portion of the implant 2400A. It is expected that this implant, or other similar implants in which the inner chamber extends along between about ¼ and about ½ of the distal end of the implant, may be particularly useful for patients having osteoporosis or otherwise having weakened bone. It is also thought that, for particularly sever osteoporotic patients and the like, a two-piece implant, such as the implant shown in FIGS. 18 and 19, may be useful. It should be understood that, although not shown in FIGS. 24A-24C, the inner chambers may comprise internal threads or other bone engaging features, as mentioned throughout this disclosure. In addition, it should be understood that these views are cross-sectional and that, typically, the inner chambers would be conical (if configured as shown in the figures) or otherwise decrease in cross-sectional area from the distal to the proximal end of the chamber, at least in part.

FIG. 24B depicts another bone anchor 2400B comprising an inner chamber 2420B that extends only along about ⅔ of the distal end of the bone engaging portion of the implant 2400B. It is expected that this implant, or other similar implants in which the inner chamber extends along between about ½ and about ¾ of the distal end of the implant, may be useful for most typical patients and bone types.

FIG. 24C depicts a bone anchor 24000 comprising an inner chamber 2420C that extends all of the way, or at least substantially all of the way, from the distal end of the bone engaging portion of the implant 24000 to the proximal end that may be coincident with the proximal cortical wall. It is expected that this implant, or other similar implants in which the inner chamber extends along between about ¾ and the full length of the implant, may be useful for stronger bone types.

Figure 25:
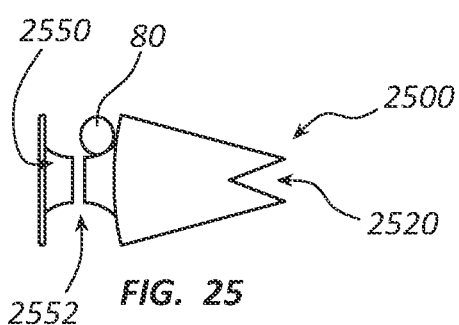
FIG. 25 depicts another bone anchor having a removable cap/tether engagement member according to additional embodiments.

FIG. 25 depicts another bone anchor/implant 2500 having an inner chamber 2520 and a removable cap 2550. Tether/ligament 80 may be coupled with a portion of the implant that protrudes from the bone engaging piece, after which the cap 2550 may be coupled to secure the tether/ligament 80. In some embodiments, the cap 2550 may be coupled by way of adhesives, snap-fit, fasteners, or the like. A gap 2552 between the cap 2550 and the adjacent portion of the anchor may, in some cases, be used to provide a smaller, more secure seat for the tether/ligament 80. Alternatively, this gap 2552 may be fully closed upon completion of coupling of cap 2550 to the anchor.

FIGS. 26A-26E depict various alternative structures for inner chambers (shown in cross-section) that may be useful to draw in and/or compact bone therein, as previously discussed throughout this disclosure. Inner chamber 2620A of bone anchor 2600A comprises a series of steps that result in the cross-sectional area of the chamber 2620A decreasing from the distal end of the anchor 2620A to its proximal end. A flattened proximal end of chamber 2620A, which may comprise, for example, a circular shape (or, alternatively, a rectangular or other desired shape) when viewed along a cross-section taken perpendicular to the primary axis of the anchor 2620A, is provided at the proximal-most region of the inner chamber 2620A. The steps and flattened proximal region may be used to compact bone in a series of distinct regions during use. Although not shown, any of the threads, spikes, or other desired bone engaging features/members may be positioned within chamber 2620A, if desired.

Figure 26A:
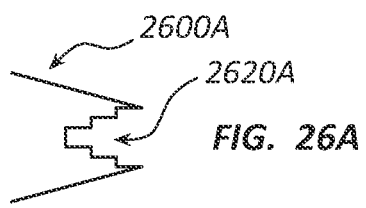
FIGS. 26A-26E depict various alternative configurations for bone anchor inner chambers.
Figure 26B:
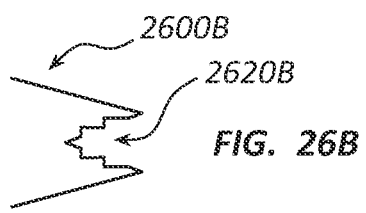

Another example of an inner chamber 2620B of a bone anchor 2600B is shown in FIG. 26B. Inner chamber 2620B is similar to inner chamber 2620A in that it comprises a plurality of discrete steps at which the cross-sectional area decreases from the distal to the proximal end (or increases in the opposite direction). However, unlike chamber 2620A, chamber 2620B comprises a tapering region terminating in a pointed base at the proximal end of the chamber 2620B. Thus, chamber 2620B comprises a cross-sectional area that decreases from the distal to the proximal end by way of both discrete steps and tapers, which may be positioned as desired throughout the chamber 2620B. This may allow for establishing both bone density gradients and discrete regions of bone density variations within the vertebral body in which the anchor 2600B is positioned. Again, any of the threads, spikes, or other desired bone engaging features/members may be positioned within chamber 2620B, if desired.

Figure 26C:
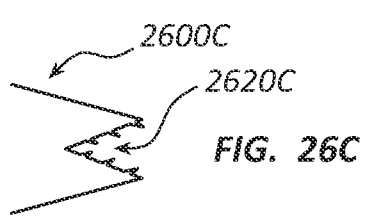
Figure 26D:
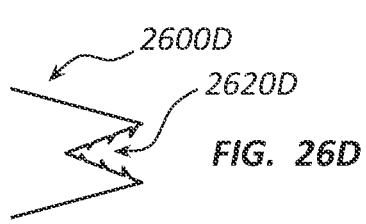
Figure 26E:
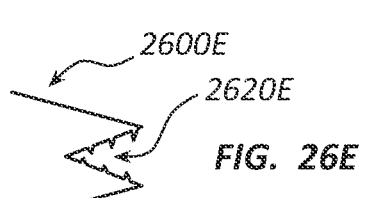

FIGS. 26C-26E depict other examples of bone anchors 2600C-2600E having inner chambers 2620C-2620E, respectively. Each of these inner chambers 2620C-2620E is shown having a simple tapered shape for simplicity and ease of illustration. However, it should be understood that any of these chambers may comprise any combination of steps, tapers, or any of the other features or elements discussed herein or otherwise available to those of ordinary skill in the art. The purpose of these figures, however, is to show how the bone engaging elements may comprise spikes that protrude in a variety of directions. Thus, the spikes of chamber 2620C protrude distally, the spikes of chamber 2620D protrude proximally, and the spikes of chamber 2620E extend perpendicular, or at least substantially perpendicular, to the axis of its respective bone anchor 2600C/2600D/2600E.

Figures 27A, 27B:
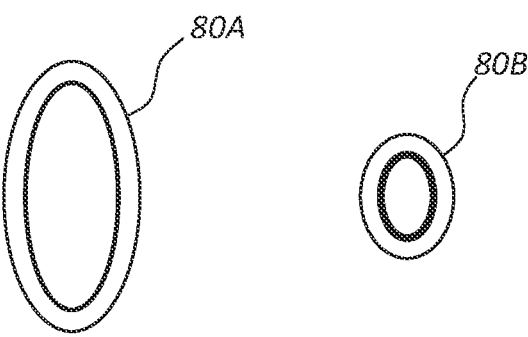
FIG. 27A depicts a resizable ligament in a first configuration.
FIG. 27B depicts the resizable ligament in a second configuration for applying a corrective force to a bone anchor.

FIGS. 27A and 27B depict two configurations of a loop ligament/tether that is configured to shrink in size between an initial configuration 80A shown in FIG. 27A to a subsequent configuration 80B in which the ligament/tether is shorter in length, which may allow for increasing the tension on an associated pair of bone anchors to apply a corrective force to a portion of a patient's spine. In some embodiments, this feature may be accomplished by using heat-shrink tubing or other heat-shrinking materials, which may include thermoplastic materials such as polyolefins, polyesters (such as polyethylene terephthalate), fluoropolymers (such as FEP, PTFE or Kynar), PVC, neoprene, and/or silicone elastomers, for example. In preferred embodiments, one or more heat-shrinkable materials may be incorporated into the ligament/tether, which may be a loop ligament/tether, as shown in FIGS. 27A and 27B, or may be a straight tether/ligament in other embodiments, which preferably shrink to a desired size by use of a patient's body temperature alone.

In this manner, the tether/ligament may be coupled with a pair of adjacent bone anchors in a first, un-shrunk configuration at a first temperature, which may be room temperature or, alternatively, may be a lower temperature, such as a temperature typically requiring refrigeration, and then may be configured to automatically shrink to a desired second, shrunk configuration using only the patient's internal body temperature. Thus, the tether may be configured to shrink to its final size at a temperature of between about 95 and about 100 degrees in some embodiments.

In some embodiments and implementations, a surgeon may select from a variety of different tethers, each of which may be configured to change sizes by a different amount that is predetermined. In this manner, a surgeon may be able to apply different forces simply by selecting between a plurality of tethers/ligaments each having a distinct, predetermined amount of resizing, which may depend upon the materials and configuration of the tether.

FIGS. 28A-28D are simple diagrams of various bone anchors 2800A-2800D illustrating possible configurations of the external surfaces and corresponding thread forms 2815A-2815D of the implants. Each of the inner chambers 2820A-2820D is shown with a simple tapering configuration, again for simplicity's sake, but may vary as desired using one or more of the features/principles disclosed herein.

Figure 28A:
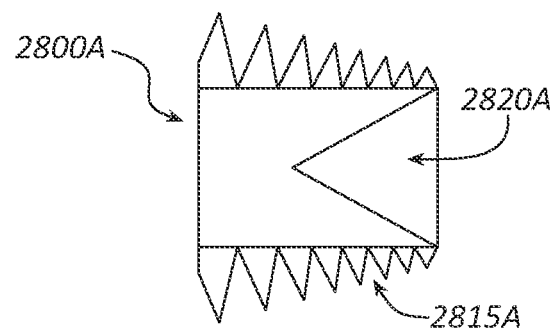
FIGS. 28A-28D depict various alternative configurations for an outer thread form for bone anchors.
Figure 28B:
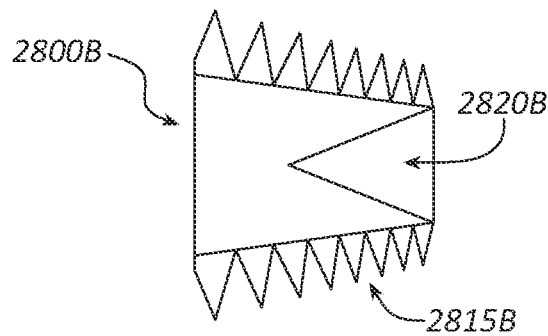
Figure 28C:
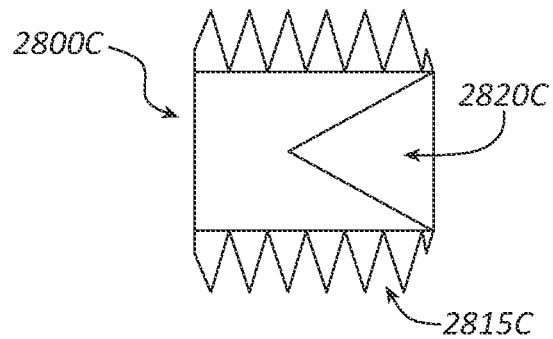
Figure 28D:
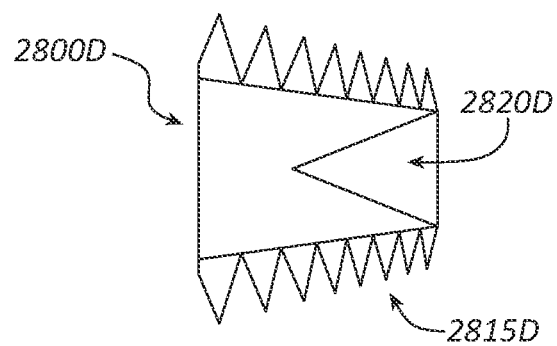

As shown in FIG. 28A, bone anchor 2800A comprises an external thread form 2815A that has a tapering major/outer diameter and a non-tapering minor/inner diameter. Bone anchor 2800B comprises an external thread form 2815B that has a tapering major/outer diameter and a tapering minor/inner diameter. Bone anchor 28000 comprises an external thread form 2815C that has a non-tapering major/outer diameter and a non-tapering minor/inner diameter. And finally, bone anchor 2800D comprises an external thread form 2815D that has a tapering major/outer diameter and a tapering minor/inner diameter.

Figure 29A:
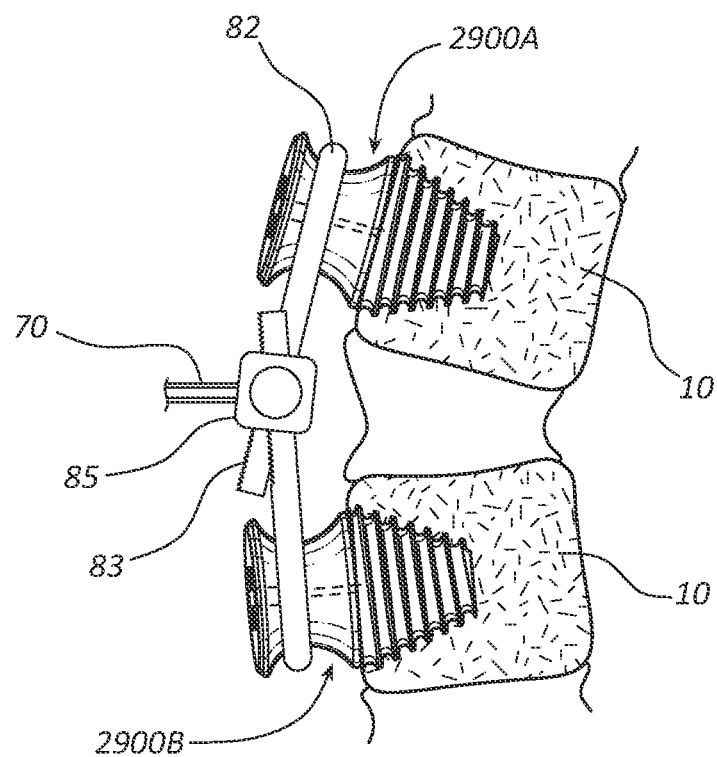
FIGS. 29A and 29B are perspective views of a system for spinal deformity correction comprising a selectively tensionable ligament according to some embodiments during a method for spinal correction using the system.
Figure 29B:
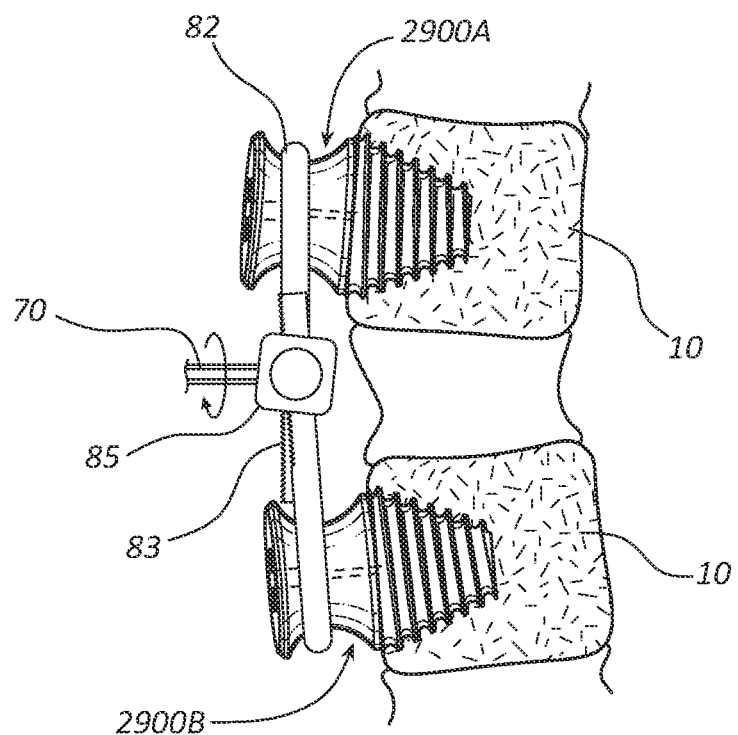

FIGS. 29A and 29B depict yet another example of a system for spinal deformity correction. This system is shown with two adjacent bone anchors, namely, bone anchor 2900A and bone anchor 2900B, positioned in two adjacent vertebral bodies 10. This system also comprises a straight ligament 82 that is configured to be formed into a loop and shortened manually between the first configuration shown in FIG. 29A and the second configuration shown in FIG. 29B. More particularly, a means for selectively shortening tether/ligament 82, such as ratchet mechanism 85, may be used, along with a suitable instrument 70, to shorten the length of tether 82 and thereby increase the force between the adjacent anchors 2900A and 2900B, as illustrated in FIG. 29B.

A series of teeth 83 may be formed along one or both ends of tether 82, which teeth 83 may cooperate with a corresponding set of ratcheting teeth within mechanism 85. Alternatively, teeth or other engaging features may only be present within mechanism 85. As another possible alternative embodiment, instrument 70 may be configured to simply decrease the size of an opening through which one or both ends of tether 82 extend, in which case a user may, for example, pull one end of tether 82 through mechanism 85 and then tighten/decrease the size of the aforementioned opening.

FIGS. 30A-30C depict still another example of a system for spinal deformity correction. This system is again shown with two adjacent bone anchors, namely, bone anchor 3000A and bone anchor 3000B, positioned in two adjacent vertebral bodies 10. This system also comprises a straight ligament 80 that is configured to be formed into a loop and shortened manually between the first configuration shown in FIG. 30A and the second configuration shown in FIG. 30B.

However, this system may involve one or more additional steps not required in system 2900.

In particular, system 3000 comprises a temporary set of rods 75A and 75B, which may each be coupled with a respective bone anchor 3000A/3000B. Rods 75A and 75B may independent components, or may be part of an integrated assembly or instrument that is used to tension the anchors 3000A/3000B temporarily until, as shown in FIGS. 30B and 30C, tether 80 may be used to more permanently apply the corrective force initially and temporarily applied by the temporary assembly/components.

One or more components may extend between the temporary rods 75A/75B, such as telescoping or otherwise interconnecting arms. In the depicted embodiment, these elements may comprise a single, temporary tether 82, as shown in FIG. 30B, which may be tensioned to tension anchors 3000A and 3000B via rods 75A and 75B by way of, for example, ratchet mechanism 85. This mechanism may be actuated to shorten the length of tether 82, or another interconnecting piece or pieces, by way of a suitable instrument 70 or another means for selectively shortening a tether/ligament 82.

As was the case with the system depicted in FIGS. 29A and 29B, a series of teeth 83 may be formed along one or both ends of tether 82, which teeth 83 may cooperate with a corresponding set of ratcheting teeth within mechanism 85. Again, alternatively, teeth or other engaging features may only be present within mechanism 85 or any of the other features, elements, and/or instruments disclosed herein may be used instead.

As shown in FIG. 30B, once rods 75A/75B have been tensioned, a permanent ligament 80 may be extended past tether/arms 82 and onto the respective saddles or other ligament engaging members of anchors 3000A and 3000B. Once this has taken place, each of the temporary elements may be removed. In other words, using the exemplary embodiment of FIGS. 30A-30C, rods 75A and 75B, along with tether/arms 82 and the instrument used to provide the temporary tensioning, may be removed to allow ligament 80 to provide the permanent corrective force to anchors 3000A and 3000B.

It should be understood that a wide variety of alternative features, embodiments, and implementations will be apparent to those of ordinary skill in the art after having received the benefit of this disclosure. For example, in embodiments and implementations in which the means for coupling rods 75A and 75B comprises a removable ligament rather than fixed arms, the removable ligament (element 82 in FIGS. 30A and 30B) may simply be slid onto the adjacent bone anchors rather than using a separate ligament/tether 80.

Figure 31A:
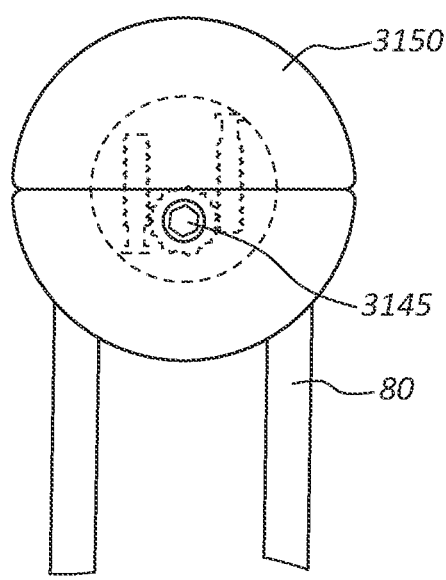
FIG. 31A depicts a selectively expandable ligament saddle according to some embodiments in a first configuration.
Figure 31B:
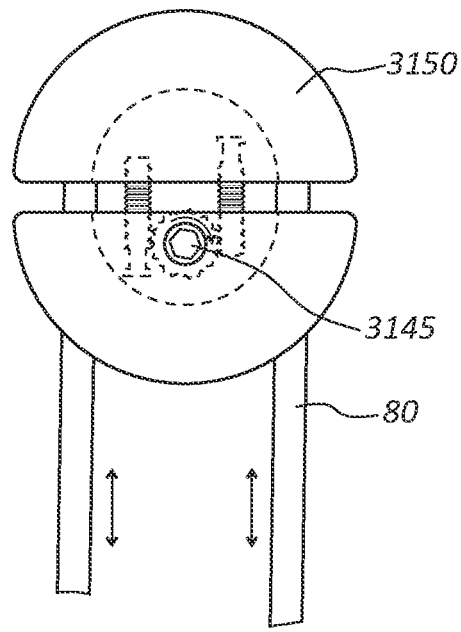
FIG. 31B depicts the selectively expandable ligament saddle of FIG. 31A in a second, expanded configuration.

FIGS. 31A and 31B depict an example of an expandable saddle 3150 or other means for increasing a size of a saddle or other tether engagement member. As shown in FIG. 31A, saddle 3150 may comprise two pieces, one being movable relative to the other, which may allow a surgeon/practitioner to adjust the height of the surface of the saddle 3150 on which the tether 80 is positioned, which may increase the distance to an adjacent bone anchor and/or saddle and thereby increase the force on the ligament/tether 80. This may be accomplished in a number of ways. In the depicted embodiment, a gear having a keyed engagement structure 3145 may be used. The keyed engagement structure 3145 may allow for coupling with a suitable driver or other instrument used to, via the gear, drive a threaded shaft to separate the two pieces of the saddle 3150, as shown in FIG. 31B.

Figure 32A:
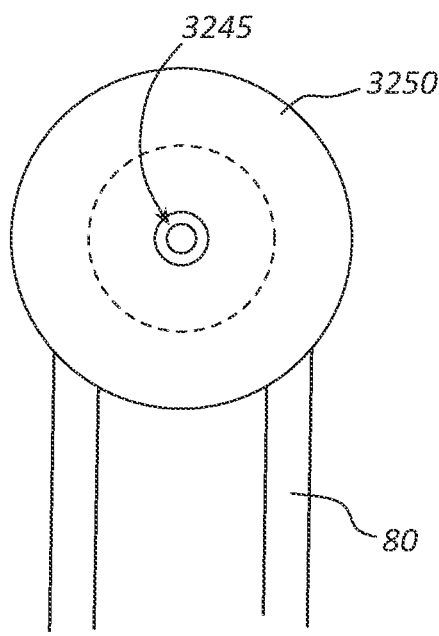
FIG. 32A depicts a selectively expandable ligament saddle having an expandable chamber according to some embodiments in a first configuration.
Figure 32B:
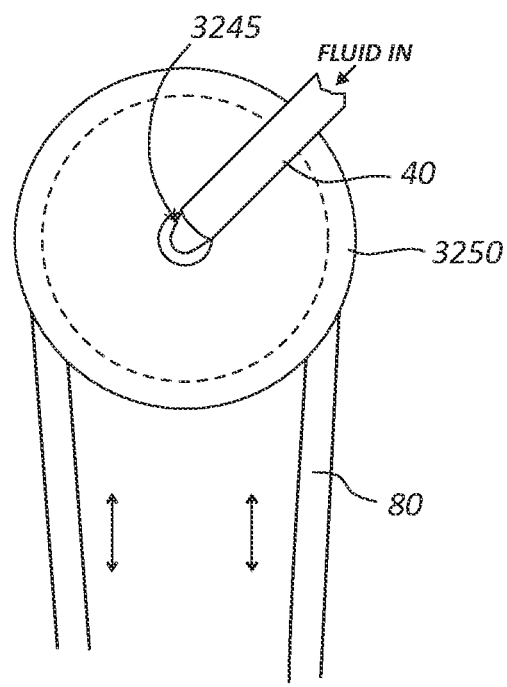
FIG. 32B depicts the selectively expandable ligament saddle of FIG. 32A in a second, expanded configuration.

FIGS. 32A and 32B depict another example of an expandable saddle 3250 or other means for increasing a size of a saddle or other tether engagement member. As shown in FIG. 32A, saddle 3250 may be defined, at least in part, by an expandable chamber, which may be fluidly coupled with a port 3245, which is preferably automatically resealable. Port 3245 may be selectively opened to introduce a gas or another fluid, as shown in FIG. 32B, to expand the size of the expandable chamber and thereby increase the tension on tether/ligament 80. Any suitable instrument comprising a tube 40 or the like may be used to introduce the fluid, which may comprise a syringe in some embodiments. In some embodiments, the syringe may be inserted through, for example, a self-healing/sealing port, which may be made up of, for example, silicone and/or rubber, such as ethylene propylene diene terpolymer (EPDM) foam rubber.

Figure 33:
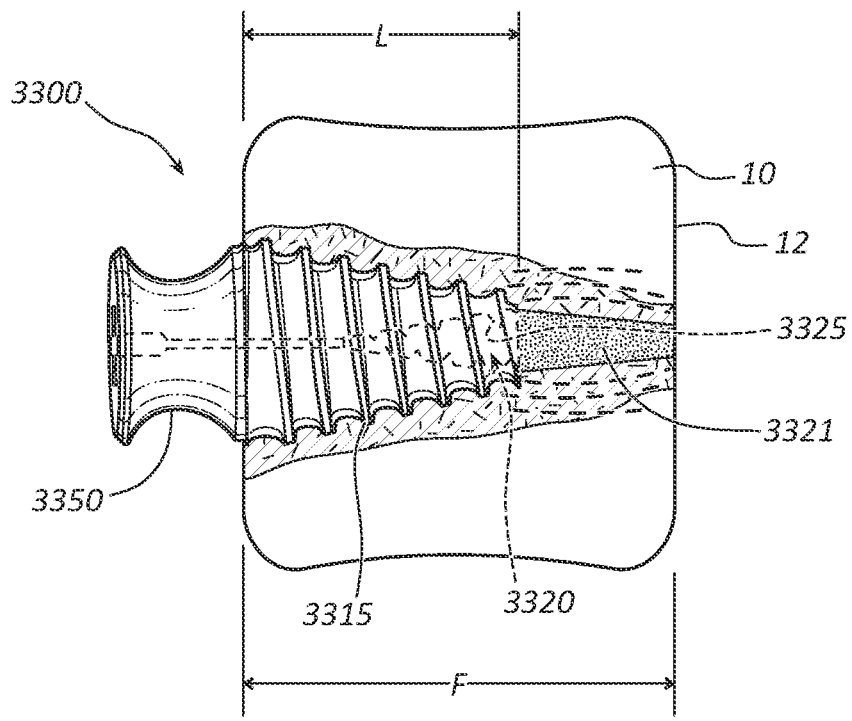
FIG. 33 depicts a vertebral bone anchor during a method for forming a distal, compressed bone region to obtain functional bicortical purchase.

FIG. 33 illustrates another embodiment of a bone anchor 3300 after a method for installation of the bone anchor 3300 within a vertebral body 10. Bone anchor 3300 again comprises a tether engagement member 3350, which in the depicted embodiment comprises a saddle configured to engage a tether or another preferably flexible coupling member.

In addition, bone anchor 3300 comprises an inner chamber 3320, which may comprise inner threads 3325. As previously mentioned, in other embodiments, other types of bone engaging protrusions and/or features may be provided within inner chamber 3320, such as a plurality of spikes or the like, to facilitate drawing in and compacting cancellous bone into the chamber 3320. Such features 3325 may also facilitate fixation of such bone after healing, as discussed below.

Bone anchor 3300 may further comprise any of the features herein in connection with other embodiments, such as an external thread form 3315 an inner chamber 3320 having a reverse taper, either partial or full, and/or a profile that increases in cross-sectional area, at least in part, from a proximal end of the inner chamber 3320 to a distal end of the inner chamber 3320. In addition, as previously mentioned, some embodiments may be configured to provide a force differential between the internal and external threads or other bone engaging features.

Bone anchor 3300 is shown in FIG. 33 performing a method facilitated by the structure of the anchor 3300 in which bone is compacted within the inner chamber 3320 and, as bone anchor 3300 is advanced, compresses bone in front of (distally of) the bone anchor 3300 to create a compressed bone region 3321 that extends out of inner chamber 3320 along the axis of bone anchor 3300.

In the depicted method, compressed bone region 3321 has contacted the distal cortical wall 12 of the vertebral body 10. By extending the compressed bone region 3321 sufficiently to contact and, in some implementations, further compress against, the distal cortical wall 12, bicortical fixation can be achieved by bone anchor 3300 without penetration of the distal cortical wall 12. This provides a significant increase in safety, as penetrating the distal cortical wall 12 with known bicortical screws has the potential to damage vital blood vessels, spinal column features, or other body tissues within this sensitive region of the human body.

As also depicted in FIG. 33, the methodology of compressing and advancing cancellous bone in front of the anchor 3300 to form a compressed bone region 3321 and/or to achieve bicortical fixation without penetrating the distal cortical wall 12 increases the functional length of the implant/anchor 3300. More particularly, as shown in FIG. 33, the anchor 3300 comprises a length L, which comprises the length of the physical makeup of the implant within the vertebral body 10, and a functional length F, which is longer than length L (and, as mentioned above, in this particular example extends all the way across the vertebral body 10 to achieve bicortical fixation) due to the formation of compressed bone region 3321. This extension of the functional length of the implant results in greater fixation of the bone anchor 3300 within the vertebral body 10, decreases the chances of the bone anchor 3300 becoming dislodged, toggling, and/or loosening within the vertebral body 10, and increases the forces that can be placed on the saddle 3350 without damaging the fixation rather than applying the force to the vertebral body 3300 and/or spinal column for correction of a spinal deformity.

Although the compressed bone region 3321 is shown extending to and contacting the distal cortical wall 12 in this embodiment, this need not be the case in all embodiments, as will be more apparent after considering later figures. Indeed, there may be benefit to extending the functional length of an implant without obtaining bicortical fixation. Thus, in preferred implementations, the compression may result in between about 2 mm and about 15 mm of distal compressed bone region and/or increased functional length, which length is represented by distance F minus distance L (the actual length L of the implant subtracted from the overall functional length F). More preferably, the compression may result in between about 5 and about 15 mm—or in other cases between about 5 and about 10 mm—of distal compressed bone region and/or increased functional length.

However, the use of functional bicortical purchase/bicortical fixation using this effect may depend upon, the quality of the bone, the size of the bone, and/or the size/dimensions of the implant. Thus, if the bone quality is high, the length of the distal compressed bone/increased functional length may be reduced and/or bicortical fixation may not be needed.

Thus, in some cases it may be preferable to select the amount of distal compressed bone/increased functional length as a percentage of the length of the implant itself. Thus, in some implementations, the increase in functional length of the bone anchor due to the distal compressed bone region may be between about 10% and about 40%. In some such implementations, the increase in functional length of the bone anchor due to the distal compressed bone region may be between about 20% and about 40%, or between about 20% and about 30%.

As further illustrated in FIG. 33, negative charges are induced by the deformation and compression of bone along the compressed bone region 3321, which may further stimulate healing of the compressed bone region 3321, providing further strength to the resulting fixation of bone anchor 3300.

To summarize, the fixation of the bone anchor 3300 may be enhanced by a series of steps and/or features, including the length, width, tapering profile, inner chamber 3320, bone engaging protrusions and/or features 3325, etc., along with the compressed bone region 3321, which may, as mentioned above, be compressed against the distal cortical wall 12 in some cases to result in abutment and/or mechanical fixation along the distal cortical wall 12 to achieve bicortical fixation without requiring potentially dangerous penetration of the distal cortical wall. These steps/features may increase the fixation length of the anchor/implant and/or may distribute/dissipate corrective forces applied to the anchor/implant over the entire vertebral body 10.

Figure 34:
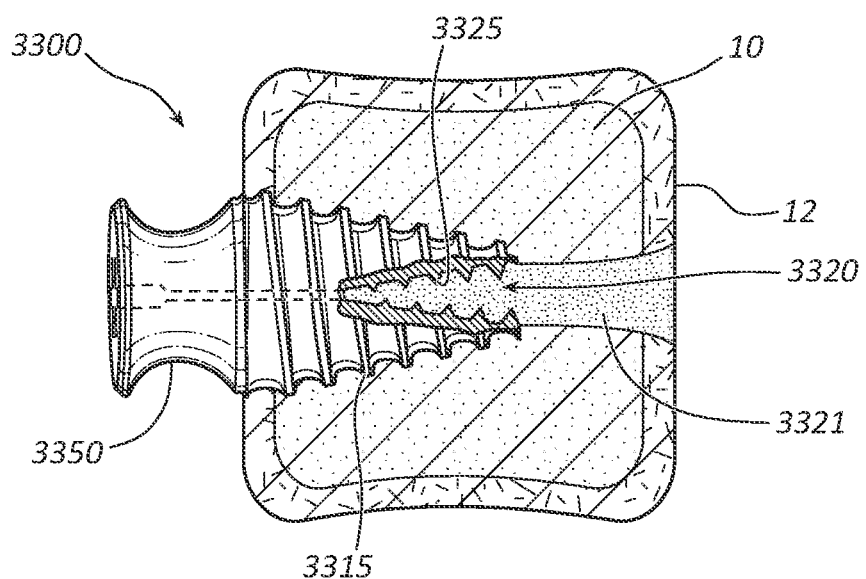
FIG. 34 depicts the vertebral bone anchor of FIG. 33 following healing of the compressed bone region.

FIG. 34 illustrates implant 3300 following healing. Typically, the healing/fixation depicted in this figure will occur gradually over the course of perhaps 3-6 months, although there are variables involved that may result in quicker or more prolonged healing. FIG. 34 illustrates how bone compressed bone region 3321 has solidified to form a solidified bone shaft that has attached to the distal cortical wall 12 of vertebral body 10 and has extended slightly above and below the bone shaft 3321 along the distal cortical wall 12.

The fixation of compressed bone region/bone shaft 3321 may be enhanced by several factors/features/steps, including engagement of internal threads or other bone engagement features 3325 within the inner chamber 3320, the exposure of negative charges around the disrupted bone trabeculae of the bone resulting from the compression of bone distal of the bone anchor 3300 during insertion, along with liberated local growth factors and/or molecular signals in this region in some cases. These factors preferably result in a mechanical device that favorably exploits the local biology to improve function and augment fixation over time to inhibit implant loosening and/or failure. In some embodiments and implementations, this bicortical fixation may provide strength and/or reduction in toggle, loosening, and/or failure that is equal to, or in some cases greater than, that provided by a traditional bicortical screw obtaining bicortical purchase through the same vertebral body.

Figure 35:
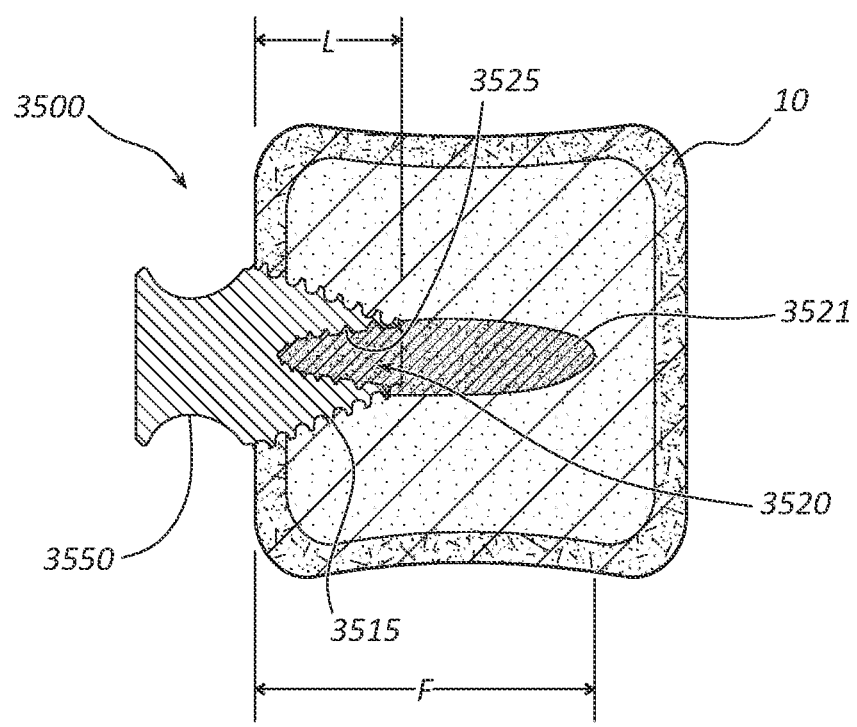
FIG. 35 depicts another vertebral bone anchor during a method for forming a distal, compressed bone region to extend the functional fixation length of the anchor without obtaining functional bicortical purchase.

FIG. 35 illustrates still another embodiment of a bone anchor 3500 after performing a method for fixation of the anchor 3500 within a vertebral body 10. Bone anchor 3500 again comprises a tether engagement member 3550, which in the depicted embodiment comprises a saddle configured to engage a tether or another preferably flexible coupling member.

Bone anchor 3500 further comprises an inner chamber 3520, which may comprise inner threads 3525 or, in other embodiments, another type of bone engaging protrusions and/or features 3525 to facilitate drawing in, compacting, and/or fixation/attachment of cancellous bone into the chamber 3520.

Bone anchor 3500 may further comprise any of the features herein in connection with other embodiments, such as an external thread form 3515, inner chamber 3520 having a reverse taper, either partial or full, and/or a profile that increases in cross-sectional area, at least in part, from a proximal end of the inner chamber 3520 to a distal end of the inner chamber 3520.

However, the method and anchor 3500 of FIG. 35 differs from that of FIG. 33 in a few important ways. First, the bone of the vertebral body 10 in FIG. 35 is harder, denser, and/or healthier. As such, a surgeon may prefer to use a shorter bone anchor 3500 and/or may prefer to, as shown in the figure, extend the bone anchor 3500 a lesser distance relative to the width of the vertebral body 10. Thus, bone anchor 3500 is shown extending (length L) less than halfway across the width of the vertebral body. However, as discussed below in greater detail, the effective fixation length provided by the compressed bone region 3521 (length F) extends beyond the halfway point of the vertebral body 10. To be clear, this is just an example. Those of ordinary skill in the art will appreciate that the bone anchor 3500 may still extend to or beyond the midpoint of the vertebral body even if the intent is to avoid extending the compressed bone region 3521 to the distal cortical wall.

Thus, bicortical fixation with the distal cortical wall may not be needed and/or readily achievable. Still, bone anchor 3500 is shown in FIG. 35 performing a method facilitated by the structure of the anchor 3500 in which bone is, like the method shown in FIG. 33, compacted within the inner chamber 3520 and, as bone anchor 3500 is advanced, compressed distally of the bone anchor 3500 to create a compressed bone region 3521 that extends out of inner chamber 3520 along the axis of bone anchor 3500 to improve fixation and/or reduce the chances of toggling and/or failure.

As also depicted in FIG. 35, the methodology of compressing and advancing cancellous bone in front of the anchor 3500 to form a compressed bone region 3521 increases the functional length of the implant/anchor 3500, despite the fact that, unlike the method depicted in FIG. 33, bicortical fixation is not achieved. Thus, the anchor 3500 comprises a length L, which comprises the length of the physical makeup of the implant within the vertebral body 10, and a functional length F, which is longer than length L due to the formation of compressed bone region 3521. Again, this results in greater fixation of the bone anchor 3500 within the vertebral body 10, decreases the chances of the bone anchor 3500 becoming dislodged, toggling, and/or loosening within the vertebral body 10, and increases the forces that can be placed on the saddle 3550 without damaging the fixation rather than applying the force to the vertebral body 3500 and/or spinal column for correction of a spinal deformity.

Figure 36:
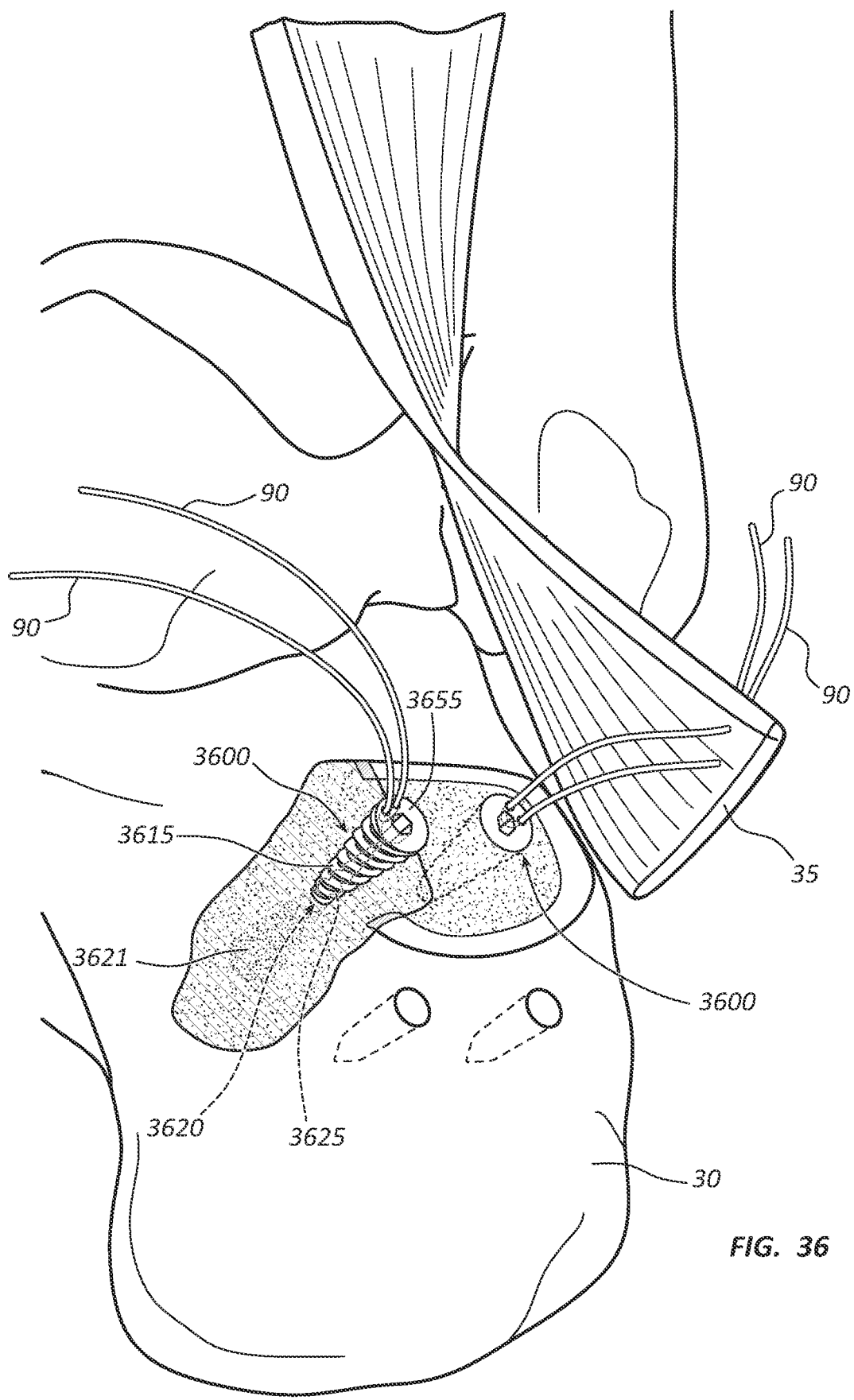
FIG. 36 depicts a bone anchor with sutures used during a method for tendon repair.

FIG. 36 illustrates an alternative embodiment and implementation of a system and method in which one or more bone anchors 3600 are used in a different type of bone and for a different type of procedure. In particular, bone anchor 3600 is shown being positioned in a calcaneal bone 30 in a procedure to repair an Achilles tendon 35. It should be understood, however, that similar anchors may be used in other types of bone and/or for other types of surgeries, such as repair of other tendons or ligaments.

In the embodiment/implementation of FIG. 36, anchor 3600 also comprises an external thread form 3615, along with an inner chamber 3620, which may comprise inner threads 3625 or, in other embodiments, another type of bone engaging protrusions and/or features 3625 to facilitate drawing in, compacting, and/or fixation/attachment of cancellous bone into the chamber 3620.

Although smaller than the vertebral anchors discussed above, bone anchor 3600 may further comprise any of the other features herein in connection with other embodiments, such as an inner chamber 3620 having a reverse taper, either partial or full, and/or a profile that otherwise increases in cross-sectional area, at least in part, from a proximal end of the inner chamber 3620 to a distal end of the inner chamber 3620, in addition to, in some embodiments, a force differential between the internal and external threads or other bone engaging features of the anchor 3600.

However, in some embodiments, bone anchor 3600 may be configured to be recessed fully into bone 30 without providing a protruding engagement member, as was commonly the case with various other embodiments discussed above. Still, as discussed below, some embodiments used for tendon repair may comprise a protruding engagement member configured to couple with a suture, for example, or another flexible coupling member.

In the depicted embodiment, one or more sutures 90 are coupled with each bone anchor 3600 to allow them to be coupled with an adjacent tendon 35 (Achilles, in this case). Sutures 90 may be pre-coupled with anchor 3600. Alternatively, as discussed below, one or more coupling features may be provided at a proximal end to allow a surgeon to selectively couple sutures 90, or another preferably flexible coupling member, with the bone anchor 3600. Any number of sutures may be used as needed, and as may be available due to space constraints. However, in preferred embodiments, 1-6 sutures may be coupled with bone anchor 3600. In more preferred embodiments, 2-5 sutures may be coupled with each bone anchor 3600.

For example, in some embodiments a proximal cap 3655 may be used. Sutures 90 may be pre-coupled with cap 3655, which cap 3655 may be, for example threadably or otherwise selectively coupled with the body of the bone anchor 3600. Thus, for example, in some embodiments, the body of bone anchor 3600 may comprise a threaded opening at the proximal end to receive cap 3655, similar to embodiments discussed above in the context of spinal applications. Alternatively, cap 3655 may be an integral part of the body of bone anchor 3600.

In addition, as also depicted in FIG. 36, bone anchor 3600 is configured to, and has been installed so as to, form a compressed bone region 3621 along the axis of bone anchor 3600 in the region in front of (distally) the bone anchor 3600. In some implementations, compressed bone region 3621 may be advanced so as to contact cortical bone, such as against a cortical wall opposite from the entry point of the bone anchor 3600. However, in other implementations, the effective fixation length may, as mentioned above, be sufficiently lengthened by use of the compressed bone region 3621 so as to provide significant benefit without contacting the compressed bone region 3621 with cortical bone.

Figure 37A:
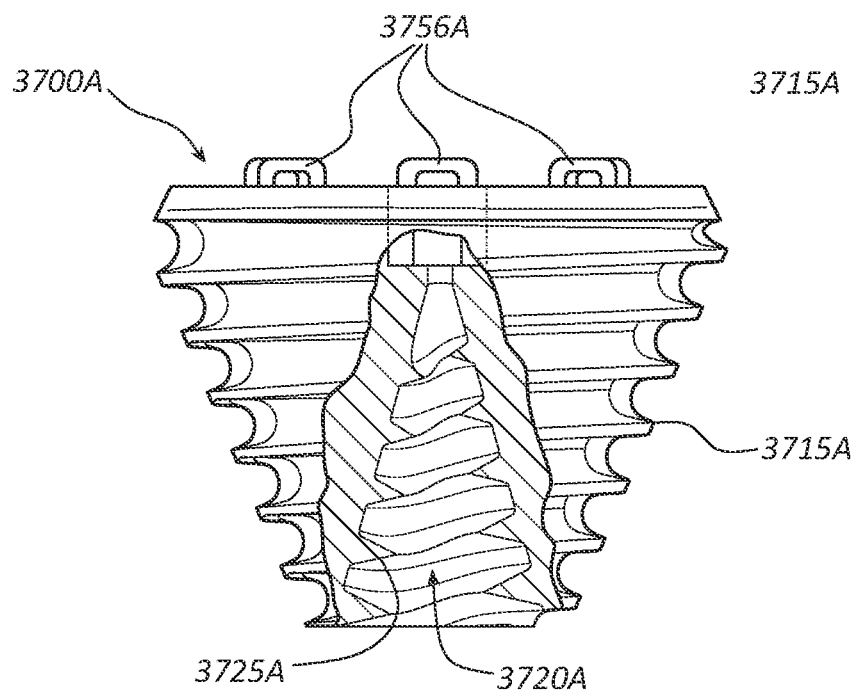
FIG. 37A depicts another bone anchor with means for selectively coupling sutures or another flexible coupling member for repair of a ligament, tendon, or the like, wherein the means for coupling a flexible coupling member protrudes from a proximal portion of the anchor.
Figure 37B:
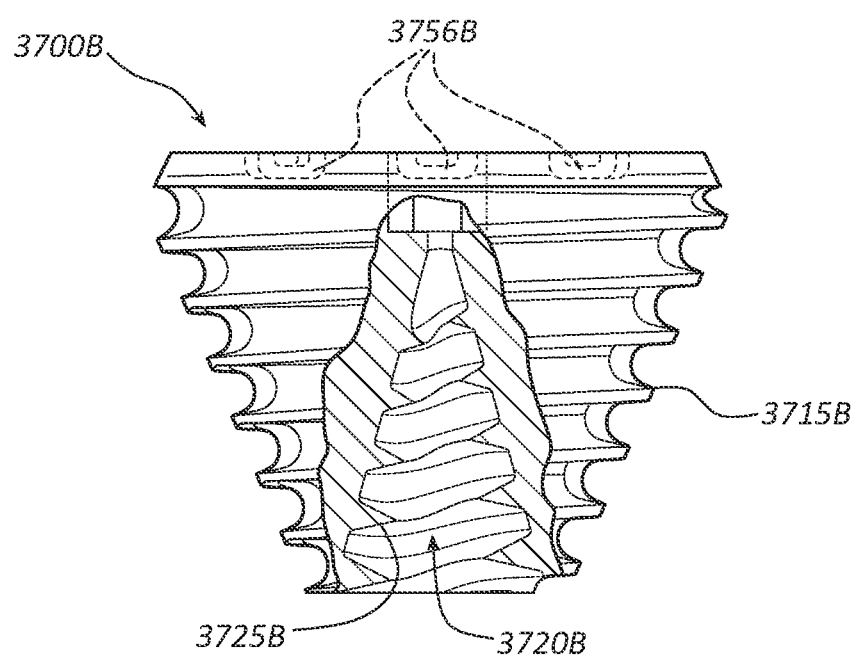
FIG. 37B depicts an alternative bone anchor having means for selectively coupling sutures or another flexible coupling member that are recessed within a proximal portion of the anchor.

FIGS. 37A and 37B depict additional embodiments of bone anchors, 3700A and 3700B, respectively, configured for coupling with sutures, bands, wires, or other preferably flexible members for use in applying a force to a bone within which the bone anchor 3700A/3700B is positioned.

With respect to bone anchor 3700A, a plurality of protruding coupling members 3756A are formed at the proximal end. Protruding coupling members 3756A comprise eyelets, although in alternative embodiments such coupling members 3756A may comprise hooks, saddles, rivets, screws, bolts, or the like.

By contrast, bone anchor 3700B comprises a plurality of recessed coupling members 3756B, which are also formed at the proximal end, although they protrude inwards with respect to the body of the bone anchor 3700B. In the depicted embodiment, these recessed coupling members 3756B comprise internal loops or tunnels through which a suture or other flexible coupling member may be inserted.

However, in alternative embodiments, a recessed region may be formed at the proximal end of the bone anchor 3700B to allow the recessed coupling members 3756B to extend distally, avoid protruding from the proximal end of the bone anchor 3700B, and allow a surgeon or practitioner to couple sutures or other flexible members to one or more of the recessed coupling members 3756B. Again, although recessed eyelets are shown in the depicted embodiment, a variety of alternative recessed coupling members 3756B are contemplated, such as hooks, screws, bolts, pins, and the like. It should be understood that any of these elements may alternatively be used in coupling members that protrude from the proximal end of the bone anchor as well.

With respect to both bone anchor 3700A and bone anchor 3700B, it is contemplated that the respective coupling members 3756A/3756B may, in some cases, be part of a cap that may be threadably coupled or otherwise coupled with the body of the respective bone anchor 3700A/3700B, as mentioned above.

Otherwise, bone anchors 3700A and 3700B may be similar to any of the bone anchors disclosed elsewhere herein. For example, in the depicted examples, bone anchors 3700A/3700B each comprises respective outer threads 3715A/3715B, a respective inner chamber inner chamber 3720A/3720B with respective inner threads 3725A/3725B (again, such inner threads may be replaced with other bone engaging features as desired) that has a reverse taper (again, this may be omitted or replaced with an inner chamber that decreases in cross-sectional volume, at least in part, from the distal to the proximal end thereof in another manner).

Figure 38:
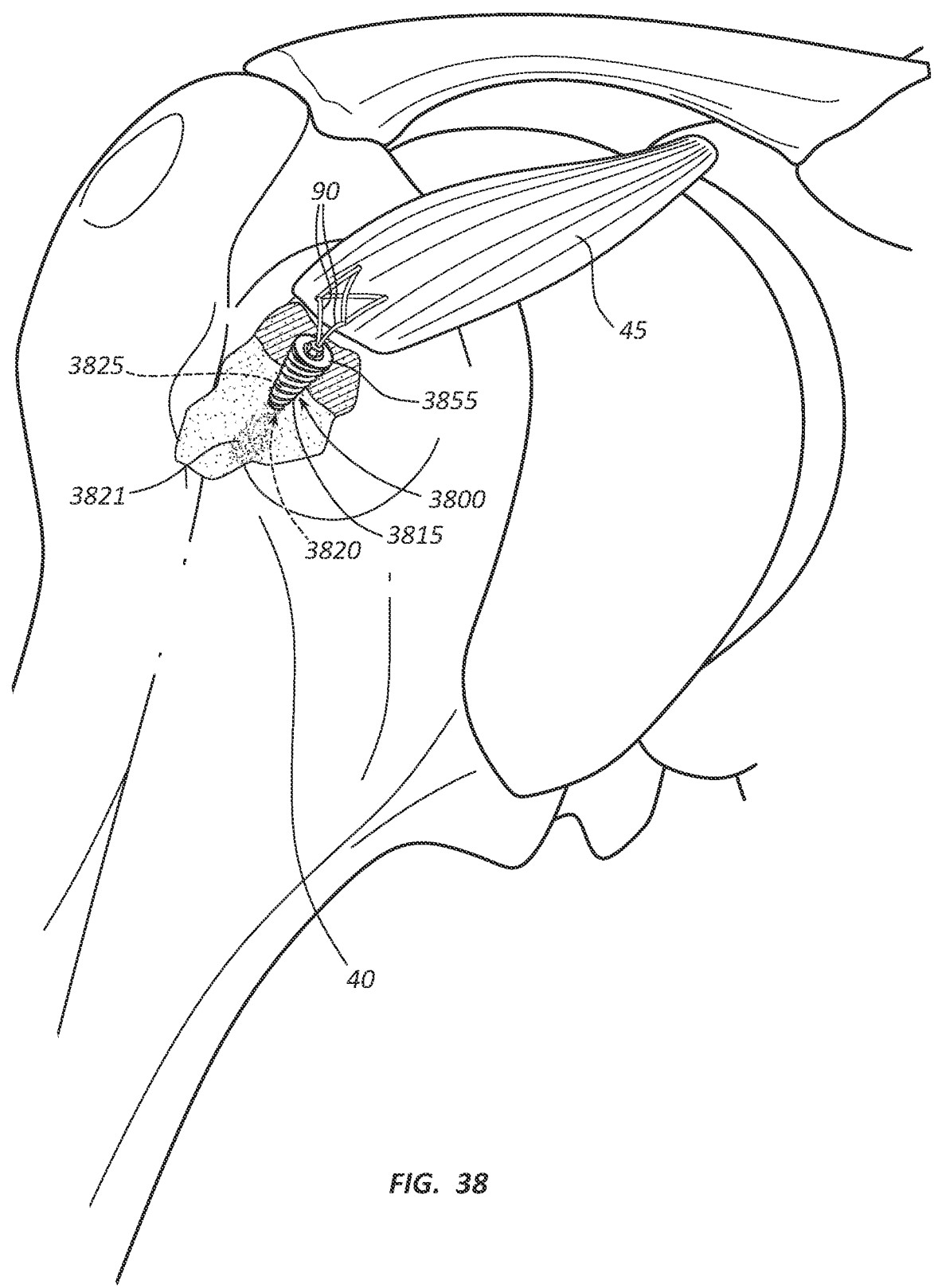
FIG. 38 depicts a bone anchor with sutures used during another method for tendon repair.

FIG. 38 illustrates yet another alternative embodiment and implementation of a method in which a bone anchor 3800 is used in a different type of bone and for a different type of procedure. In this case, bone anchor 3800 is shown positioned in a humerus bone 40 in a procedure to repair a rotator cuff. Thus, bone anchor 3800 is coupled with sutures 90 that are coupled with a rotator cuff tendon 45.

In the embodiment/implementation of FIG. 38, anchor 3800 again comprises an external thread form 3815, along with an inner chamber 3820, which may comprise inner threads 3825 or, in other embodiments, another type of bone engaging protrusions and/or features 3825 to facilitate drawing in, compacting, and/or fixation/attachment of bone into the chamber 3820.

Bone anchor 3800 may further comprise any of the other features herein in connection with other embodiments, such as an inner chamber 3820 having a reverse taper, either partial or full, and/or a profile that otherwise increases in cross-sectional area, at least in part, from a proximal end of the inner chamber 3820 to a distal end of the inner chamber 3820, in addition to, in some embodiments, a force differential between the internal and external threads or other bone engaging features of the anchor 3800.

Bone anchor 3800 may be configured to be fully recessed into the bone 40 similar to bone anchor 3600. In this manner, only sutures 90 may extend from the proximal end of bone anchor 3600.

As with bone anchor 3600, sutures 90 may be pre-coupled with anchor 3800 or, alternatively, one or more coupling features may be provided at a proximal end to allow a surgeon to selectively couple sutures 90, or another preferably flexible coupling member, with the bone anchor 3800. Again, any number of sutures may be used as needed for each bone anchor 3800, for example between 1-6 sutures, or between 2-5 sutures.

In addition, in some embodiments, a proximal cap 3855 may be used, which may be either integrally formed with or selectively coupleable, such as threadedly coupled, with the body of bone anchor 3800. Further, sutures 90 may be pre-coupled with cap 3855 or features may be provided to facilitate manual coupling of sutures 90 or other similar elements, as desired, similar to those described above in connection with bone anchors 3700A and 3700B, for example.

In addition, as also depicted in FIG. 38, bone anchor 3800 is configured to, and has been installed so as to, form a compressed bone region 3821 along the axis of bone anchor 3800 in the region in front of (distally) the bone anchor 3800. Again, in some implementations, compressed bone region 3821 may be advanced so as to contact cortical bone, such as against a cortical wall opposite from the entry point of the bone anchor 3800. However, in other implementations, the effective fixation length may, as mentioned above, be sufficiently lengthened by use of the compressed bone region 3821 so as to provide significant benefit without extending the compressed bone region 3821 into a cortical bone and/or distal bone wall.

Figure 39:
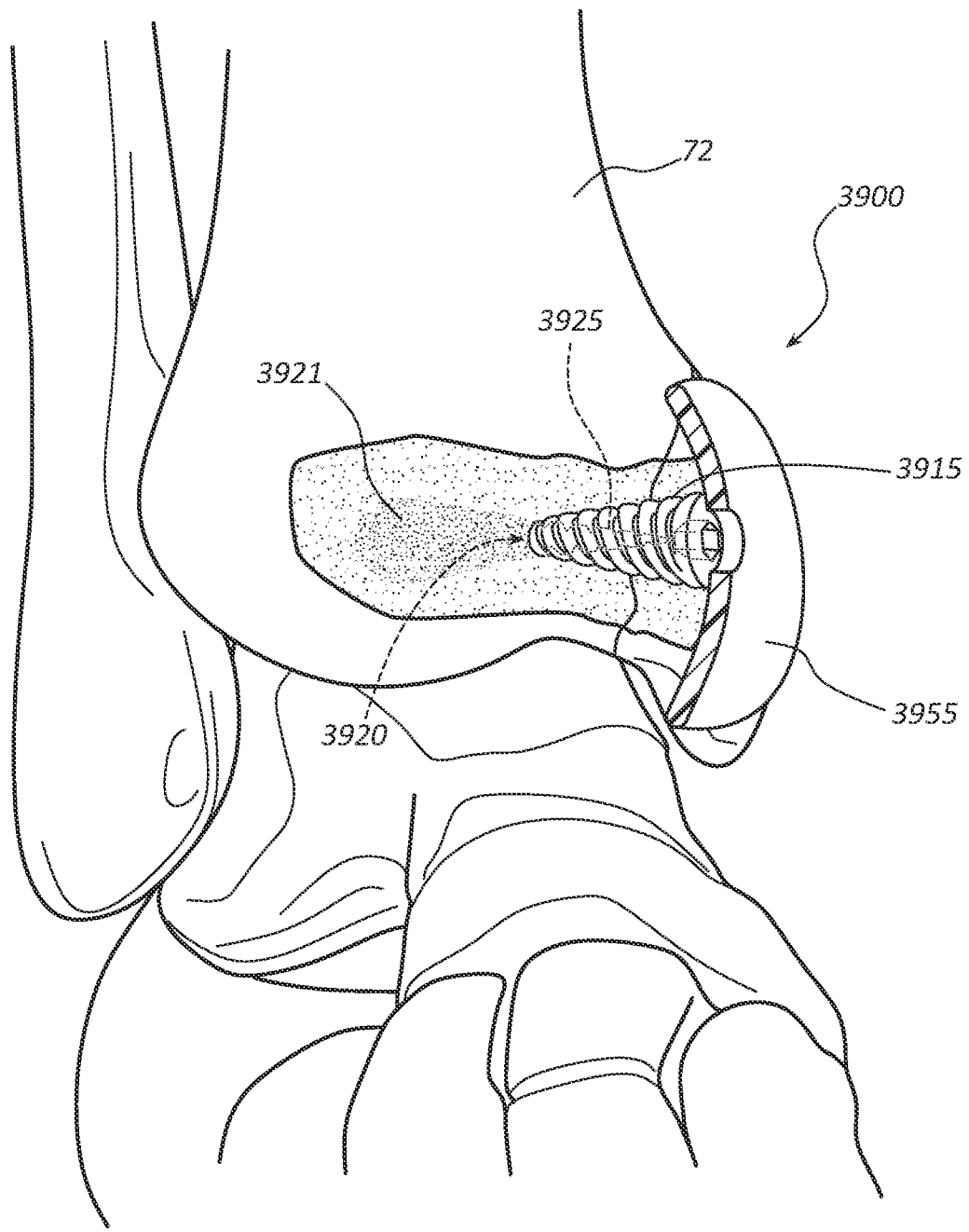
FIG. 39 depicts a bone anchor used during a method for repairing a bone fracture.

FIG. 39 illustrates another embodiment of a bone anchor 3900. In this embodiment, bone anchor 3900 is used to repair a bone fracture, namely, a medial malleolus fracture of the ankle/tibia bone 72. Thus, FIG. 39 depicts bone anchor 3900 having been advanced past the point of fracture. In preferred implementations, bone anchor 3900 is advanced such that at least half of the length of the bone anchor 3900 has been advanced past the point of fracture. It may therefore be useful to form bone anchor 3900 to be longer and/or thinner than most, if not all, of the other embodiments disclosed herein.

To inhibit splintering of the proximal bone piece of the fracture, bone anchor 3900 is provided with a proximal cap 3955, which in this case comprises a convex plate or umbrella flange configured to engage with the proximal surface of the ankle/tibia bone 72. In some embodiments, this cap 3955 may be removable such that, upon healing, the cap can be unscrewed or otherwise removed from the body of the bone anchor 3900.

One or more other features described herein in connection with other embodiments may also be provided with respect to bone anchor 3900. For example, anchor 3900 may comprise an external thread form 3915, an inner chamber 3920, which may comprise inner threads 3925 or another type of bone engaging protrusions and/or features 3925 to facilitate drawing in, compacting, and/or fixation/attachment of bone into the chamber 3920.

Similarly, as shown in FIG. 39, bone anchor 3900 has been installed so as to grind and/or dislodge bone using inner chamber 3920 and compress such bone distally of the anchor 3900 to form a compressed bone region 3921 along the axis of bone anchor 3900 in the region in front of (distally) the bone anchor 3900. Again, in some implementations, compressed bone region 3921 may be advanced so as to contact cortical bone, such as against a cortical wall opposite from the entry point of the bone anchor 3900. However, in other implementations, the effective fixation length may be sufficiently lengthened by use of the compressed bone region 3921 so as to provide significant benefit without extending the compressed bone region 3921 into a cortical bone and/or distal bone wall.

If, however, the type of fracture and/or quality of bone suggests that bicortical fixation would be desirable, the angle of the bone anchor 3900 may be selected so as to extend the compressed bone region 3921 against a distal cortical wall. Thus, for example, the implementation depicted in FIG. 39 may be altered such that the bone anchor 3900 is angled downward to provide for a more rigid, bicortical fixation (again, without requiring penetration of the distal cortical wall).

Figure 40:
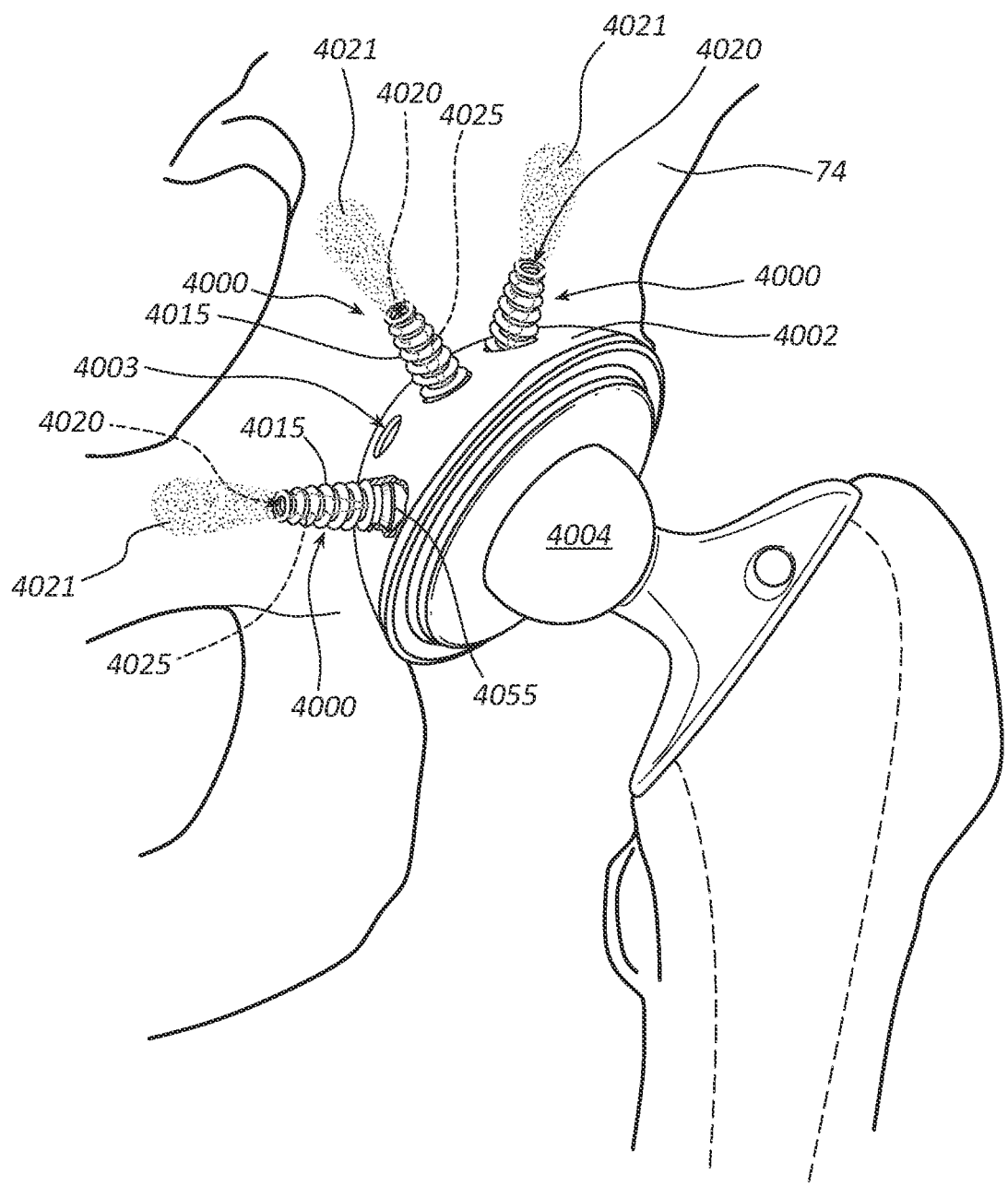
FIG. 40 depicts a series of bone anchors used to affix an acetabular component of a hip implant as part of a hip replacement surgery.

Yet another embodiment of a bone anchor system comprising a plurality of bone anchors 4000 is shown in FIG. 40. Bone anchors 4000 are shown used in a hip implant system comprising an acetabular cup component 4002 and a femoral head component 4004.

Each of the bone anchors 4000 is shown extending into a portion of the pelvis bone 74 adjacent to the acetabulum of a patient. In doing so, each bone anchor 4000 extends through an opening 4003 formed in the acetabular cup 4002. An enlarged head or flange 4055 of each bone anchor 4000 is used to engage the acetabular cup 4002 to fix the cup 4002 in position within the bone surrounding the acetabulum.

Each of the bone anchors 4000 has been positioned within the pelvic bone 74 so as to compress the bone and create a compressed bone region 4021 in front of the bone anchor 4000 to, as mentioned above, increase the effective fixation length of each bone anchor 4000, increase the strength of the resulting bone fixation, and/or decrease the chances for loosening and/or failure.

Each of the bone anchors 4000 may comprise any or all of the features mentioned herein in connection with other bone anchors, such as external threads 4015, and inner chamber 4020, which preferably includes one or more means for engaging, drawing in, redistributing, and/or compacting bone, such as internal threads 4025. One or more of the bone anchors 4000 may also be installed so as to extend their respective compressed bone regions 4021 against cortical bone, such as a distal cortical wall, to effectively create bicortical purchase without penetration of the cortical bone and/or distal cortical wall.

Figure 41:
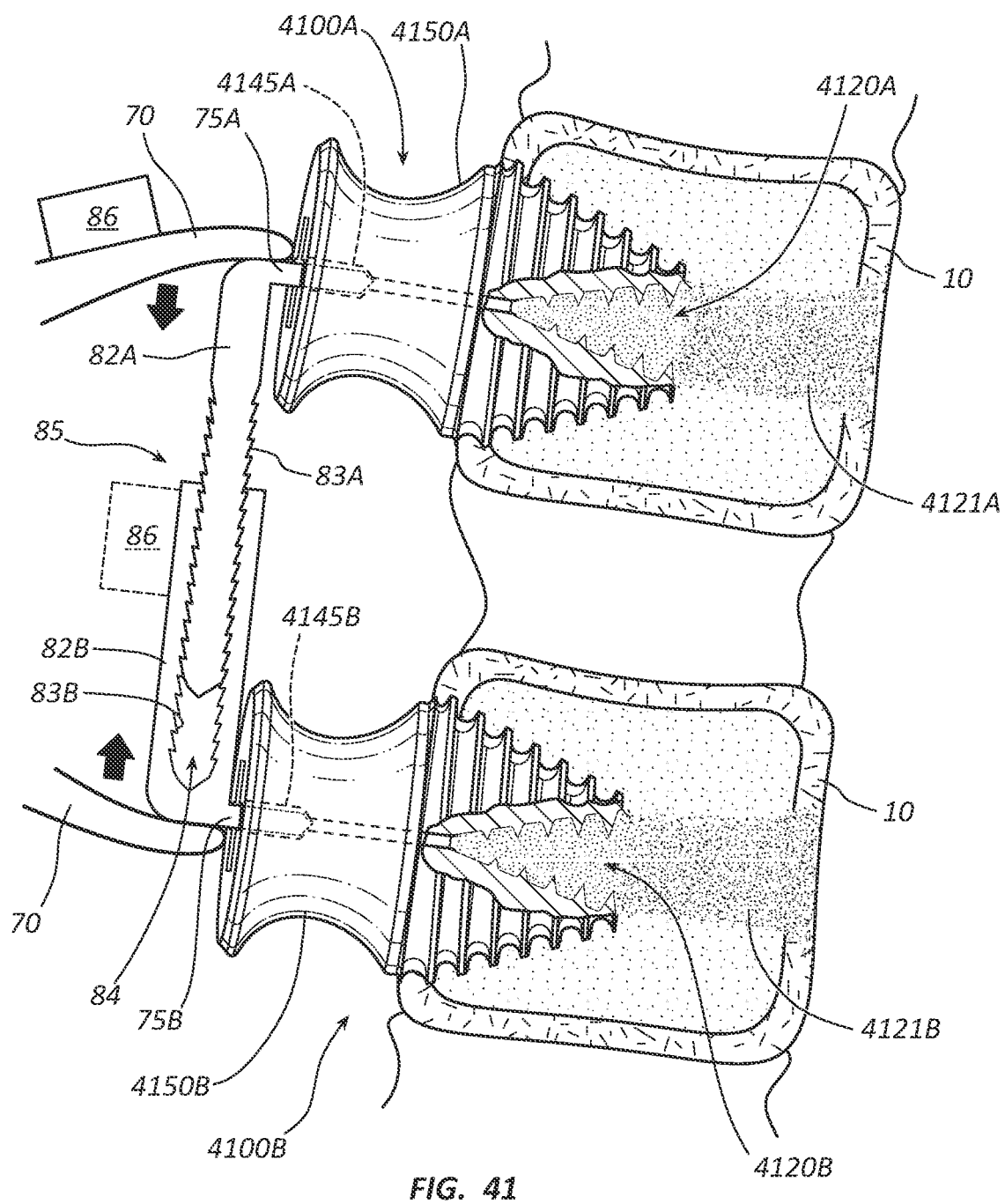
FIG. 41 depicts an example of an instrument used to selectively apply a corrective force to an adjacent pair of vertebral bone anchors according to some embodiments.

FIG. 41 depicts another example of a system for spinal deformity correction. This system is shown with two adjacent bone anchors, namely, bone anchor 4100A and bone anchor 4100B, positioned in two adjacent vertebral bodies 10. The bone anchors 4100A/4100B themselves may be similar to, such as including one or more of the features of, any of the bone anchors disclosed herein. Thus, in the depicted example, each of the bone anchors 4100A/4100B comprises a respective saddle 4150A/4150B for engagement with a ligament or another preferably flexible engagement member.

Both bone anchors 4100A/4100B further comprise a respective inner chamber 4120A/4120B, preferably including means for engagement, drawing in, redistribution, and/or compaction of cancellous bone, such as internal threads.

In addition, both bone anchors 4100A/4100B have been installed so as to form a respective compressed bone region 4121A/4121B that contacts the distal cortical wall of its respective vertebral body to form functional and/or effective bicortical purchase without penetration of the distal cortical wall.

Once sufficient fixation has been achieved, an instrument 85 may be used to draw the adjacent bone anchors 4100A/4100B towards one another prior to applying a tether or ligament. The instrument 85 shown in FIG. 41 comprises a ratcheting mechanism and should therefore be considered an example of means for selectively increasing the force between the adjacent anchors 4100A and 4100B. The depicted embodiment should also be considered an example of means for selectively increasing the force between the adjacent anchors 4100A and 4100B in a stepwise manner.

A series of ratcheting teeth 83A may be formed along a male shaft 82A of the instrument 85, which male shaft 82A is configured to be received in a slot 84 of a female portion 82B of instrument 85. Teeth 83A are configured to cooperate with a corresponding set of ratcheting teeth 83B within slot 84 to allow for application of a compressive force between the vertebral bodies in a stepwise manner.

Each of the respective saddles 4150A/4150B or, in alternative embodiments, another ligament engagement member or other proximal feature of the anchors 4100A/4100B, comprises a respective slot 4145A/4145B for receipt of a respective engagement arm 75A/75B of the instrument 85. In some embodiments, one or both of engagement arms 75A/75B may be configured to pivot and/or rotate to allow for insertion into respective slots 4145A/4145B in a non-parallel configuration. Alternatively, resiliently flexible engagement arms 75A/75B may be used.

Some embodiments may further comprise force sensors and/or a display 86 or another notification means. In this manner, application of a desired amount of force yet not excessive force to the vertebral bodies may be facilitated. For example, some embodiments may comprise one or more force sensors, such as a piezoelectric force sensor, a strain gauge, capacitive sensor, inductive sensor, or the like, which may be communicatively coupled with display 86. Sensors, display, and/or notification means 86 may be configured to display a digital output of the sensor. In addition, or alternatively, sensors, display, and/or notification means 86 may be configured to provide a warning upon reaching a threshold amount of force, such as an audible warning, a visible warning, a tactile warning, or the like.

Because corrective forces on the vertebral bodies will typically be low initially relative to the change in distance applied using instrument 85, but will then increase dramatically with small changes in distance as maximum compressive forces are reached, such warnings may be particularly useful for a surgeon to avoid application of excessive forces that may lead to implant and/or bone failure.

In some embodiments, the display 86 may also, or alternatively, be configured to display the precise distance between the adjacent vertebral bodies. This may allow a surgeon to select a size of loop tether more accurately to ultimately extend over the saddles 4150A/4150B. Some implementations involving use of instrument 85 may also comprise application of compressive forces that are intentionally left in place for a predetermined time interval, such as several minutes or more, to allow for additional correction through vertebral disc relaxation and accommodation.

It is contemplated that a surgeon may apply force to instrument 85 manually or may use another instrument to apply such force, such as forceps 70. Some embodiments may therefore comprise a groove or another engagement feature along one or both sides of instrument 85 to facilitate use of such a squeezing/force applying instrument 70. In addition, as shown in FIG. 41, sensors, display, and/or notification means 86 may alternatively be coupled and/or used in connection with instrument 70, if desired.

Figure 42:
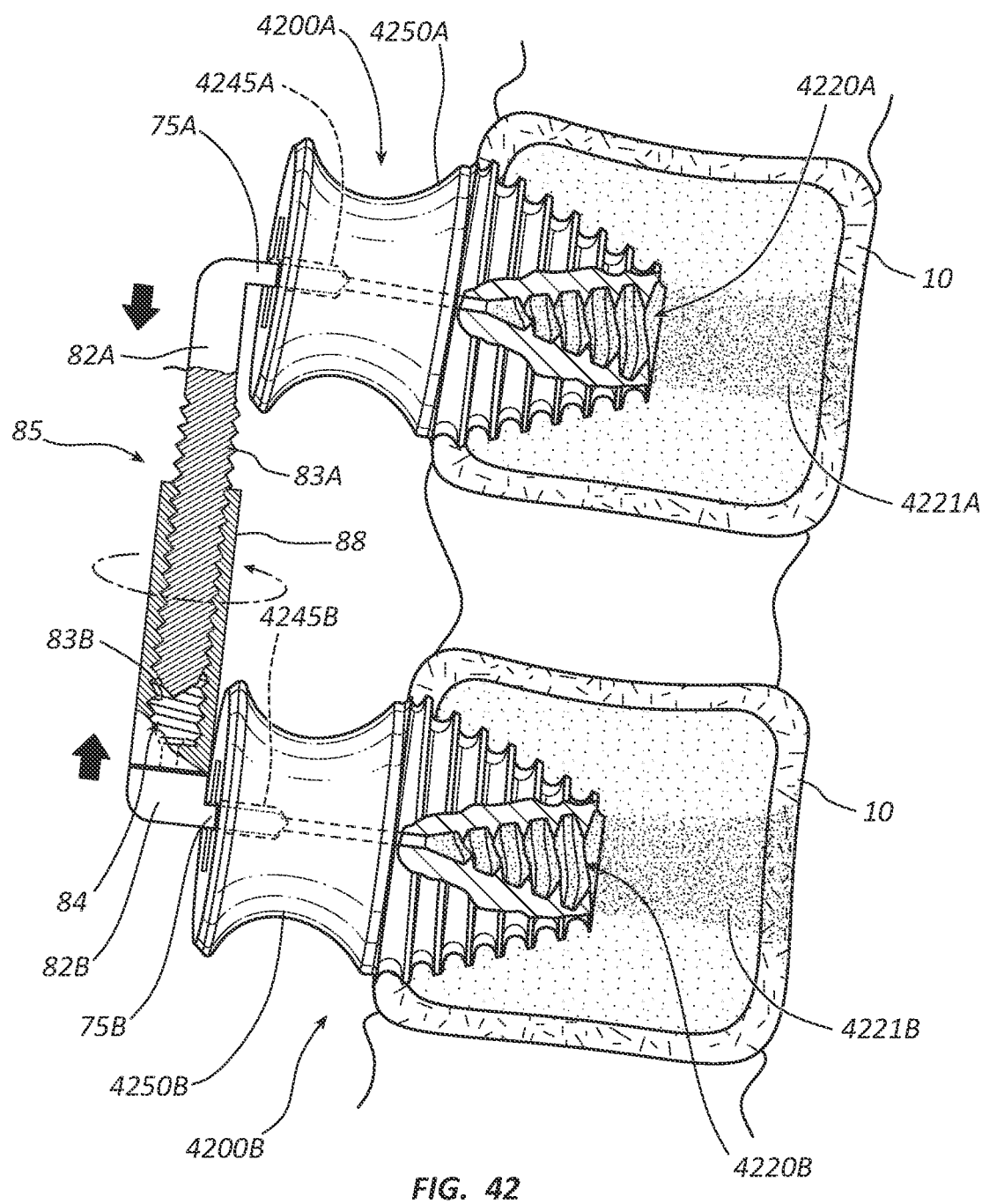
FIG. 42 depicts another example of an instrument. used to selectively apply a corrective force to an adjacent pair of vertebral bone anchors according to other embodiments.

FIG. 42 depicts yet another example of a system for spinal deformity correction. This system is again shown with two adjacent bone anchors, namely, bone anchor 4200A and bone anchor 4200B, positioned in two adjacent vertebral bodies 10. The bone anchors 4200A/4200B themselves may be similar to, such as including one or more of the features of, any of the bone anchors disclosed herein. Thus, bone anchors 4200A/4200B each comprises a respective saddle 4250A/4250B for engagement with a ligament or another preferably flexible engagement member. Bone anchors 4200A/4200B each further comprises a respective inner chamber 4220A/4220B, preferably including means for engagement, drawing in, redistribution, and/or compaction of cancellous bone, such as internal threads.

In addition, both bone anchors 4200A/4200B have been installed so as to form a respective compressed bone region 4221A/4221B that contacts the distal cortical wall of its respective vertebral body to form functional and/or effective bicortical purchase without penetration of the distal cortical wall.

Once sufficient fixation has been achieved, instrument 85 may be used to draw the adjacent bone anchors 4200A/4200B towards one another prior to applying a tether or ligament. The instrument 85 shown in FIG. 42 comprises a threaded mechanism and should therefore also be considered an example of means for selectively increasing the force between the adjacent anchors 4200A and 4200B. The depicted embodiment of FIG. 42 should also be considered an example of means for selectively increasing the force between the adjacent anchors 4200A and 4200B in a stepwise manner (in this case, with infinite steps rather than finite steps defined by the ratcheting teeth, as in the instrument of FIG. 41).

A series of external threads 83A may be formed along a male shaft 82A of the instrument 85, which male shaft 82A is configured to be received in a slot 84 of a female portion 82B of instrument 85. External threads 83A are configured to cooperate with a corresponding set of internal threads 83B within slot 84 to allow for application of a compressive force between the vertebral bodies in an (infinite, in this case) stepwise manner. The female portion 82B of the instrument may comprise a rotatable sleeve 88. Thus, rotation of the sleeve may result in approximation, or distraction in the opposite direction, of the two anchors 4200A/4200B, along with their respective vertebral bodies.

Each of the respective saddles 4250A/4250B or, in alternative embodiments, another ligament engagement member or other proximal feature of the anchors 4200A/4200B, comprises a respective slot 4245A/4245B for receipt of a respective engagement arm 75A/75B of the instrument 85. Again, in some embodiments, one or both of engagement arms 75A/75B may be configured to pivot and/or rotate to allow for insertion into respective slots 4245A/4245B in a non-parallel configuration. Alternatively, resiliently flexible engagement arms 75A/75B may be used.

Some embodiments may further comprise force sensors and/or a display or another notification means, as mentioned above in connection with FIG. 42. Some embodiments may also, or alternative, be configured to provide a warning upon reaching a threshold amount of force, such as an audible warning, a visible warning, a tactile warning, or the like.

Figure 43:
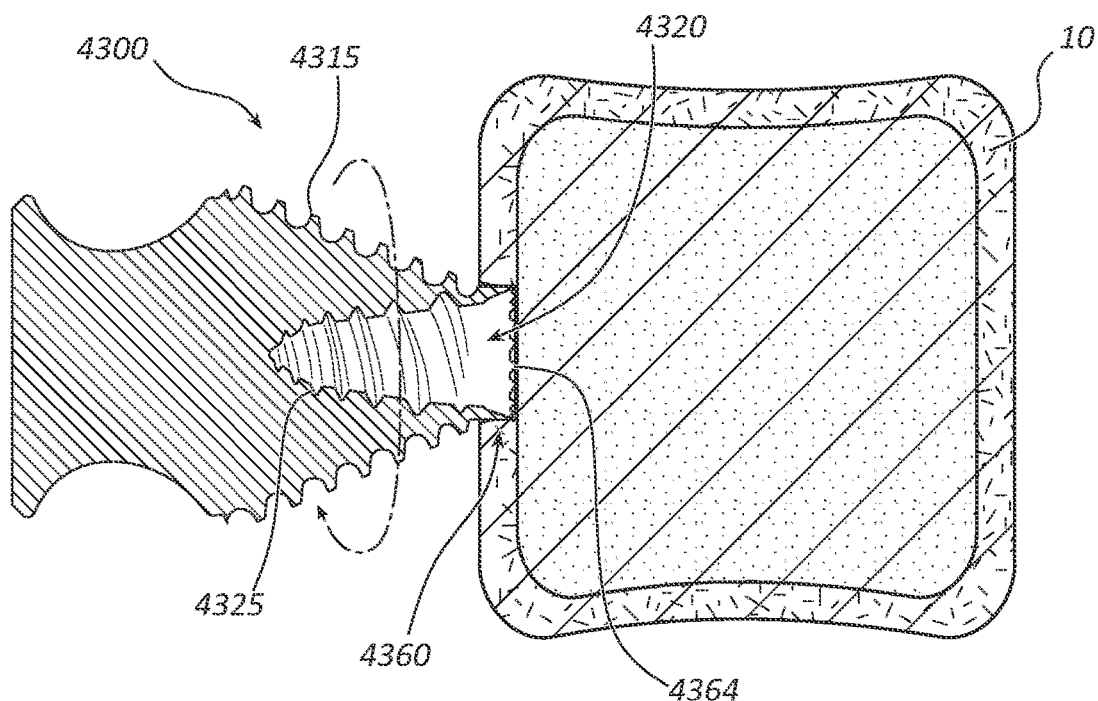
FIG. 43 depicts an alternative embodiment of a vertebral bone anchor having a slightly widened, cylindrical, unthreaded tip configured to create an initial, cylindrical opening in the proximal cortical wall before engagement of the outer threads of the anchor.

FIG. 43 illustrates another bone anchor 4300 used in the context of a vertebrae 10. This bone anchor 4300 comprises an external thread form 4315 and an inner chamber 4320 having an inner thread form 4325.

Bone anchor 4300 further comprises a non-tapering, cylindrical introducer tip 4360. Tip 4360 extends from the distal end of a tapering portion of the inner chamber 4320 and terminates at a tip or edge 4364 to facilitate penetration into a vertebral body 10 or other bone, as shown in FIG. 43. In the depicted embodiment, tip 4360 lacks both internal and external threads. As such, bone anchor 4300 may be tamped into the bone before engaging any of the threads.

In addition, the distal edge of introducer tip 4360 comprises a non-smooth distal edge 4364. This edge 4364 may comprise, for example, a series of spikes, nubs, or may simply comprise a roughened edge. This may allow a surgeon to tamp or rotate the bone anchor 4300 back and forth to initially obtain purchase into the proximal cortical wall.

Preferably, introducer tip 4360 has a slightly larger width than the adjacent outer section of bone anchor 4300. This adjacent section may either lack outer threads, or such threads may be formed but not extend to or beyond the width of the introducer tip 4360. This may allow the introducer tip 4360 to create an initial purchase in the proximal cortical wall without simultaneously engaging the outer thread form 4315. After advancing the bone anchor 4300 beyond this point (again, either by tamping or rotating back and forth, for example), the threads can then be engaged within the cylindrical depression in the proximal cortical wall created by introducer tip 4360 to begin threading the bone anchor 4300 into the vertebral body 10.

Figure 44:
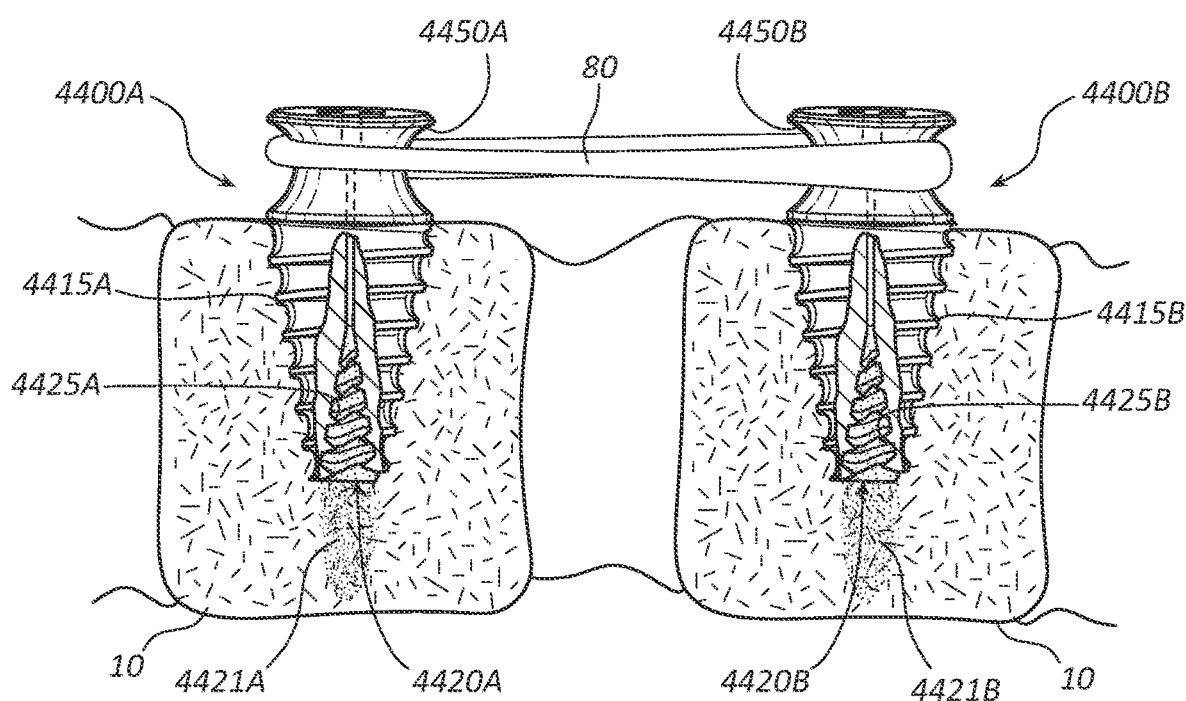
FIG. 44 depicts a completed vertebral correction system in which both adjacent bone anchors have been placed so as to create functional bicortical purchase to increase fixation strength without penetration of their respective distal cortical walls.

FIG. 44 illustrates another embodiment of a system for spinal correction that includes two vertebral bone anchors, namely, bone anchors 4400A and 4400B. Both bone anchors 4400A/4400B may have one or more of the features previously mentioned. For example, the depicted embodiments comprise respective outer thread forms 4415A/4415B and inner chambers 4420A/4420B having respective inner thread forms 4425A/4425B.

In addition, both anchors 4400A/4400B have been installed so as to advance a respective compressed bone region 4421A/4421B against a distal, cortical wall of its respective vertebral body 10, thereby providing a configuration of similar, if not greater, strength than two adjacent bicortical screws without the danger of penetrating the distal cortical walls. A tether 80 has been coupled between the two anchors 4400A/4400B to provide a continuous, restorative force to the spine. Moreover, the fixation provided by the compressed bone regions 4421A/4421B provides a biological component to the fixation that allows for a gradual and gentle reduction in rigidity from the proximal to distal end, thereby creating fixation that is much closer to the normal, biomechanical elasticity of bone. This also may provide less rigidity or stiffness at the bone surface, thereby putting less stress and reduced peak forces on the tether 80.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims. The scope of the present invention should, therefore, be determined only by the following claims.

The invention claimed is:

1. A method for applying a corrective force to a spinal column, the method comprising the steps of:
    advancing a first bone anchor through a proximal cortical wall of a first vertebral body of a spinal column and into the first vertebral body;
    compressing cancellous bone within the first vertebral body in a region distal of the first bone anchor by advancing the first bone anchor within the first vertebral body to form a compressed bone region distal of the first bone anchor; and
    extending the compressed bone region distally of the first bone anchor by advancing the first bone anchor until the compressed bone region contacts a distal cortical wall opposite from the proximal cortical wall, wherein the step of extending the compressed bone region distally of the first bone anchor by advancing the first bone anchor until the compressed bone region contacts a distal cortical wall increases a fixation strength of the first bone anchor within the first vertebral body.

2. The method of claim 1, wherein the compressed bone region forms a gradient of increasing bone density along an axis of the first bone anchor.

3. The method of claim 1, further comprising:
advancing a second bone anchor through a proximal cortical wall of a second vertebral body of the spinal column and into the second vertebral body;
compressing cancellous bone within the second vertebral body in a region distal of the second bone anchor by advancing the second bone anchor within the second vertebral body to form a compressed bone region distal of the second bone anchor; and
extending the compressed bone region distally of the second bone anchor by advancing the second bone anchor until the compressed bone region contacts a distal cortical wall of the second vertebral body opposite from the proximal cortical wall of the second vertebral body, wherein the step of extending the compressed bone region distally of the second bone anchor by advancing the second bone anchor until the compressed bone region contacts a distal cortical wall of the second vertebral body opposite from the proximal cortical wall of the second vertebral body increases a fixation strength of the second bone anchor within the second vertebral body; and
coupling a tether between the first and second bone anchors to apply a force between the first and second bone anchors and thereby apply a corrective force to at least a portion of the spinal column of a patient.

4. The method of claim 3, wherein the first and second bone anchors each comprises an inner chamber, and further comprising compacting cancellous bone into the respective inner chambers of the first and second bone anchors as the first and second bone anchors are advanced such that the first and second bone anchors achieve bicortical fixation of the first and second vertebral bodies, respectively, without penetrating respective distal cortical walls of the first and second vertebral bodies.

5. The method of claim 1, wherein the compressed bone region is formed so as to, upon healing, form a solidified bone shaft that extends from the distal cortical wall to a distal end of the first bone anchor along an axis of the first bone anchor, wherein the solidified bone shaft comprises bone of a higher density than at least a portion of cancellous bone surrounding the solidified bone shaft within the first vertebral body.

6. A method for fixation of a bone anchor, the method comprising the steps of:
advancing a bone anchor through a proximal bone wall and into a bone of a patient;
compressing bone material within the bone in a region distal of the bone anchor by advancing the bone anchor within the bone to form a compressed bone region, the compressed bone region extending, at least in part, distally of the bone anchor, wherein the compressed bone region increases a fixation strength of the bone anchor within the bone to decrease the chances of the bone anchor becoming dislodged within the bone; and
coupling a flexible member to the bone anchor.

7. The method of claim 6, wherein the flexible member comprises a tendon, and wherein the bone anchor comprises a suture anchor.

8. The method of claim 7, wherein the suture anchor comprises an inner chamber, and wherein the method comprises compacting bone material into the inner chamber as the suture anchor is advanced to form the compressed bone region.

9. The method of claim 7, wherein the tendon comprises either an Achilles tendon or a rotator cuff tendon.

10. The method of claim 6, wherein the flexible member comprises a flexible coupling member.

11. The method of claim 10, wherein the flexible coupling member comprises a ligament.

12. The method of claim 6, wherein the bone anchor comprises an inner chamber, wherein the inner chamber comprises one or both of: (1) a plurality of bone engaging protrusions formed on an inner surface of the inner chamber; and (2) a profile that increases in cross-sectional area, at least in part, from a proximal end of the inner chamber to a distal end of the inner chamber, and wherein the method further comprises compressing bone material into the inner chamber.

13. The method of claim 12, wherein the inner chamber comprises a plurality of bone engaging protrusions, wherein the plurality of bone engaging protrusions comprises an inner thread form formed on an inner surface of the inner chamber, wherein the bone comprises a vertebral bone, and wherein the step of compressing bone material into the inner chamber comprises:
compressing cancellous bone into the inner chamber while simultaneously forming the compressed bone region distally of the bone anchor and along an axis of the bone anchor; and
coupling a tether with the bone anchor to apply a corrective force to at least a portion of a spinal column of the patient.

14. The method of claim 6, wherein the bone material comprises cancellous bone.

15. A method for increasing a fixation strength of a bone anchor, the method comprising the steps of:
advancing a bone anchor through a proximal cortical wall of a bone, wherein the bone anchor comprises an inner chamber;
advancing the bone anchor to compress cancellous bone into the inner chamber of the bone anchor;
increasing an effective fixation length of the bone anchor by advancing and compressing cancellous bone along an axis of the bone anchor and in a region distal of the bone anchor; and
applying a lateral force to the bone anchor through another implant and/or implant part coupled with the bone anchor, wherein the effective fixation length increases a fixation strength of the bone anchor within the bone.

16. The method of claim 14, wherein the bone anchor comprises a vertebral bone anchor, and wherein the bone comprises a vertebral body.

17. The method of claim 16, wherein the step of applying a force to the bone anchor comprises applying a force to the bone anchor with a flexible member to apply a corrective force to a patient's spinal column.

18. The method of claim 14, wherein the bone comprises a tibia, a femur, a calcaneus, or a humerus.

19. The method of claim 14, wherein the step of increasing an effective fixation length of the bone anchor by advancing and compressing cancellous bone along an axis of the bone anchor and in a region distal of the bone anchor further comprises forming a compressed bone region along the region distal of the bone anchor.

20. The method of claim 19, further comprising advancing the bone anchor until the compressed bone region contacts a distal cortical wall of the bone opposite from the proximal cortical wall.

21. A method for increasing a fixation strength of a bone anchor, the method comprising the steps of:
- advancing a bone anchor through a proximal cortical wall of a bone, wherein the bone comprises a tibia, a femur, a calcaneus, or a humerus, and wherein the bone anchor comprises an inner chamber;
- advancing the bone anchor to compress cancellous bone into the inner chamber of the bone anchor;
- increasing an effective fixation length of the bone anchor by advancing and compressing cancellous bone along an axis of the bone anchor and in a region distal of the bone anchor; and
- applying a force to the bone anchor, wherein the effective fixation length increases a fixation strength of the bone anchor within the bone.

\* \* \* \* \*